(12) United States Patent
Dobrusin et al.

(10) Patent No.: US 7,501,425 B1
(45) Date of Patent: Mar. 10, 2009

(54) BICYCLIC PYRIMIDINES AND BICYCLIC 3,4-DIHYDROPYPRIMIDINES AS INHIBITORS OF CELLULAR PROLIFERATION

(75) Inventors: Ellen Myra Dobrusin, Ann Arbor, MI (US); James Marino Hamby, Ann Arbor, MI (US); James Bernard Kramer, Sylvania, OH (US); Mel Conrad Schroeder, Dexter, MI (US); Howard Daniel Hollis Showalter, Ann Arbor, MI (US); Peter Toogood, Ann Arbor, MI (US); Susanne A. Trumpp-Kallmeyer, Moeindal (DE)

(73) Assignee: Warner Lambert Company, New York, NY (US)

( * ) Notice: Subject to any disclaimer, the term of this patent is extended or adjusted under 35 U.S.C. 154(b) by 799 days.

(21) Appl. No.: 09/623,737

(22) PCT Filed: May 10, 1999

(86) PCT No.: PCT/US99/10187

§ 371 (c)(1),
(2), (4) Date: Sep. 7, 2000

(87) PCT Pub. No.: WO99/61444

PCT Pub. Date: Dec. 2, 1999

(51) Int. Cl.
*A61K 31/519* (2006.01)
*C07D 471/04* (2006.01)

(52) U.S. Cl. .................. 514/262.1; 544/256
(58) Field of Classification Search ............ 514/258, 514/300, 303, 262.1; 544/244, 256, 279; 546/23, 24, 118, 122, 123
See application file for complete search history.

(56) References Cited

U.S. PATENT DOCUMENTS

| | | | |
|---|---|---|---|
| 2,949,466 A | 8/1960 | Hoefle et al. | |
| 3,912,723 A | 10/1975 | Miller | |
| 3,939,084 A | 2/1976 | Sullivan | |
| 4,425,346 A | 1/1984 | Horlington | |
| 4,886,807 A | 12/1989 | Kitamura et al. | |
| 5,654,307 A | 8/1997 | Bridges et al. | 514/258 |
| 6,084,095 A | 7/2000 | Bridges et al. | |
| 6,150,373 A * | 11/2000 | Harris et al. | 514/258 |

FOREIGN PATENT DOCUMENTS

| | | |
|---|---|---|
| EP | 0021292 | 1/1981 |
| EP | 0278686 | 8/1988 |
| JP | 11-158180 | 6/1999 |
| WO | 92 20642 | 11/1992 |
| WO | 95 19774 | 7/1995 |
| WO | 96 15128 | 5/1996 |
| WO | WO 96/13262 | 5/1996 |
| WO | 96 34867 | 11/1996 |
| WO | 97 38983 | 10/1997 |
| WO | 98 33798 | 8/1998 |
| WO | 99 06378 | 2/1999 |
| WO | 99 09030 | 2/1999 |
| WO | WO 99/61444 | 12/1999 |
| WO | WO 00/24744 | 5/2000 |
| WO | WO 01/29041 A1 | 4/2001 |
| WO | WO 01/29042 A1 | 4/2001 |
| WO | WO 01/64679 A1 | 9/2001 |

OTHER PUBLICATIONS

G.W. Rewcastle, et al., Journal of Medicinal Chemistry, "Tyrosine Kinase Inhibitors. 10. Isometric 4-[(3-Bromopheny)Amino]Pyrido[D]Pyrimidines are Potent ATP Binding Site Inhibitors of the Tyrosine Kinase Function of the Epidermal Growth Factor Receptor", vol. 39, 199956 pp. 1823-1835, XP002046257.

G.W. Rewcastle, et al., Journal of Medicinal Chemistry, "Tyrosine Kinase Inhibitors. T. Synthesis-Activity Relationships for 4-[(Phenylmethyl)Amino]-and 4-(Phenylamino) Quinazolines as Potent Adenosine 5'- Triphosphate Binding Site Inhibitors of the Tyrosine Kinase Domain of the Epidermal Growth Factor Receptor", vol. 38, 1995, pp. 3482-3487, XP000673491.

(Continued)

*Primary Examiner*—James O Wilson
*Assistant Examiner*—Tamthom N Truong
(74) *Attorney, Agent, or Firm*—Bryan C. Zielinski; Stephen D. Prodnuk

(57) ABSTRACT

This invention provides substituted pyrimido-pyrimidines that are useful for treating cell proliferative disorders, such as cancer and restenosis, as well as angiogenesis and atherosclerosis. The invention compounds have Formula I:

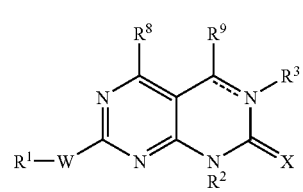

where
W is NH, S, SO, or $SO_2$,
$R^1$ includes alkyl, cycloalkyl, phenyl, substituted phenyl, heteroaryl and substituted heteroaryl;
$R^2$ includes alkyl, cycloalkyl, phenyl and substituted phenyl;
$R^3$ includes alkyl and aryl such as phenyl and substituted phenyl;
$R^8$ and $R^9$ include hydrogen and alkyl, and the pharmaceutically acceptable salts thereof.

The invention also provides pharmaceutical formulations comprising a compound of Formula I together with a pharmaceutically acceptable carrier, diluent, or excipient therefor, and a method for treating angiogenesis using said compounds.

36 Claims, No Drawings

OTHER PUBLICATIONS

Adachi, K., "Synthesis of Orcinol Monomethyl Ether," *Memoirs of the Osaka Institute of Technology, Series A*, 1983, 33-42, vol. 28, No. 1.

Cappuccino, J., et al., "Growth Inhibition of *Clostridium feseri* by Carcinostatic Purine and Pyrimidine Analogs—I. Effect of Medium on Growth Inhibition," *Cancer Research*, 1964, 1243-1248, vol. 24, No. 7.

Chatterjee, S., et al., "Synthesis of Some 4-Oxy & 2:4-Dioxypyrimido-(4,5-d)-pyrimidines," *Journal of Scientific & Industrial Research*, 1958, 63-70, vol. 17.

Chatterjee, S., et al, "Synthesis of Some Pyrimido(4,5-d)Pyrimidines as Potential Purine Antagonists," *Journal of Scientific & Industrial Research*, 1959, 272-278, vol. 18.

Devi, N., et al, "Synthesis of Pyrimido [4,5-d] Pyrimidines as Antifungal Agents," *Indian Journal of Heterocyclic Chemistry*, 1998, 193-196, vol. 7.

Evers, R., et al., "Zum Reaktionsverhalten der Thio-bis-formamidine; Versuche zur Synthese von Pyrimidino[4,5-d]pyrimidin-derivaten," *Z. Chem.*, 1980, 412-413, vol. 20.

Graboyes, H., et al, "Pteridines. X. Some Pyrimidopyrimidine Isomers of Triamterene," *Pteridines*, 1968, 568-573, vol. 11.

Grohe, K., et al., "Synthese and Reaktionen von Pyrimido[4,5-d]pyrimidinen," *Liebigs Ann. Chem.*, 1974, 2066-2073.

Gulevskaya, A., et al., "Purines, Pyrimidines, and Condended Systems Based on these Compounds," *Chemistry of Heterocyclic Compounds*, 1994, 1083-1086, vol. 30, No. 9.

Gulevskaya, A., et al., "Purines, Pyrimidines, and Condensed Systems Based on these Compounds," *Chemistry of Heterocyclic Compounds*, 1994, 1087-1091, vol. 30, No. 9.

Hirota, K., et al., "A Facile Synthesis of 7-Substituted Pyrimido[4,5-d]-*pyrimidine* -2,4-diones," *Synthesis*, 1984, 589-590, vol. 1984, No. 7.

Hirota, K., et al., "Novel Ring Transformations of 5-Cyanouracils into 2-Thiocytosines, 2,4-Diaminopyrimidines, and Pyrimido[4,5-d]pyrimidines by the Reaction with Thioureas and Guanidines," *Journal of the Chemical Society, Perkin Transactions 1*, 1990, 123-128, vol. 13.

Marsh, A., et al, "Self-Complementary Hydrogen Bonding Heterocycles Designed for the Enforced Self-Assembly into Supramolecular Macrocycles," *Chemical Communications*, 1996, 1527-1528, No. 13.

Masquelin, T., et al., "A Novel Solution- and Solid-Phase Approach to 2,4,5-Tri- and 2,4,5,6- Tetra-substituted Pyrimidines and Their Conversion into Condensed Heterocycles," *Helvetica Chimica Acta*, 1998, 646-660, vol. 81, No. 4.

Rewcastle, G. W., et al., "Tyrosine Kinase Inhibitors. 5. Synthesis and Structure-Activity Relationships for 4-[(Phenylmethyl)amino]- and 4-(Phenylamino)quinazolines as Potent Adenosine 5'-Triphosphate Binding Site Inhibitors of the Tyrosine Kinase Domain of the Epidermal Growth Factor Receptor," *Journal of Medicinal Chemistry*, 1995, 3482-3487, vol. 38, No. 18.

Rewcastle, G. W., et al., "Tyrosine Kinase Inhibitors. 10. Isomeric 4-[(3-Bromophenyl)amino]pyrido[d]-pyrimidines Are Potent ATP Binding Site Inhibitors of the Tyrosine Kinase Function of the Epidermal Growth Factor Receptor," *Journal of Medicinal Chemistry*, 1996, 1823-1835, vol. 39, No. 9.

Srivastava, S. K., et al., "A Solid Phase Approach to Substituted Pyrimidines and Their Conversion into Condensed Heterocycles for Potential Use in Combinatorial Chemistry," *Combinatorial Chemistry & High Throughput Screening*, 1999, 33-37, vol. 2, No. 1.

Taylor, E., et al, "Pyrimido [4,5-d]Pyrimidines. Part I," *Journal of the American Chemical Society*, 1960, 5711-5718, vol. 82, No. 21.

Tominaga, Y., et al., "Synthesis of Pyrimido[4,5-d]Pyrimidines," *Heterocycles*, 1979, 503-504, vol. 12, No. 4.

Tominaga, Y., et al., "Reaction of 6-Aminouracils with Ketenethioacetals," *Chemical and Pharmaceutical Bulletin*, 1984, 122-129, vol. 32, No. 1.

Wamhoff, H., et al, "Pyrimido[4,5-d]Pyrimidines, Pyrimido[4',5':4,5]Pyrimido[6,1-a]-Azepines, and an Imidazo[5,1-f][1,2,4]Triazine by Three Component Reaction," *Heterocycles*, 1993, 1055-1066, vol. 35, No. 2.

\* cited by examiner

BICYCLIC PYRIMIDINES AND BICYCLIC 3,4-DIHYDROPYRIMIDINES AS INHIBITORS OF CELLULAR PROLIFERATION

FIELD OF THE INVENTION

This invention relates to bicyclic heterocycles that inhibit cyclin-dependent kinase and tyrosine kinase enzymes, and as such are useful to treat cell proliferative disorders such as angiogenesis, atherosclerosis, restenosis, and cancer.

SUMMARY OF THE RELATED ART

Cell cycle kinases are naturally occurring enzymes involved in regulation of the cell cycle (Meijer L., "Chemical Inhibitors of Cyclin-Dependent Kinases", *Progress in Cell Cycle Research*, 1995; 1:351-363). Typical enzymes include the cyclin-dependent kinases (cdk) cdk1 (also known as cdc2), cdk2, cdk4, cdk5, cdk6, and wee-1 kinase. Increased activity or temporally abnormal activation of these kinases has been shown to result in development of human tumors and other proliferative disorders such as restenosis. Compounds that inhibit cdks, either by blocking the interaction between a cyclin and its kinase partner, or by binding to and inactivating the kinase, cause inhibition of cell proliferation, and are thus useful for treating tumors or other abnormally proliferating cells.

Several compounds that inhibit cdks have demonstrated both preclinical and clinical anti-tumor activity. For example, flavopiridol is a flavonoid that has been shown to be a potent inhibitor of several types of breast and lung cancer cells (Kaur, et al. *J. Natl. Cancer Inst.*, 1992; 84:1736-1740; *Int. J Oncol.*, 1996; 9:1143-1168). The compound has been shown to inhibit cdk2 and cdk4. Olomoucine [2-(hydroxyethylamine)-6-benzylamine-9-methylpurine] is a potent inhibitor of cdk2 and cdk5 (Vesely, et al., *Eur. J. Biochem.*, 1994; 224:771-786), and has been shown to inhibit proliferation of approximately 60 different human tumor cell lines used by the National Cancer Institute (NCI) to screen for new cancer therapies (Abraham, et al., *Biology of the Cell*, 1995; 83:105-120).

In addition, tyrosine kinases are a class of enzymes that catalyze the transfer of the terminal phosphate of adenosine triphosphate (ATP) to tryrosine residues on protein substrates. Tyrosine kinases are an integral part of growth factor receptors and are essential for the propagation of growth factor signal transduction leading to cellular proliferation, differentiation, and migration. Growth factor receptors are also known as receptor tyrosine kinases (RTKs). The aberrant regulation of growth factors or their cognate receptors play a critical role in the progression of proliferative diseases. For example, the fibroblast growth factor (FGF) and the vascular endothelial growth factor (VEGF) have been implicated as important mediators of tumor promoted angiogenesis. Solid tumors are dependent upon the formation of new blood vessels from preexisting vessels (angiogenesis) to nourish their growth and to provide a conduit for metastases. Accordingly, inhibitors of the FGF and VEGF RTKs, as well as other tyrosine kinases, are useful agents for the prevention and treatment of proliferative diseases dependent on these enzymes.

Despite the progress that has been made, the search continues for small molecular weight compounds that are orally bioavailable and useful for treating a wide variety of human tumors and other proliferative disorders such as restenosis, angiogenesis, diabetic retinopathy, psoriasis, surgical adhesions, macular degeneration, and atherosclerosis.

SUMMARY OF THE INVENTION

This invention provides bicyclic heterocycles that are useful for treating cell proliferative disorders, such as cancer, atherosclerosis, restenosis, angiogenesis, diabetic retinopathy, psoriasis, and endometriosis. We have discovered a group of bicyclic pyrimidine analogs that are potent inhibitors of cyclin-dependent kinases (cdks) and tyrosine kinases. The compounds are readily synthesized and can be administered by a variety of routes, including orally and parenterally, and have little or no toxicity.

The compounds of the invention are members of the class of compounds of Formula I:

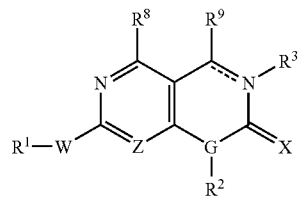

and the pharmaceutically acceptable salts thereof, wherein:

the dotted line represents an optional double bond;

Z is N or CH;

G is N or CH;

W is NH, S, SO, or $SO_2$;

X is either O, S, or $NR^{10}$;

$R^1$, $R^2$, and $R^{10}$ are independently selected from the group consisting of H, $(CH_2)_n Ar$, $COR^4$, $(CH_2)_n$heteroaryl, $(CH_2)_n$heterocyclyl, $C_1$-$C_{10}$ alkyl, $C_3$-$C_{10}$ cycloalkyl, $C_2$-$C_{10}$ alkenyl, and $C_2$-$C_{10}$ alkynyl, wherein n is 0, 1, 2, or 3, and the $(CH_2)_n Ar$, $(CH_2)_n$heteroaryl, alkyl, cycloalkyl, alkenyl, and alkynyl groups are optionally substituted by up to 5 groups selected from $NR^4R^5$, $N(O)R^4R^5$, $NR^4R^5R^6Y$, alkyl, phenyl, substituted phenyl, $(CH_2)_n$heteroaryl, hydroxy, alkoxy, phenoxy, thiol, thioalkyl, halo, $COR^4$, $CO_2R^4$, $CONR^4R^5$, $SO_2NR^4R^5$, $SO_3R^4$, $PO_3R^4$, aldehyde, nitrile, nitro, heteroaryloxy,

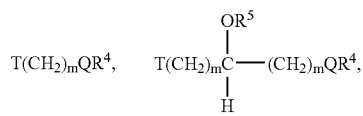

$C(O)T(CH_2)_m QR^4$, $NHC(O)T(CH_2)_m QR^4$, $T(CH_2)_m C(O)NR^4NR^5$, or $T(CH_2)_m CO_2R^4$ wherein each m is independently 1-6, T is O, S, $NR^4$, $N(O)R^4$, $NR^4R^6Y$, or $CR^4R^5$, and Q is O, S, $NR^5$, $N(O)R^5$, or $NR^5R^6Y$;

when the dotted line is present, $R^3$ is absent;

otherwise $R^3$ has the meanings of $R^2$, wherein $R^2$ is as defined above, as well as OH, $NR^4R^5$, $COOR^4$, $OR^4$, $CONR^4R^5$, $SO_2NR^4R^5$, $SO_3R^4$, $PO_3R^4$,

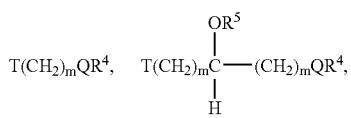

wherein T and Q are as defined above;

$R^4$ and $R^5$ are each independently selected from the group consisting of hydrogen, $C_1$-$C_6$ alkyl, substituted alkyl, $C_2$-$C_6$ alkenyl, $C_2$-$C_6$ alkynyl, $N(C_1$-$C_6alkyl)_{1\ or\ 2}$, $(CH_2)_n$Ar, $C_3$-$C_{10}$ cycloalkyl, heterocyclyl, and heteroaryl, or $R^4$ and $R^5$ together with the nitrogen to which they are attached optionally form a ring having 3 to 7 carbon atoms and said ring optionally contains 1, 2, or 3 heteroatoms selected from the group consisting of nitrogen, substituted nitrogen, oxygen, and sulfur;

when $R^4$ and $R^5$ together with the nitrogen to which they are attached form a ring, the said ring is optionally substituted by 1 to 3 groups selected from OH, $OR^4$, $NR^4R^5$, $(CH_2)_m OR^4$, $(CH_2)_m NR^4R^5$, T—$(CH_2)_m QR^4$, CO-T—$(CH_2)_m QR^4$, $NH(CO)T(CH_2)_m QR^4$, T—$(CH_2)_m CO_2R^4$, or $T(CH_2)_m CONR^4R^5$.

$R^6$ is alkyl;

$R^8$ and $R^9$ independently are H, $C_1$-$C_3$ alkyl, $NR^4R^5$, $N(O)R^4R^5$, $NR^4R^5R^6Y$, hydroxy, alkoxy, thiol, thioalkyl, halo, $COR^4$, $CO_2R^4$, $CONR^4R^5$, $SO_2NR^4R^5$, $SO_3R^4$, $PO_3R^4$, CHO, CN, or $NO_2$;

when the dotted line is absent, $R^9$ is additionally carbonyl, thiocarbonyl, imine and substituted imine, oxime and oxime ether, and Y is a halo counter-ion.

In a preferred embodiment, the invention provides compounds of Formula II, III, and IV

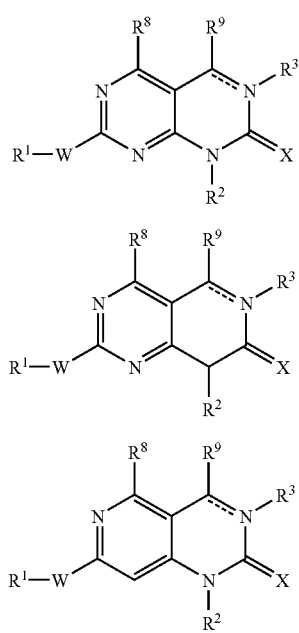

wherein $R^1$, $R^2$, $R^3$, $R^8$, and $R^9$ are as defined above.

Additionally preferred compounds have the above formulas wherein W is NH. Also preferred are those compounds wherein $R^1$ is substituted alkyl, phenyl, or pyridyl.

This invention also provides pharmaceutical formulations comprising a compound of Formula I together with a pharmaceutically acceptable carrier, diluent, or excipient therefor.

Compounds within the scope of the present invention are inhibitors of the cyclin-dependent kinases such as cdk2, cdc2, and cdk4. Some of the compounds of the present invention also inhibit growth factor mediated tyrosine kinases including those of platelet-derived growth factor (PDGF), fibroblast growth factor (FGF), and epidermal growth factor (EGF), as well as non-receptor tyrosine kinases such as c-Src. As inhibitors of cyclin-dependent, as well as growth factor-mediated and non-receptor tyrosine kinases, the compounds of the instant invention are useful in controlling proliferative disorders such as cancer, psoriasis, vascular smooth muscle cell proliferation associated with atherosclerosis, diabetic retinopathy and angiogenesis, and postsurgical vascular stenosis and restenosis in mammals.

A further embodiment of this invention is a method of treating subjects suffering from diseases caused by cellular proliferation. The method entails inhibiting proliferation of tumorigenic cells of epithelial origin and vascular smooth muscle proliferation, and/or cellular migration by administering a therapeutically effective amount of a compound of Formula I to a subject in need of treatment.

A further embodiment of this invention is a method of treating subjects suffering from diseases caused by DNA tumor viruses such as herpes viruses.

DETAILED DESCRIPTION OF THE INVENTION

We have discovered a new class of compounds that are potent inhibitors of cyclin-dependent kinases (cdks) and tyrosine kinases that are useful agents for treating subjects suffering from diseases caused by abnormal cell proliferation. Compounds within the scope of the present invention are inhibitors of the cyclin-dependent kinases such as cdc2, cdk2, and cdk4, and tyrosine kinases such as $PDGF_r$, $FGF_r$, and c-Src. As inhibitors of these kinases, the compounds of the instant invention are useful in controlling proliferative disorders such as cancer, psoriasis, vascular smooth muscle proliferation associated with atherosclerosis, postsurgical vascular stenosis, angiogenesis, diabetic retinopathy, and restenosis in mammals.

The compounds of the invention are members of the class of compounds of Formula I:

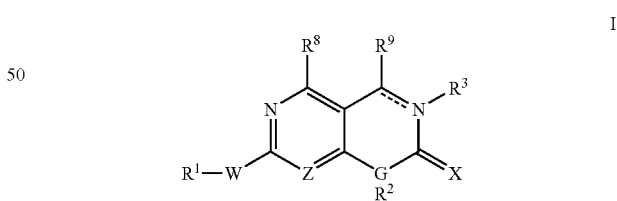

and the pharmaceutically acceptable salts thereof, wherein:

the dotted line ( - - - ) represents an optional double bond;

Z is N or CH;

G is N or CH;

W is NH, S, SO, or $SO_2$;

X is either O, S, or $NR^{10}$;

$R^1$, $R^2$, and $R^{10}$ are independently selected from the group consisting of H, $(CH_2)_n$Ar, $COR^4$, $(CH_2)_n$heteroaryl, ($CH_2$)$_n$heterocyclyl, $C_1$-$C_{10}$ alkyl, $C_3$-$C_{10}$ cycloalkyl, $C_2$-$C_{10}$ alkenyl, and $C_2$-$C_{10}$ alkynyl, wherein n is 0, 1, 2, or 3, and the ($CH_2$)$_n$Ar, ($CH_2$)$_n$heteroaryl, alkyl, cycloalkyl, alkenyl, and alkynyl groups are optionally substituted by up to 5 groups selected from $NR^4R^5$, $N(O)R^4R^5$, $NR^4R^5R^6Y$, alkyl, phenyl, substituted phenyl, ($CH_2$)$_n$heteroaryl, hydroxy, alkoxy, phenoxy, thiol, thioalkyl, halo, $COR^4$, $CO_2R^4$, $CONR^4R^5$, $SO_2NR^4R^5$, $SO_3R^4$, $PO_3R^4$, aldehyde, nitrile, nitro, heteroaryloxy,

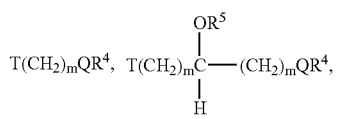

$C(O)T(CH_2)_mQR^4$, $NHC(O)T(CH_2)_mQR^4$, $T(CH_2)_mC(O)NR^4NR^5$, or $T(CH_2)_mCO_2R^4$ wherein each m is independently 1-6, T is O, S, $NR^4$, $N(O)R^4$, $NR^4R^6Y$, or $CR^4R^5$, and Q is O, S, $NR^5$, $N(O)R^5$, or $NR^5R^6Y$;

when the dotted line is present, $R^3$ is absent;
otherwise (when - - - is absent) $R^3$ has the meanings of $R^2$, wherein $R^2$ is as defined above, as well as OH, $NR^4R^5$, $COOR^4$, $OR^4$, $CONR^4R^5$, $SO_2NR^4R^5$, $SO_3R^4$, $PO_3R^4$,

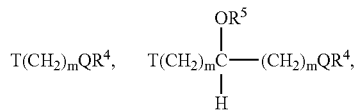

wherein T and Q are as defined above;
$R^4$ and $R^5$ are each independently selected from the group consisting of hydrogen, $C_1$-$C_6$ alkyl, substituted alkyl, $C_2$-$C_6$ alkenyl, $C_2$-$C_6$ alkynyl, $N(C_1$-$C_6alkyl)$ 1 or 2, ($CH_2$)$_n$Ar, $C_3$-$C_{10}$ cycloalkyl, heterocyclyl, and heteroaryl, or $R^4$ and $R^5$ together with the nitrogen to which they are attached optionally form a ring having 3 to 7 carbon atoms and said ring optionally contains 1, 2, or 3 heteroatoms selected from the group consisting of nitrogen, substituted nitrogen, oxygen, and sulfur;

when $R^4$ and $R^5$ together with the nitrogen to which they are attached form a ring, the said ring is optionally substituted by 1 to 3 groups selected from OH, $OR^4$, $NR^4R^5$, ($CH_2$)$_m$$OR^4$, ($CH_2$)$_m$$NR^4R^5$, T—($CH_2$)$_m$$QR^4$, CO—T—($CH_2$)$_m$$QR^4$, NH(CO)T($CH_2$)$_m$$QR^4$, T—($CH_2$)$_m$$CO_2R^4$, or T($CH_2$)$_m$$CONR^4R^5$;

$R^6$ is alkyl;
$R^8$ and $R^9$ independently are H, $C_1$-$C_3$ alkyl, $NR^4R^5$, $N(O)R^4R^5$, $NR^4R^5R^6Y$, hydroxy, alkoxy, thiol, thioalkyl, halo, $COR^4$, $CONR^4R^5$, $SO_2NR^4R^5$, $SO_3R^4$, $PO_3R^4$, CHO, CN, or $NO_2$;

when the dotted line is absent, $R^9$ is additionally carbonyl, thiocarbonyl, imine and substituted imine, oxime and oxime ether, and
Y is a halo counter-ion.

An especially preferred group of compounds have the above formula wherein X is O.

Another preferred group of compounds are those wherein W is NH.

A preferred group of compounds of Formula I have the above formula wherein X is O or $NHR^{10}$, and $R^3$ is H or substituted aryl.

Also preferred are compounds of Formula I wherein $R^8$ and $R^9$ both are hydrogen.

Another preferred group of compounds of Formula I have the above formula wherein X is O, and $R^2$ is Et, Pr, i-Pr, i-Bu, i-pentyl, or cycloalkyl. In an especially preferred group of compounds, X is O and $R^2$ is cyclopentyl or ethyl.

In yet another preferred group of compounds of Formula I, X is O, W is NH, and $R^1$ is alkyl, substituted alkyl, phenyl, or substituted phenyl, pyridyl or substituted pyridyl. Preferred $R^1$ substituted phenyl groups include 4-piperidinyl (with or without substitution), 4-(2-diethylaminoethoxy), 4-pyrrole, 4-pyrazol, and 4-(4-methyl piperazin-1-yl). In an especially preferred group of compounds, X is O, and $R^1$ is phenyl substituted with hydroxy, alkoxy, $NR^4R^5$, or $T(CH_2)_mQR^4$, where $R^4$ and $R^5$, T, m, and Q all are as defined above. In an even more preferred group of compounds, X is O, and $R^1$ is phenyl substituted with $NR^4R^5$ or $T(CH_2)_mQR^4$, where $R^4$ and $R^5$, T, m, and Q all are as defined above.

Another preferred group of compounds of Formula I are those wherein X is NH.

Further preferred compounds are the pyrimido[4,5-d]pyrimidines of Formula I wherein Z is N.

Especially preferred compounds provided by the invention have Formulas II, III, and IV

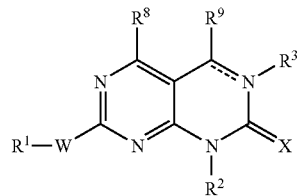

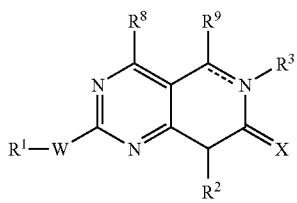

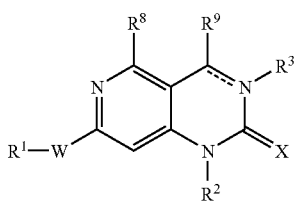

wherein $R^1$, $R^2$, $R^3$, W, $R^8$, $R^9$, and X are as defined above.

Additionally preferred compounds have the above formulas wherein W is NH. Also preferred are those compounds wherein $R^1$ is alkyl, substituted phenyl or pyridyl.

Further preferred compounds of the present invention have the Formula V:

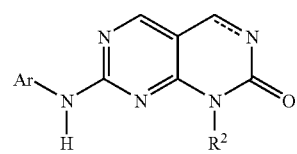

where R² is as defined above, and Ar is phenyl, substituted phenyl, or heteroaryl. Ideally, R² is alkyl such as ethyl, isopropyl, propyl, butyl, or isopentyl, or cycloalkyl such as norbornyl, cyclopentyl, cyclohexyl, or adamantyl. A most preferred Ar group is phenyl, preferably substituted with 1, 2, or 3 groups selected from phenyl, chloro, bromo, methyl, methoxy, hydroxy, hydroxymethyl, 2-diethylaminoethoxy, methoxycarbonylmethyl, carboxy, carboxymethyl, ethoxycarbonyl, 2-carboxyethyl, 2-ethoxycarbonylethyl, NR⁴R⁵, and O(CH₂)₀₋₆NR⁴R⁵, wherein R⁴ and R⁵ are as defined above. Another preferred Ar group is pyridyl and thiazolyl, for example, 3-pyridyl, 2-thiazolyl, each optionally substituted by alkyl, halo, phenyl, hydroxyphenyl, or alkoxyphenyl.

Other preferred compounds have Formula VI

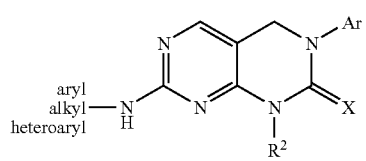

VI where alkyl, Ar, aryl, heteroaryl, R², and X are as defined above. Particularly preferred compounds of Formula VI are those where X is O or NHCOR⁴, for example, NHCO alkyl and NHCONH alkyl. Preferred aryl groups are phenyl and substituted phenyl. Preferred heteroaryl groups are pyridyl and substituted pyridyl.

Compounds of Formula I wherein W is S, SO, or SO₂ are especially useful as intermediates leading to compounds where W is NH, but such compounds also display inhibitory activity against cyclin-dependent kinases and tyrosine kinases.

Unless otherwise expressly stated, the following definitions are adhered to throughout this disclosure.

"Alkyl" means a straight or branched hydrocarbon radical having from 1 to 10 carbon atoms (unless stated otherwise) and includes, for example, methyl, ethyl, n-propyl, isopropyl, n-butyl, sec-butyl, isobutyl, tert-butyl, n-pentyl, isopentyl, n-hexyl, and the like.

"Halo" includes fluoro, chloro, bromo, and iodo.

"Alkenyl" means straight and branched hydrocarbon radicals having from 2 to 10 carbon atoms and one or two double bonds and includes ethenyl, 3-buten-1-yl, 2-ethenylbutyl, 3-hexen-1-yl, 3,6-octadien-1-yl, and the like.

"Alkynyl" means straight and branched hydrocarbon radicals having from 2 to 10 carbon atoms and one or two triple bonds and includes ethynyl, 3-butyn-1-yl, propynyl, 2-butyn-1-yl, 3-pentyn-1-yl, 3,6-octadien-1-yl, and the like.

"Cycloalkyl" means a monocyclic or polycyclic hydrocarbyl group such as cyclopropyl, cycloheptyl, cyclooctyl, cyclodecyl, cyclobutyl, adamantyl, norpinanyl, decalinyl, norbornyl, cyclohexyl, and cyclopentyl. Such groups can be substituted with groups such as hydroxy, keto, and the like. Also included are rings in which 1 to 3 heteroatoms replace carbons. Such groups are termed "heterocyclyl", which means a cycloalkyl group also bearing at least one heteroatom selected from O, S, or NR₂, examples being oxiranyl, pyrrolidinyl, piperidyl, tetrahydropyran, and morpholine.

"Alkoxy" refers to the alkyl groups mentioned above bound through oxygen, examples of which include methoxy, ethoxy, isopropoxy, tert-butoxy, and the like. In addition, alkoxy refers to polyethers such as —O—(CH₂)₂—O—OH₃, and the like.

"Alkanoyl" groups are alkyl linked through a carbonyl, i.e., C₁-C₉-C(O)—. Such groups include formyl, acetyl, propionyl, butyryl, and isobutyryl.

"Acyl" means an alkyl or aryl (Ar) group bonded through a carbonyl group, ie, R—C(O)—. For example, acyl includes a C₁-C₁₀ alkanoyl, including substituted alkanoyl, wherein the alkyl portion can be substituted by NR⁴R⁵ or a carboxylic or heterocyclic group. Typical acyl groups include acetyl, benzoyl, and the like.

The alkyl, alkenyl, alkoxy, and alkynyl groups described above are optionally substituted, preferably by 1 to 3 groups selected from NR⁴R⁵, N(O)R⁴R⁵, NR⁴R⁵R⁶Y, phenyl, substituted phenyl, thio C₁-C₁₀ alkyl, C₁-C₁₀ alkoxy, hydroxy, carboxy, C₁-C₁₀ alkoxycarbonyl, halo, nitrile, cycloalkyl, and a 5- or 6-membered carbocyclic ring or heterocyclic ring having 1 or 2 heteroatoms selected from nitrogen, substituted nitrogen, oxygen, and sulfur. "Substituted nitrogen" means nitrogen bearing C₁-C₁₀ alkyl or (CH₂)ₙPh where n is 0, 1, 2, or 3. Perhalo and polyhalo substitution is also embraced.

Examples of substituted alkyl groups include 2-aminoethyl, pentachloroethyl, trifluoromethyl, 2-diethylaminoethyl, 2-dimethylaminopropyl, ethoxycarbonylmethyl, 3-phenylbutyl, methanylsulfanylmethyl, methoxymethyl, 3-hydroxypentyl, 2-carboxybutyl, 4-chlorobutyl, 3-cyclopropylpropyl, pentafluoroethyl, 3-morpholinopropyl, piperazinylmethyl, and 2-(4-methylpiperazinyl)ethyl.

Examples of substituted alkynyl groups include 2-methoxyethynyl, 2-ethylsulfanyethynyl, 4-(1-piperazinyl)-3-(butynyl), 3-phenyl-5-hexynyl, 3-diethylamino-3-butynyl, 4-chloro-3-butynyl, 4-cyclobutyl-4-hexenyl, and the like.

Typical substituted alkoxy groups include 2-aminoethoxy, trifluoromethoxy, 2-diethylaminoethoxy, 2-ethoxycarbonylethoxy, 3-hydroxypropoxy, 6-carboxhexyloxy, and the like.

Further examples of substituted alkyl, alkenyl, and alkynyl groups include dimethylaminomethyl, carboxymethyl, 4-dimethylamino-3-buten-1-yl, 5-ethylmethylamino-3-pentyn-1-yl, 4-morpholinobutyl, 4-tetrahydropyrimidylbutyl, 3-imidazolidin-1-ylpropyl, 4-tetrahydrothiazol-3-yl-butyl, phenylmethyl, 3-chlorophenylmethyl, and the like.

The terms "Ar" and "aryl" refer to unsubstituted and substituted aromatic groups. Heteroaryl groups have from 4 to 9 ring atoms, from 1 to 4 of which are independently selected from the group consisting of O, S, and N. Preferred heteroaryl groups have 1 or 2 heteroatoms in a 5- or 6-membered aromatic ring. Mono and bicyclic aromatic ring systems are included in the definition of aryl and heteroaryl. Typical aryl and heteroaryl groups include phenyl, 3-chlorophenyl, 2,6-dibromophenyl, 2-pyridyl, 3-methyl-2-pyridyl, 3-benzothienyl, 2,4,6-tribromophenyl, 4-ethyl-2-benzothienyl, 2-furanyl, 3,4-diethyl-2-furanyl, 1-naphthyl, 4,7-dichloro-2-naphthyl, pyrrole, pyrazole, imidazole, thiazole, and the like. An especially preferred heteroaryl group is pyridyl.

Preferred Ar groups are phenyl and phenyl substituted by 1, 2, or 3 groups independently selected from the group consisting of alkyl, alkoxy, thio, thioalkyl, hydroxy, —COOR⁷, amino of the formula —NR⁴R⁵, CONR⁴R⁵, and T(CH₂)ₘQR⁴ or T(CH₂)ₘCO₂R⁴ wherein m is 1 to 6, T is O, S, NR⁴, N(O)R⁴, NR⁴R⁶Y, or CR⁴R⁵, Q is O, S, NR⁵, N(O)R⁵, or NR⁵R⁶Y wherein R⁴ and R⁵ are as described above, and R⁷ is H, alkyl or substituted alkyl, for example, methyl, 2-aminoethyl, trichloroethyl, diphenylmethyl, and the like. The alkyl and alkoxy groups can be substituted as defined above. For example, typical groups are carboxyalkyl, alkoxycarbonylalkyl, hydroxyalkyl, hydroxyalkoxy, and alkoxyalkyl.

The invention compound will be named herein according to the following position assignments

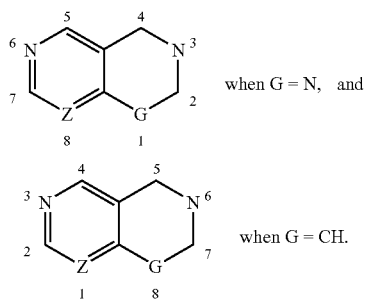

when G = N, and when G = CH.

It will be appreciated by those skilled in the art that the compounds defined by the above formula can exist in tantomeric forms. For example, a 2-keto compound can tantomerize to a 2-enol when $R^2$ is hydrogen as follows:

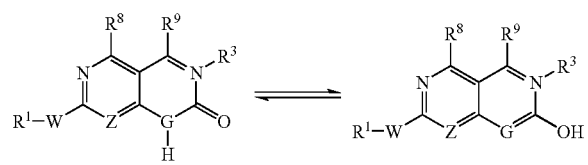

Similarly, 2-imino compounds can tantomerize to 2-amino compounds as follows:

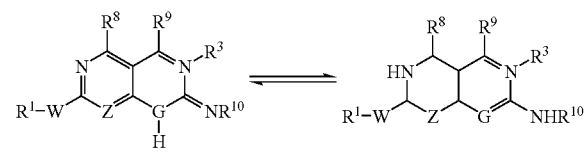

2-Thiones can tantomerize to thiols as follows:

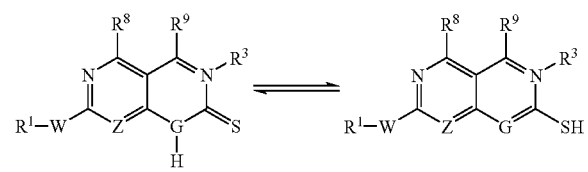

All of the tantomeric forms of compounds of Formulas I-IV are contemplated and included within the scope of this invention.

The compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of Formula I are capable of further forming both pharmaceutically acceptable formulations comprising salts, including but not limited to acid addition and/or base salts, solvates and N-oxides. This invention also provides pharmaceutical formulations comprising a compound of Formula I together with a pharmaceutically acceptable carrier, diluent, or excipient therefor. All of these forms are within the present invention.

Pharmaceutically acceptable acid addition salts of the compounds of Formula I include salts derived form inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate, gluconate, galacturonate, and the like; see, for example, Berge, et al., "Pharmaceutical Salts," *J. of Pharmaceutical Science,* 1977; 66:1-19.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine; see, for example, Berge, et al., supra.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

The compounds of the present invention are useful for treating cancer (for example, leukemia and cancer of the lung, breast, prostate, and skin such as melanoma) and other proliferative diseases including but not limited to psoriasis, HSV, HIV, restenosis, and atherosclerosis. To utilize a compound of the present invention to treat cancer, a patient having cancer is administered a therapeutically effective amount of a pharmaceutically acceptable composition comprising an invention compound.

A further embodiment of this invention is a method of treating subjects suffering from diseases caused by vascular smooth muscle cell proliferation. Compounds within the scope of the present invention effectively inhibit vascular smooth muscle cell proliferation and migration. The method entails inhibiting vascular smooth muscle proliferation, and/or migration by administering an effective amount of a compound of Formula I to a subject in need of treatment.

The compounds of the present invention can be formulated and administered in a wide variety of oral and parenteral dosage forms, including transdermal and rectal administration. It will be recognized to those skilled in the art that the following dosage forms may comprise as the active component, a compound of Formula I or a corresponding pharmaceutically acceptable salt or solvate thereof.

A further embodiment of this invention is a pharmaceutical formulation comprising a compound of Formula I together with a pharmaceutically acceptable carrier, diluent, or excipient therefor. For preparing pharmaceutical compositions with the compounds of the present invention, pharmaceutically acceptable carriers can be either a solid or liquid. Solid form preparations include powders, tablets, pills, capsules, cachets, suppositories, and dispensible granules. A solid carrier can be one or more substances which may also act as diluents, flavoring agents, binders, preservatives, tablet disintegrating agents, or an encapsulating material.

In powders, the carrier is a finely divided solid such as talc or starch which is in a mixture with the finely divided active component. In tablets, the active component is mixed with the carrier having the necessary binding properties in suitable proportions and compacted in the shape and size desired.

The formulations of this invention preferably contain from about 5% to about 70% or more of the active compound. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. A preferred form for oral use are capsules, which include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogenously therein, as by stirring. The molten homogenous mixture is then poured into convenient size molds, allowed to cool, and thereby to solidify.

Liquid form preparations include solutions, suspensions, and emulsions such as water or water/propylene glycol solutions. For parenteral injection, liquid preparations can be formulated in solution in aqueous polyethylene glycol solution, isotonic saline, 5% aqueous glucose, and the like. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water and mixing with a viscous material, such as natural or synthetic gums, resins, methylcellulose, sodium carboxymethylcellulose, or other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like. Waxes, polymers, microparticles, and the like can be utilized to prepare sustained-release dosage forms. Also, osmotic pumps can be employed to deliver the active compound uniformally over a prolonged period.

The pharmaceutical preparations of the invention are preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form.

The therapeutically effective dose of a compound of Formula I and/or Formula II will generally be from about 1 mg to about 100 mg/kg of body weight per day. Typical adult doses will be about 50 mg to about 800 mg per day. The quantity of active component in a unit dose preparation may be varied or adjusted from about 0.1 mg to about 500 mg, preferably about 0.5 mg to 100 mg according to the particular application and the potency of the active component. The composition can, if desired, also contain other compatible therapeutic agents. A subject in need of treatment with a compound of Formula I and/or II is administered a dosage of about 1 to about 500 mg per day, either singly or in multiple doses over a 24-hour period.

The compounds of the present invention are capable of binding to and inhibiting the activity of proteins having the ability to phosphorylate other proteins, such as cdks, PDGFr, FGFr, c-Src, and EGFr-FL. Cdks form complexes with cyclins, and these complexes phosphorylate key proteins allowing cells to proceed through the cell cycle (Meijer L., *Progress in Cell Cycle Research,* 1995; 1:351-363). The compounds of this invention inhibit this phosphorylation and therefore can be used as anti-proliferative agents for the treatment of cancer and/or restenosis and other proliferative diseases.

Because of their inhibitory activity against cdks and other kinases, the compounds of the present invention are also useful research tools for studying the mechanism of action of those kinases, both in vitro and in vivo.

While the forms of the invention herein constitute presently preferred embodiments, many others are possible. It is not intended herein to mention all of the possible equivalent forms or ramifications of the invention. It is understood that the terms used herein are merely descriptive rather than limiting, and those skilled in the art will realize that various changes may be made without departing from the spirit or scope of the invention.

The following compounds illustrate specific embodiments provided by the present invention, and the compounds listed below are among the preferred embodiments.

1-Methyl-7-[4-(pyrazol-1-yl)phenylamino]-3,4-dihydro-pyrimido[4,5-d]pyrimidin-2(1H)-one;

1-Methyl-7-[4-(4-methylpiperazin-1-yl)phenylamino]-3,4-dihydro-pyrimido[4,5-d]pyrimidin-2(1H)-one;

1-Methyl-7-[4-(4-hydroxypiperidin-1-yl)phenylamino]-3,4-dihydro-pyrimido[4,5-d]pyrimidin-2(1H)-one;

1-Methyl-7-{4-[4-(dimethylamino)piperidin-1-yl]phenylamino}-3,4-dihydro-pyrimido[4,5-d]pyrimidin-2(1H)-one;

1-Isopropyl-7-[4-(pyrazol-1-yl)phenylamino]-3,4-dihydro-pyrimido[4,5-d]pyrimidin-2(1H)-one;

1-Isopropyl-7-[4-(4-methylpiperazin-1-yl)phenylamino]-3,4-dihydro-pyrimido[4,5-d]pyrimidin-2(1H)-one;

1-Isopropyl-7-[4-(4-hydroxypiperidin-1-yl)phenylamino]-3,4-dihydro-pyrimido[4,5-d]pyrimidin-2(1H)-one;

1-Isopropyl-7-{4-[4-(dimethylamino)piperidin-1-yl]phenylamino}-3,4-dihydro-pyrimido[4,5-d]pyrimidin-2(1H)-one;

1-Bicyclo[2.2.1]hept-2-yl-7-[4-(pyrazol-1-yl)phenylamino]-3,4-dihydro-pyrimido[4,5-d]pyrimidin-2(1H)-one (exo);

1-Bicyclo[2.2.1]hept-2-yl-7-[4-(4-methylpiperazin-1-yl)
phenylamino]-3,4-dihydro-pyrimido[4,5-d]pyrimidin-2
(1H)-one (exo);
1-Bicyclo[2.2.1]hept-2-yl-7-[4-(4-hydroxypiperidin-1-yl)
phenylamino]-3,4-dihydro-pyrimido[4,5-d]pyrimidin-2
(1H)-one (exo);
1-Bicyclo[2.2.1]hept-2-yl-7-{4-[4-(dimethylamino)piperidin-1-yl]phenylamino}-3,4-dihydro-pyrimido[4,5-d]pyrimidin-2(1H)-one (exo);
7-[4-(4-Aminoacetyl-piperazin-1-yl)-phenylamino]-1-cyclopentyl-3,4-dihydro-pyrimido[4,5-d]pyrimidin-2(1H)-one;
7-{4-[4-(2-Amino-4-methyl-pentanoyl)-piperazin-1-yl]-phenylamino}-1-cyclopentyl-3,4-dihydro-pyrimido[4,5-d]pyrimidin-2(1H)-one;
1-Methyl-7-{4-[4-(3-morpholin-4-ylpropyl)piperidin-1-yl]phenylamino}-3,4-dihydro-pyrimido[4,5-d]pyrimidin-2(1H)-one;
1-Isopropyl-7-{4-[4-(3-morpholin-4-ylpropyl)piperidin-1-yl]phenylamino}-3,4-dihydro-pyrimido[4,5-d]pyrimidin-2(1H)-one;
1-Cyclopentyl-7-{4-[4-(3-morpholin-4-ylpropyl)piperidin-1-yl]phenylamino}-3,4-dihydro-pyrimido[4,5-d]pyrimidin-2(1H)-one;
1-Bicyclo[2.2.1]hept-2-yl-7-{4-[4-(3-morpholin-4-ylpropyl)piperidin-1-yl]phenylamino}-3,4-dihydro-pyrimido[4,5-d]pyrimidin-2(1H)-one (exo);
1-Cyclopentyl-7-(pyridin-4-ylamino)-3,4-dihydro-pyrimido[4,5-d]pyrimidin-2(1H)-one;
1-Cyclopentyl-7-(4-methanesulfonyl-phenylamino)-3,4-dihydro-pyrimido[4,5-d]pyrimidin-2(1H)-one;
1-Cyclopentyl-7-(4-fluoro-3-methyl-phenylamino)-3,4-dihydro-pyrimido[4,5-d]pyrimidin-2(1H)-one;
7-[4-(3-Amino-pyrrolidin-1-yl)-phenylamino]-1-cyclopentyl-3,4-dihydro-pyrimido[4,5-d]pyrimidin-2(1H)-one;
7-[4-(4-Acetyl-piperazin-1-yl)-phenylamino]-1-cyclopentyl-3,4-dihydro-pyrimido[4,5-d]pyrimidin-2(1H)-one;
1-Cyclopentyl-7-(4-piperazin-1-yl-phenylamino)-3,4-dihydro-pyrimido[4,5-d]pyrimidin-2(1H)-one;
1-Cyclopentyl-7-[4-(5-methyl-hexahydro-pyrrolo[3,4-c]pyrrol-2-yl)-phenylamino]-3,4-dihydro-pyrimido[4,5-d]pyrimidin-2(1H)-one;
7-[4-(4-Aminoacetyl-piperazin-1-yl)-phenylamino]-3-(3,5-dimethoxy-phenyl)-1-ethyl-3,4-dihydro-pyrimido[4,5-d]pyrimidin-2(1H)-one;
7-[4-(4-Aminoacetyl-piperazin-1-yl)-phenylamino]-3-(2-chloro-3,5-dimethoxy-phenyl)-1-ethyl-3,4-dihydro-pyrimido[4,5-d]pyrimidin-2(1H)-one;
7-[4-(4-Aminoacetyl-piperazin-1-yl)-phenylamino]-3-(2,6-dichloro-3,5-dimethoxy-phenyl)-1-ethyl-3,4-dihydro-pyrimido[4,5-d]pyrimidin-2(1H)-one;
7-[4-(4-Aminoacetyl-piperazin-1-yl)-phenylamino]-3-(2-methyl-3,5-dimethoxy-phenyl)-1-ethyl-3,4-dihydro-pyrimido[4,5-d]pyrimidin-2(1H)-one;
7-[4-(4-Aminoacetyl-piperazin-1-yl)-phenylamino]-3-(2,6-dimethyl-3,5-dimethoxy-phenyl)-1-ethyl-3,4-dihydro-pyrimido[4,5-d]pyrimidin-2(1H)-one;
7-[4-(2-Diethylamino-ethoxy)-phenylamino]-3-(3,5-dimethoxy-phenyl)-1-ethyl-3,4-dihydro-pyrimido[4,5-d]pyrimidin-2(1H)-one;
7-[4-(2-Diethylamino-ethoxy)-phenylamino]-3-(2-chloro-3,5-dimethoxy-phenyl)-1-ethyl-3,4-dihydro-pyrimido[4,5-d]pyrimidin-2(1H)-one;
7-[4-(2-Diethylamino-ethoxy)-phenylamino]-3-(2,6-dichloro-3,5-dimethoxy-phenyl)-1-ethyl-3,4-dihydro-pyrimido[4,5-d]pyrimidin-2(1H)-one;
7-[4-(2-Diethylamino-ethoxy)-phenylamino]-3-(2-methyl-3,5-dimethoxy-phenyl)-1-ethyl-3,4-dihydro-pyrimido[4,5-d]pyrimidin-2(1H)-one;
7-[4-(2-Diethylamino-ethoxy)-phenylamino]-3-(2,6-dimethyl-3,5-dimethoxy-phenyl)-1-ethyl-3,4-dihydro-pyrimido[4,5-d]pyrimidin-2(1H)-one;
7-(4-Diethylamino-butylamino)-3-(3,5-dimethoxy-phenyl)-1-ethyl-3,4-dihydro-pyrimido[4,5-d]pyrimidin-2(1H)-one;
7-(4-Diethylamino-butylamino)-3-(2-chloro-3,5-dimethoxy-phenyl)-1-ethyl-3,4-dihydro-pyrimido[4,5-d]pyrimidin-2(1H)-one;
7-(4-Diethylamino-butylamino)-3-(2,6-dichloro-3,5-dimethoxy-phenyl)-1-ethyl-3,4-dihydro-pyrimido[4,5-d]pyrimidin-2(1H)-one;
7-(4-Diethylamino-butylamino)-3-(2-methyl-3,5-dimethoxy-phenyl)-1-ethyl-3,4-dihydro-pyrimido[4,5-d]pyrimidin-2(1H)-one;
7-(4-Diethylamino-butylamino)-3-(2,6-dimethyl-3,5-dimethoxy-phenyl)-1-ethyl-3,4-dihydro-pyrimido[4,5-d]pyrimidin-2(1H)-one;
7-(Pyridin-4-ylamino)-3-(3,5-dimethoxy-phenyl)-1-ethyl-3,4-dihydro-pyrimido[4,5-d]pyrimidin-2(1H)-one;
7-(Pyridin-4-ylamino)-3-(2-chloro-3,5-dimethoxy-phenyl)-1-ethyl-3,4-dihydro-pyrimido[4,5-d]pyrimidin-2(1H)-one;
7-(Pyridin-4-ylamino)-3-(2,6-dichloro-3,5-dimethoxy-phenyl)-1-ethyl-3,4-dihydro-pyrimido[4,5-d]pyrimidin-2(1H)-one;
7-(Pyridin-4-ylamino)-3-(2,6-dimethyl-3,5-dimethoxy-phenyl)-1-ethyl-3,4-dihydro-pyrimido[4,5-d]pyrimidin-2(1H)-one;
7-(Pyridin-4-ylamino)-3-(2-methyl-3,5-dimethoxy-phenyl)-1-ethyl-3,4-dihydro-pyrimido[4,5-d]pyrimidin-2(1H)-one;
7-(Pyridin-4-ylamino)-3-(2,6-dichloro-3,5-dimethoxy-phenyl)-1-cyclopentyl-3,4-dihydro-pyrimido[4,5-d]pyrimidin-2(1H)-one;
3-(2-Chloro-3,5-dimethoxy-phenyl)-7-(4-diethylamino-butylamino)-3,4-dihydro-pyrimido[4,5-d]pyrimidin-2(1H)-one;
3-(2-Chloro-3,5-dimethoxy-phenyl)-7-[4-(2-diethylamino-ethoxy)-phenylamino]-3,4-dihydro-pyrimido[4,5-d]pyrimidin-2(1H)-one;
3-(2-Chloro-3,5-dimethoxy-phenyl)-7-(pyridin-4-ylamino)-3,4-dihydro-pyrimido[4,5-d]pyrimidin-2(1H)-one;
3-(3,5-Dimethoxy-phenyl)-7-(pyridin-4-ylamino)-3,4-dihydro-pyrimido[4,5-d]pyrimidin-2(1H)-one;
7-[4-(2-Diethylamino-ethoxy)-phenylamino]-3-(3,5-dimethoxy-phenyl)-3,4-dihydro-pyrimido [4,5-d]pyrimidin-2(1H)-one;
3-(2,6-Dichloro-3,5-dimethoxy-phenyl)-7-(pyridin-4-ylamino)-3,4-dihydro-pyrimido[4,5-d]pyrimidin-2(1H)-one;
3-(2,6-Dichloro-3,5-dimethoxy-phenyl)-7-[4-(2-diethylamino-ethoxy)-phenylamino]-3,4-dihydro-pyrimido[4,5-d]pyrimidin-2(1H)-one;
7-[3-(Carboxy)-phenylamino]-3-(2,6-dichloro-phenyl)-1-methyl-3,4-dihydro-pyrimido[4,5-d]pyrimidin-2(1H)-one;
7-[3-(N-Dimethylaminopropyl-carboxamide)-phenylamino]-3-(2,6-dichloro-phenyl)-1-methyl-3,4-dihydro-pyrimido[4,5-d]pyrimidin-2(1H)-one;
7-[3-(N-Dimethylaminopropyl-carboxamide)-phenylamino]-3-(2,6-dichloro-3-hydroxy-phenyl)-1-methyl-3,4-dihydro-pyrimido[4,5-d]pyrimidin-2(1H)-one;

7-[3-(Carboxy)-phenylamino]-3-(2,6-dichloro-3-hydroxy-phenyl)-1-methyl-3,4-dihydro-pyrimido[4,5-d]pyrimidin-2(1H)-one;

3-(2,6-Dichloro-phenyl)-7-[4-(2-ethylamino-ethoxy)-phenylamino]-1-methyl-3,4-dihydro-pyrimido[4,5-d]pyrimidin-2(1H)-one;

3-(2,6-Dichloro-3-hydroxy-phenyl)-7-[4-(2-ethylamino-ethoxy)-phenylamino]-1-methyl-3,4-dihydro-pyrimido[4,5-d]pyrimidin-2(1H)-one;

7-[4-(Carboxamide)-phenylamino]-3-(2,6-dichloro-phenyl)-1-methyl-3,4-dihydro-pyrimido[4,5-d]pyrimidin-2(1H)-one;

7-[4-(Carboxamide)-phenylamino]-3-(2,6-dichloro-3-hydroxy-phenyl)-1-methyl-3,4-dihydro-pyrimido[4,5-d]pyrimidin-2(1H)-one;

3-(2,6-Dichloro-phenyl)-7-(3-hydroxymethyl-phenylamino)-1-methyl-3,4-dihydro-pyrimido [4,5-d]pyrimidin-2(1H)-one;

3-(2,6-Dichloro-phenyl)-7-(4-morpholin-4-yl-phenylamino)-3,4-dihydro-pyrimido[4,5-d]pyrimidin-2(1H)-one;

3-(2,6-Dichloro-3-hydroxy-phenyl)-1-methyl-7-(4-morpholin-4-yl-phenylamino)-3,4-dihydro-pyrimido[4,5-d]pyrimidin-2(1H)-one;

3-(2,6-Dichloro-3-hydroxy-phenyl)-7-(3-hydroxymethyl-phenylamino)-1-methyl-3,4-dihydro-pyrimido[4,5-d]pyrimidin-2(1H)-one;

7-[4-(3-Carboxypropyl)-phenylamino]-3-(2,6-dichloro-phenyl)-1-methyl-3,4-dihydro-pyrimido[4,5-d]pyrimidin-2(1H)-one;

7-[4-(3-Carboxypropyl)-phenylamino]-3-(2,6-dichloro-3-hydroxy-phenyl)-1-methyl-3,4-dihydro-pyrimido[4,5-d]pyrimidin-2(1H)-one;

3-(2,6-Dichloro-phenyl)-7-[4-(formyl-phenylamino]-1-methyl-3,4-dihydro-pyrimido[4,5-d]pyrimidin-2(1H)-one;

3-(2,6-Dichloro-3-hydroxy-phenyl)-7-[4-(formyl-phenylamino]-1-methyl-3,4-dihydro-pyrimido[4,5-d]pyrimidin-2(1H)-one;

1-Methyl-7-[4-(pyrazol-1-yl)phenylamino]pyrimido[4,5-d]pyrimidin-2(1H)-one;

1-Methyl-7-[4-(4-methylpiperazin-1-yl)phenylamino]pyrimido[4,5-d]pyrimidin-2(1H)-one;

1-Methyl-7-[4-(4-hydroxypiperidin-1-yl)phenylamino]pyrimido[4,5-d]pyrimidin-2(1H)-one;

1-Methyl-7-{4-[4-(dimethylamino)piperidin-1-yl]phenylamino}-pyrimido[4,5-d]pyrimidin-2(1H)-one;

1-Isopropyl-7-[4-(pyrazol-1-yl)phenylamino]pyrimido[4,5-d]pyrimidin-2(1H)-one;

1-Isopropyl-7-[4-(4-methylpiperazin-1-yl)phenylamino]pyrimido[4,5-d]pyrimidin-2(1H)-one;

1-Isopropyl-7-[4-(4-hydroxypiperidin-1-yl)phenylamino]pyrimido[4,5-d]pyrimidin-2(1H)-one;

1-Isopropyl-7-{4-[4-(dimethylamino)piperidin-1-yl]phenylamino}-pyrimido[4,5-d]pyrimidin-2(1H)-one;

1-Bicyclo[2.2.1]hept-2-yl-7-[4-(pyrazol-1-yl)phenylamino]pyrimido[4,5-d]pyrimidin-2(1H)-one (exo);

1-Bicyclo[2.2.1]hept-2-yl-7-[4-(4-methylpiperazin-1-yl)phenylamino]pyrimido[4,5-d]pyrimidin-2(1H)-one (exo);

1-Bicyclo[2.2.1]hept-2-yl-7-[4-(4-hydroxypiperidin-1-yl)phenylamino]pyrimido[4,5-d]pyrimidin-2(1H)-one (exo);

1-Bicyclo[2.2.1]hept-2-yl-7-{4-[4-(dimethylamino)piperidin-1-yl]phenylamino}pyrimido[4,5-d]pyrimidin-2(1H)-one (exo);

7-[4-(4-Aminoacetyl-piperazin-1-yl)-phenylamino]-1-cyclopentyl-pyrimido[4,5-d]pyrimidin-2(1H)-one;

7-{4-[4-(2-Amino-4-methyl-pentanoyl)-piperazin-1-yl]-phenylamino}-1-cyclopentyl-pyrimido[4,5-d]pyrimidin-2(1H)-one;

1-Methyl-7-{4-[4-(3-morpholin-4-ylpropyl)piperidin-1-yl]phenylamino}pyrimido[4,5-d]pyrimidin-2(1H)-one;

1-Isopropyl-7-{4-[4-(3-morpholin-4-ylpropyl)piperidin-1-yl]phenylamino}pyrimido[4,5-d]pyrimidin-2(1H)-one;

1-Cyclopentyl-7-{4-[4-(3-morpholin-4-ylpropyl)piperidin-1-yl]phenylamino}pyrimido[4,5-d]pyrimidin-2(1H)-one;

1-Bicyclo[2.2.1]hept-2-yl-7-{4-[4-(3-morpholin-4-ylpropyl)piperidin-1-yl]phenylamino}pyrimido[4,5-d]pyrimidin-2(1H)-one (exo);

1-Cyclopentyl-7-(4-methanesulfonyl-phenylamino)-pyrimido[4,5-d]pyrimidin-2(1H)-one;

1-Cyclopentyl-7-(4-fluoro-3-methyl-phenylamino)-pyrimido[4,5-d]pyrimidin-2(1H)-one;

7-[4-(3-Amino-pyrrolidin-1-yl)-phenylamino]-1-cyclopentyl-pyrimido[4,5-d]pyrimidin-2(1H)-one;

1-Cyclopentyl-7-(4-piperazin-1-yl-phenylamino)-pyrimido[4,5-d]pyrimidin-2(1H)-one;

1-Cyclopentyl-7-[4-(5-methyl-hexahydro-pyrrolo[3,4-c]pyrrol-2-yl)-phenylamino]-pyrimido[4,5-d]pyrimidin-2(1H)-one;

7-[4-(4-Acetyl-piperazin-1-yl)-phenylamino]-1-cycloheptyl-pyrimido[4,5-d]pyrimidin-2(1H)-one;

1-Cyclopentyl-7-(pyridin-4-ylamino)pyrimido[4,5-d]pyrimidin-2(1H)-one;

1-[7-(4-Fluoro-phenylamino)-pyrimido[4,5-d]pyrimidin-2-yl]-3-methyl-urea;

1-Isopropyl-3-(7-phenylamino-pyrimido[4,5-d]pyrimidin-2-yl)-urea;

1-{7-[4-(3-Aminomethyl-pyrrolidin-1-yl)-phenylamino]-pyrimido[4,5-d]pyrimidin-2-yl}-3-isopropyl-urea;

1-Isopropyl-3-[7-(4-piperazin-1-yl-phenylamino)-pyrimido[4,5-d]pyrimidin-2-yl]-urea;

1-{7-[4-(4-Acetyl-piperazin-1-yl)-phenylamino]-pyrimido[4,5-d]pyrimidin-2-yl}-3-isopropyl-urea;

N-{7-[4-(3-Amino-pyrrolidin-1-yl)-phenylamino]-pyrimido[4,5-d]pyrimidin-2-yl}-3-methyl-butyramide;

N-[7-(4-piperazin-1-yl-phenylamino)-pyrimido[4,5-d]pyrimidin-2-yl]-isobutyramide;

N-{7-[4-(4-Acetyl-piperazin-1-yl)-phenylamino]-pyrimido[4,5-d]pyrimidin-2-yl}-3-methyl-butyramide;

3-Methyl-N-[7-(pyridin-4-ylamino)-pyrimido[4,5-d]pyrimidin-2-yl]-butyramide;

1-Isopropyl-3-[7-(pyridin-4-ylamino)-pyrimido[4,5-d]pyrimidin-2-yl]-urea;

N-{7-[4-(3-Aminomethyl-pyrrolidin-1-yl)-phenylamino]-pyrimido[4,5-d]pyrimidin-2-yl}-3-methyl-butyramide;

3-Methyl-N-{7-[4-(5-methyl-hexahydro-pyrrolo[3,4-c]pyrrol-2-yl)-phenylamino]-3,4-dihydro-pyrimido[4,5-d]pyrimidin-2-yl}-butyramide;

1-{7-[4-(4-Acetyl-piperazin-1-yl)-phenylamino]-3,4-dihydro-pyrimido[4,5-d]pyrimidin-2-yl}-3-isopropyl-urea;

1-[7-[4-(2-Diethylamino-ethoxy)-phenylamino]-3-(3,5-dimethoxy-phenyl)-3,4-dihydro-pyrimido[4,5-d]pyrimidin-2-yl]-3-ethyl-urea;

1-{3-(2-Chloro-3,5-dimethoxy-phenyl)-7-[4-(2-diethylamino-ethoxy)-phenylamino]-3,4-dihydro-pyrimido[4,5-d]pyrimidin-2-yl}-3-ethyl-urea;

1-tert-Butyl-3-[7-[4-(2-diethylamino-ethoxy)-phenylamino]-3-(3,5-dimethoxy-phenyl)-3,4-dihydro-pyrimido[4,5-d]pyrimidin-2-yl]-urea;

1-tert-Butyl-3-{3-(2-chloro-3,5-dimethoxy-phenyl)-7-[4-(2-diethylamino-ethoxy)-phenylamino]-3,4-dihydro-pyrimido[4,5-d]pyrimidin-2-yl}-urea;

1-tert-Butyl-3-[3-(3,5-dimethoxy-phenyl)-7-(pyridin-4-ylamino)-3,4-dihydro-pyrimido[4,5-d]pyrimidin-2-yl]-urea;

1-[3-(3,5-Dimethoxy-phenyl)-7-(pyridin-4-ylamino)-3,4-dihydro-pyrimido[4,5-d]pyrimidin-2-yl]-3-ethyl-urea;

1-tert-Butyl-3-[3-(2-chloro-3,5-dimethoxy-phenyl)-7-(pyridin-4-ylamino)-3,4-dihydro-pyrimido[4,5-d]pyrimidin-2-yl]-urea;

1-[3-(2-Chloro-3,5-dimethoxy-phenyl)-7-(pyridin-4-ylamino)-3,4-dihydro-pyrimido[4,5-d]pyrimidin-2-yl]-3-ethyl-urea;

1-[3-(2-Chloro-3,5-dimethoxy-phenyl)-7-(4-diethylamino-butylamino)-3,4-dihydro-pyrimido[4,5-d]pyrimidin-2-yl]-3-ethyl-urea;

1-tert-Butyl-3-[3-(2-chloro-3,5-dimethoxy-phenyl)-7-(4-diethylamino-butylamino)-3,4-dihydro-pyrimido[4,5-d]pyrimidin-2-yl]-urea;

1-(2-Benzyloxyethyl)-7-[4-(4-methylpiperazin-1-yl)phenylamino]-3,4-dihydro-pyrido[4,3-d]pyrimidin-2(1H)-one;

1-(Thiophen-2-yl)-7-[4-(4-methylpiperazin-1-yl)phenylamino]-3,4-dihydro-pyrido[4,3-d]pyrimidin-2(1H)-one;

1-(Thiophen-2-ylmethyl)-7-[4-(4-methylpiperazin-1-yl)phenylamino]-3,4-dihydro-pyrido[4,3-d]pyrimidin-2(1H)-one;

1-(Tetrahydrofuran-2-yl)-7-[4-(4-methylpiperazin-1-yl)phenylamino]-3,4-dihydro-pyrido[4,3-d]pyrimidin-2(1H)-one;

1-(Hexa-2,4-diene-1-yl)-7-[4-(4-methylpiperazin-1-yl)phenylamino]-3,4-dihydro-pyrido[4,3-d]pyrimidin-2(1H)-one;

1-(Prop-2-yne-1-yl)-7-[4-(4-methylpiperazin-1-yl)phenylamino]-3,4-dihydro-pyrido[4,3-d]pyrimidin-2(1H)-one;

1-[3-(Dimethylamino)prop-1-yl]-7-[4-(4-methylpiperazin-1-yl)phenylamino]-3,4-dihydro-pyrido[4,3-d]pyrimidin-2(1H)-one;

1-(3-Hydroxyprop-1-yl)-7-[4-(4-methylpiperazin-1-yl)phenylamino]-3,4-dihydro-pyrido[4,3-d]pyrimidin-2(1H)-one;

1-(Pyridin-4-ylmethyl)-7-[4-(4-methylpiperazin-1-yl)phenylamino]-3,4-dihydro-pyrido[4,3-d]pyrimidin-2(1H)-one;

1-(3,5-Dimethylhept-1-yl)-7-[4-(4-methylpiperazin-1-yl)phenylamino]-3,4-dihydro-pyrido[4,3-d]pyrimidin-2(1H)-one;

3-(3,5-Dimethoxy-phenyl)-7-(pyridin-4-ylamino)-1-ethyl-3,4-dihydro-pyrido[4,3-d]pyrimidin-2(1H)-one;

3-(2-Chloro-3,5-Dimethoxy-phenyl)-7-(pyridin-4-ylamino)-1-ethyl-3,4-dihydro-pyrido[4,3-d]pyrimidin-2(1H)-one;

3-(2,6-Dichloro-3,5-Dimethoxy-phenyl)-7-(pyridin-4-ylamino)-1-ethyl-3,4-dihydro-pyrido[4,3-d]pyrimidin-2(1H)-one;

3-(2-Methyl-3,5-Dimethoxy-phenyl)-7-(pyridin-4-ylamino)-1-ethyl-3,4-dihydro-pyrido[4,3-d]pyrimidin-2(1H)-one;

3-(2,6-Dimethyl-3,5-Dimethoxy-phenyl)-7-(pyridin-4-ylamino)-1-ethyl-3,4-dihydro-pyrido[4,3-d]pyrimidin-2(1H)-one;

7-[4-(4-Aminoacetyl-piperazin-1-yl)-phenylamino]-3-(3,5-dimethoxy-phenyl)-1-ethyl-3,4-dihydro-pyrido[4,3-d]pyrimidin-2(1H)-one;

7-[4-(4-Aminoacetyl-piperazin-1-yl)-phenylamino]-3-(2-chloro-3,5-dimethoxy-phenyl)-1-ethyl-3,4-dihydro-pyrido[4,3-d]pyrimidin-2(1H)-one;

7-[4-(4-Aminoacetyl-piperazin-1-yl)-phenylamino]-3-(2,6-dichloro-3,5-dimethoxy-phenyl)-1-ethyl-3,4-dihydro-pyrido[4,3-d]pyrimidin-2(1H)-one;

7-[4-(4-Aminoacetyl-piperazin-1-yl)-phenylamino]-3-(2-methyl-3,5-dimethoxy-phenyl)-1-ethyl-3,4-dihydro-pyrido[4,3-d]pyrimidin-2(1H)-one;

7-[4-(4-Aminoacetyl-piperazin-1-yl)-phenylamino]-3-(2,6-dimethyl-3,5-dimethoxy-phenyl)-1-ethyl-3,4-dihydro-pyrido[4,3-d]pyrimidin-2(1H)-one;

1-(2-Benzyloxyethyl)-7-[4-(4-methylpiperazin-1-yl)phenylamino]pyrido[4,3-d]pyrimidin-2(1H)-one;

1-(Thiophen-2-yl)-7-[4-(4-methylpiperazin-1-yl)phenylamino]pyrido[4,3-d]pyrimidin-2(1H)-one;

1-(Thiophen-2-ylmethyl)-7-[4-(4-methylpiperazin-1-yl)phenylamino]pyrido[4,3-d]pyrimidin-2(1H)-one;

1-(Tetrahydrofuran-2-yl)-7-[4-(4-methylpiperazin-1-yl)phenylamino]pyrido[4,3-d]pyrimidin-2(1H)-one;

1-(Hexa-2,4-diene-1-yl)-7-[4-(4-methylpiperazin-1-yl)phenylamino]pyrido[4,3-d]pyrimidin-2(1H)-one;

1-(Prop-2-yne-1-yl)-7-[4-(4-methylpiperazin-1-yl)phenylamino]pyrido[4,3-d]pyrimidin-2(1H)-one;

1-[3-(Dimethylamino)prop-1-yl]-7-[4-(4-methylpiperazin-1-yl)phenylamino]pyrido[4,3-d]pyrimidin-2(1H)-one;

1-(3-Hydroxyprop-1-yl)-7-[4-(4-methylpiperazin-1-yl)phenylamino]pyrido[4,3-d]pyrimidin-2(1H)-one;

1-(Pyridin-4-ylmethyl)-7-[4-(4-methylpiperazin-1-yl)phenylamino]pyrido[4,3-d]pyrimidin-2(1H)-one;

1-(3,5-Dimethylhept-1-yl)-7-[4-(4-methylpiperazin-1-yl)phenylamino]pyrido[4,3-d]pyrimidin-2(1H)-one;

1-Cyclopentyl-7-(4-piperazin-1-ylphenylamino)pyrido[4,3-d]pyrimidin-2(1H)-one;

7-[4-(3-Aminopyrrolidin-1-yl)phenylamino]-1-cyclopentylpyrido[4,3-d]pyrimidin-2(1H)-one;

2-[4-(3-Amino-pyrrolidin-1-yl)-phenylamino]-8-isopropyl-8H-pyrido[4,3-d]pyrimidin-7-one;

8-Cyclopentyl-2-[4-(hexahydro-pyrrolo[3,4-c]pyrrol-2-yl)-phenylamino]-8H-pyrido[4,3-d]pyrimidin-7-one;

2-[4-(4-Acetyl-piperazin-1-yl)-phenylamino]-8-cyclopentyl-8H-pyrido[4,3-d]pyrimidin-7-one;

N-{2-[4-(4-Aminoacetyl-piperazin-1-yl)-phenylamino]-8-cyclopentyl-pyrido[4,3-d]pyrimidin-7-yl}-2,2-dimethyl-propionamide;

N-(2-{4-[4-(2-Amino-4-methyl-pentanoyl)-piperazin-1-yl]-phenylamino}-8-cyclopentyl-pyrido[4,3-d]pyrimidin-7-yl)-2,2-dimethyl-propionamide;

1-Isopropyl-7-[4-(4-methylpiperazin-1-yl)phenylamino]-1H-pyrimido[4,5-d]pyrimidine-2,4-dione;

7-[4-(2-Diethylaminoethoxy)phenylamino]-1-isopropyl-1H-pyrimido[4,5-d]pyrimidine-2,4-dione;

7-(4-Diethylamino-butylamino)-3-(3,5-dimethoxy-phenyl)-1-ethyl-1H-pyrimido[4,5-d]pyrimidine-2,4-dione;

7-[4-(2-Diethylamino-ethoxy)-phenylamino]-3-(3,5-dimethoxy-phenyl)-1-ethyl-1H-pyrimido[4,5-d]pyrimidine-2,4-dione; and 7-(Pyridin-4-ylamino)-3-(3,5-dimethoxy-phenyl)-1-ethyl-1H-pyrimido[4,5-d]pyrimidine-2,4-dione.

Compounds of Formula I wherein Z is N or CH may be prepared according to the syntheses outlined in Schemes 1-3. Although these schemes often indicate exact structures, those with ordinary skill in the art will appreciate that the methods apply widely to analogous compounds of Formula I, given appropriate consideration to protection and deprotection of reactive functional groups by methods standard to the art of organic chemistry. For example, hydroxy groups, in order to prevent unwanted side reactions, generally need to be converted to ethers or esters during chemical reactions at other sites in the molecule. The hydroxy protecting group is readily removed to provide the free hydroxy group. Amino groups and carboxylic acid groups are similarly derivatized to protect them against unwanted side reactions. Typical protecting groups and methods for attaching and cleaving them are described fully by Greene and Wuts in *Protective Groups in Organic Synthesis*, John Wiley and Sons, New York, (2nd Ed., 1991), and McOmie, *Protective Groups in Organic Chemistry*, Plenum Press, New York, 1973.

Scheme 1 describes a typical method for the preparation of the bicyclic pyrimidines and bicyclic 3,4-dihydropyrimidines of the invention. The synthesis begins with 4-chloro-2-(methylthio)-5-pyrimidinecarbonitrile or 4-chloro-6-(methylthio)-3-pyridinecarbonitrile, which are readily prepared from common reactants. Displacement of the 4-chloro group with an amine in a solvent such as tetrahydrofuran (THF) in the presence or absence of a tertiary amine such as triethylamine provides the corresponding 4-amino-2-(methylthio)-5-pyrimidinecarbonitrile or 4-amino-6-(methylthio)-3-pyridinecarbonitrile. The amine used can be anhydrous or in an aqueous solution, as with methyl or ethyl amine, or cyclopentylamine. The use of aqueous ammonium hydroxide provides the corresponding primary amine at position 4. Reduction of the cyano group with common reducing agents such as LAH, provides the corresponding aminomethyl analog. Cyclization is accomplished by reaction with an agent such as 1,1'-carbonyldiimidazole (CDI). Oxidation of the methylthio group with an oxidant such as an oxaziridine in a solvent such as chloroform at room temperature provides the methyl sulfoxide derivative. Displacement of the sulfoxide with an amine ($H_2NR^1$) results in formation of the corresponding 7-amino-3,4-dihydro-bicyclic pyrimidine. The temperature required for the displacement depends upon the amine used. Aromatic, secondary, and tertiary amines usually require higher temperatures than primary aliphatic or benzyl amines. When aromatic amines such as aniline are used, the reaction is usually run with the amine as the solvent at high temperatures (e.g., 80-150° C.).

The bicyclic 3,4-dihydropyrimidines are readily oxidized by reaction with oxidants such as potassium tert-butoxide and oxygen to provide the corresponding bicyclic pyrimidines of the invention.

SCHEME 1

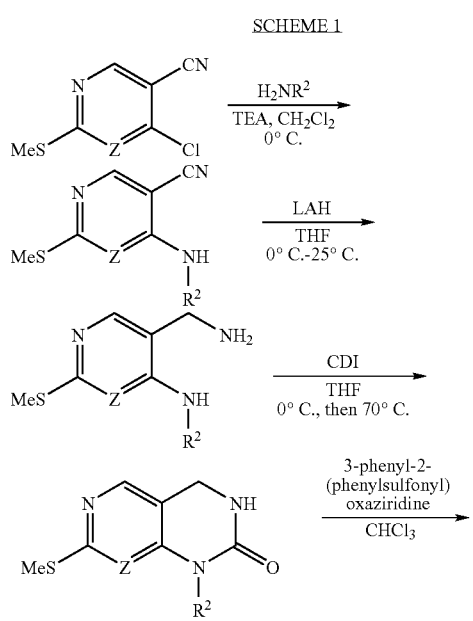

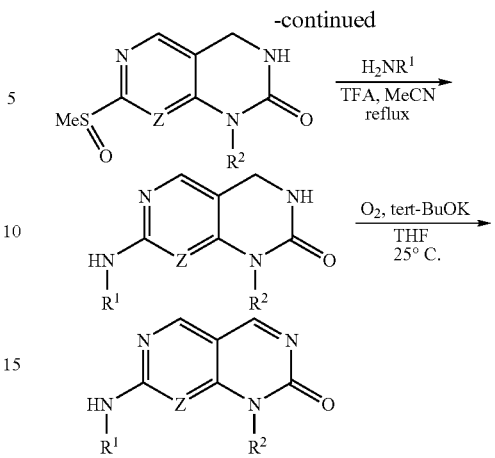

Scheme 1a describes a typical method for preparing bicyclic pyrimidines of Formula I wherein $R^2$ is H and X is $NHR^{10}$. A suitably substituted 2-methylthio-5-aminomethyl-4-amino-pyrimidine is first reacted with cyanogen bromide to effect cyclization to a dihydropyrimido pyrimidine. The methylthio group is oxidized to the sulfoxide by reaction with an oxidant such as an oxaziridine or a perbenzoic acid. The methylsulfoxide moiety is readily displaced by reaction with an amine ($R^1NH_2$) to provide a 7-amino-3,4-dihydro bicyclic pyrimidine having an amino group at the 2-position. These dihydro pyrimidines are easily converted to the corresponding aromatic pyrimidines by oxidation with common oxidants such as postossium tert-butoxide and oxygen. The 2-amino dihydropyrimidines and 2-amino pyrimidines are valuable biological agents, and also serve as intermediates, wherein the 2-amino group is derivatized by standard methods, for example alkylation or acylation, to provide compounds of Formula I where X is $NR^{10}$, e.g.,

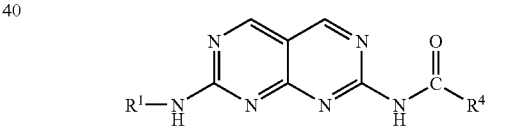

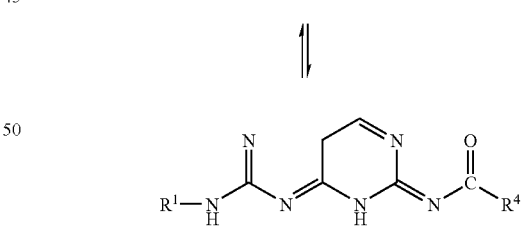

Scheme 1a

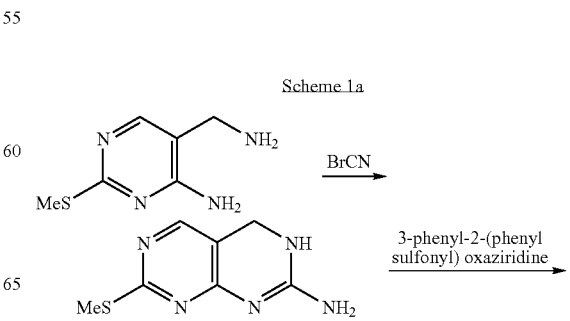

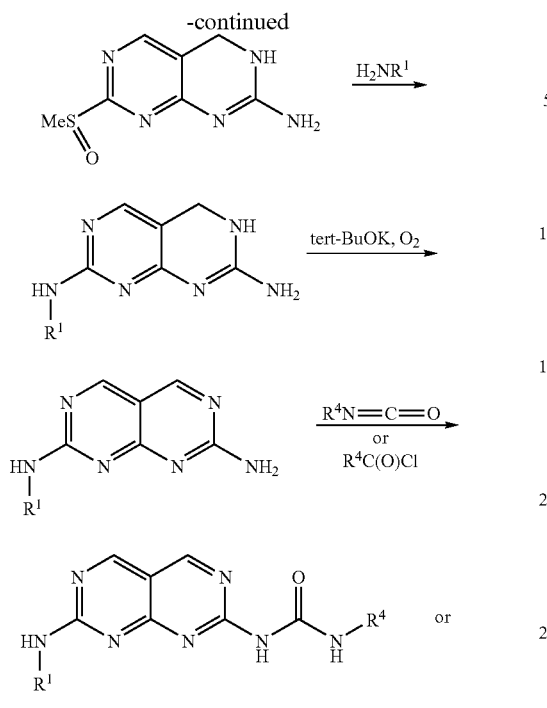

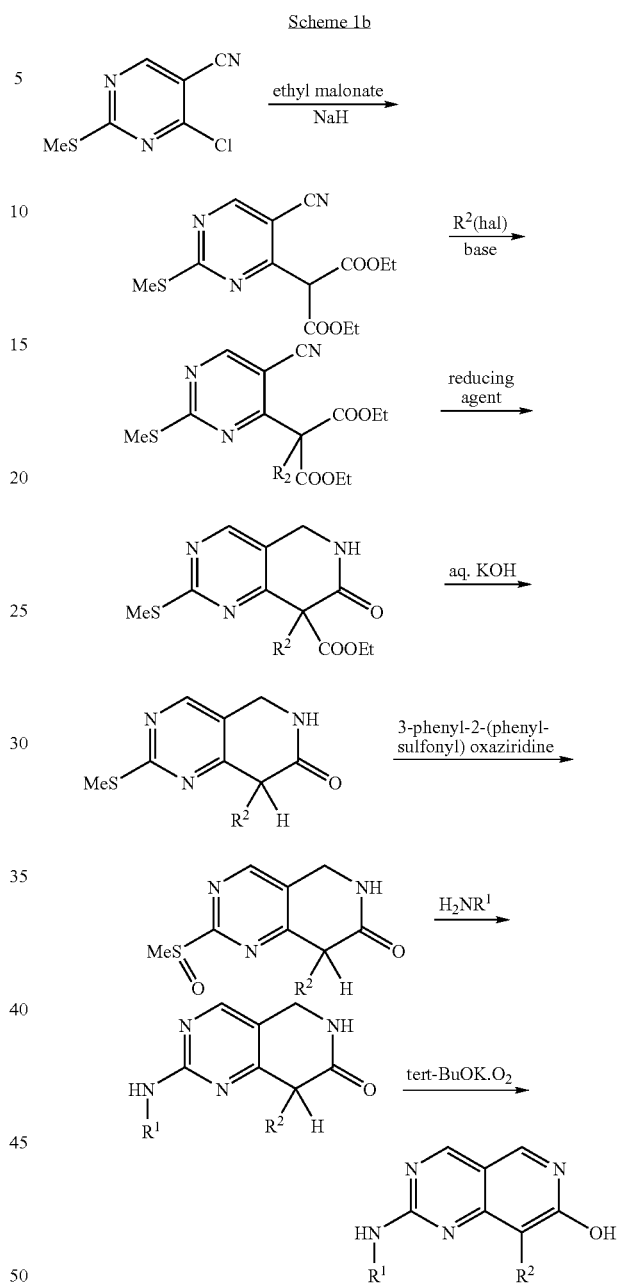

Schemes 1b and 1c describe general processes for preparing bicyclic pyrimidines of Formula I wherein G is C. In Scheme 1b, a 2-methylthio-4-halo-5-cyano pyrimidine is reacted with an alkyl malonate in the presence of a base such as sodium hydride to provide a pyrimidyl malonate derivative. $R^2$ groups such as alkyl and cycloalkyl can be inserted by reacting the pyrimidyl malonate intermediate with an alkyl or cycloalkyl halide in the presence of a base such as sodium carbonate or triethylamine. The 5-cyano group of the pyrimidyl malonate intermediate readily reacts with a reducing agent to effect reduction to an amino methyl group, the amino of which then displaces one of the alkoxy groups of the malonate portion to effect ring closure to provide the corresponding dihydro pyridopyrimidine. Decarboxylation of the remaining malonate carboxy group is readily accomplished by reaction with a base such as an alkali hydroxide, thus affording a 2-methylthio-5,6-dihydropyridopyrimidine. The methylthio group is oxidized to a sulfoxide, which is then readily displaced by reaction with an amine ($R^1NH_2$) to give a 2-amino-5,6-dihydropyridopyrimidine. Further oxidation by reaction with an alkali metal alkoxide and oxygen provides a fully aromatic 7-hydroxy-pyridopryimidine of the formula

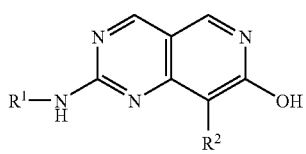

Scheme 1c shows a typical conversion of the 7-hydroxy pyridopyrimidine prepared as described above to 7-substituted amino compounds of Formula I (X=$NHR^{10}$). The 7-hydroxy compound is first reacted with a phosphorus oxy halide to provide the corresponding 7-halo pyridopyrimidine. The 7-halo group is readily displaced by reaction with an amine such as ammonia to give a 7-amino compound, which can be derivatized by standard processes to afford pyridopyrimidine of Formula I where X is $NHR^{10}$, for example

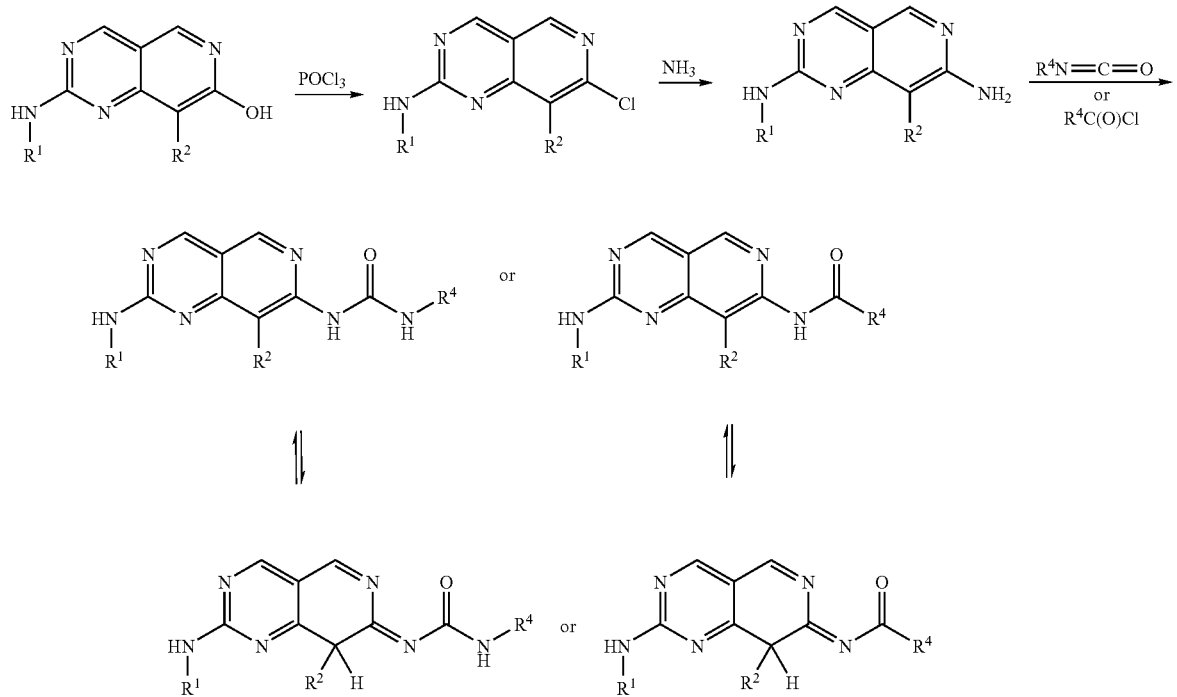

Scheme 2 illustrates a slightly different process for preparing invention compounds, starting with a suitably substituted pyridyl or pyrimidyl aldehyde of the formula

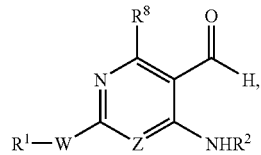

where R² is, for example, H or alkyl such as ethyl. All of the reactions in Scheme 2 are carried out by well-known procedures. The aldehyde is condensed with an N-substituted amine (H₂NR³) to provide an imine. The imine is reduced to a secondary amine, and the reduced amine is cyclized and subsequently converted to the key sulfoxide intermediate. The sulfoxide group is readily displaced by reaction with virtually any primary amine to give invention compounds of the general formula

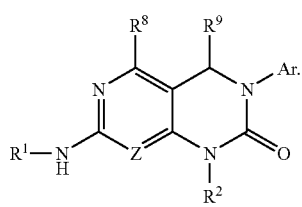

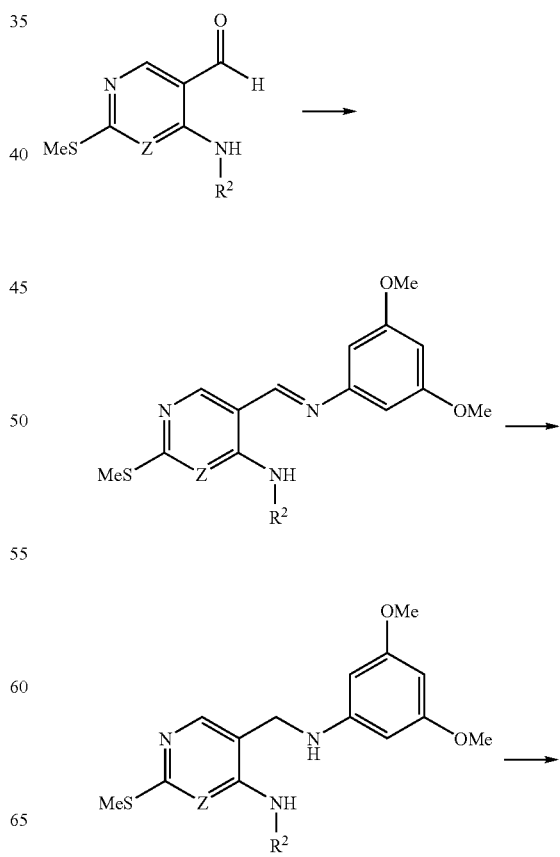

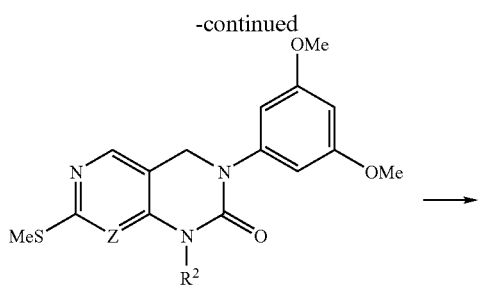

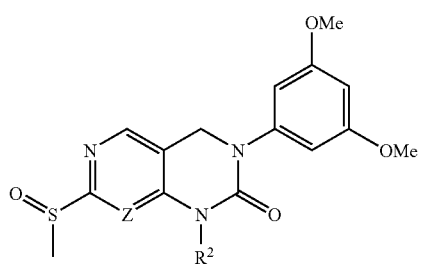

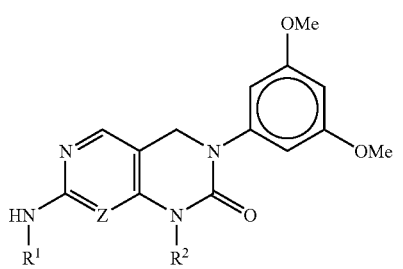

A preferred group of invention compounds have Formula I wherein $R^3$ is aryl such as disubstituted, trisubstituted, or tetrasubstituted phenyl. These are readily prepared by any of the foregoing processes, for example, by reacting a suitably substituted aniline with a pyridyl or pyrimidyl aldehyde as illustrated in Scheme 2. Typical anilines that can be employed in the reaction have the formula

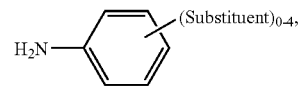

where the substituents are selected from phenyl, chloro, bromo, methyl, methoxy, hydroxy, hydroxymethyl, 2-diethylaminoethoxy, methoxycarbonylmethyl, carboxy, carboxymethyl, ethoxycarbonyl, 2-carboxyethyl, 2-ethoxycarbonylethyl, $NR^4R^5$, and $O(CH_2)_{0-6} NR^4R^5$, where $R^4$ and $R^5$ are defined above.

As noted above, a preferred group of invention compounds have Formula I wherein X is $NR^{10}$, as well as those wherein X is O. Typical invention compounds are prepared according to Scheme 3, starting with the reduced imine described in Scheme 2 (where $R^2$=H). The reduced imine is cyclized by reaction with cyanogen bromide, and the 7-methylthio group is oxidized to the corresponding sulfoxide, all as described above. The methylsulfoxide group is displaced by reaction with a primary amine ($H_2NR^1$), followed by derivatization of the 2-amino group by reaction with alkylating agents or acylating agents (e.g., alkyl isocvanates or acyl halides) to provide invention compounds of Formula I where X is $NHR^{10}$, e.g.,

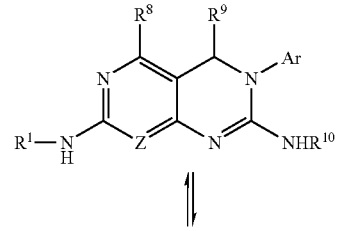

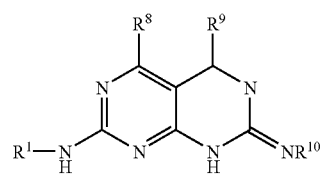

Scheme 3

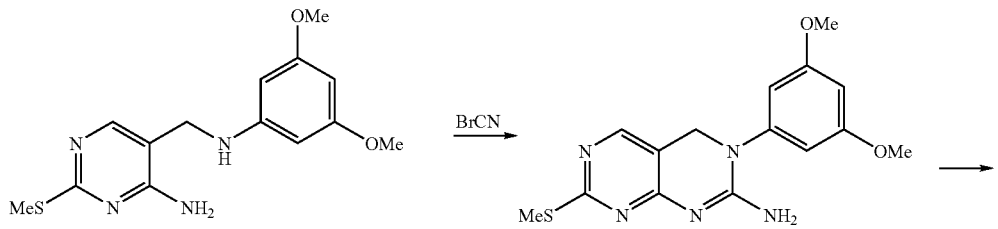

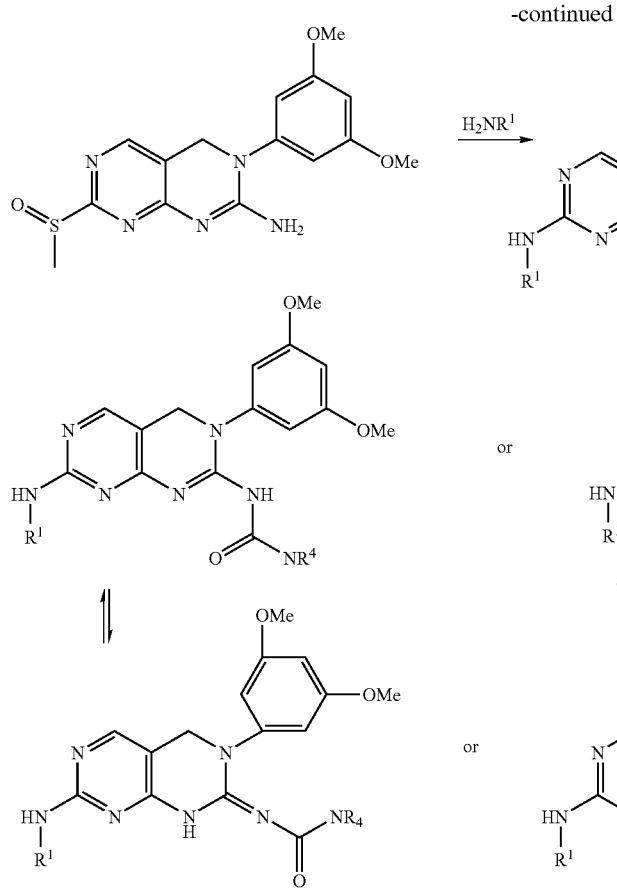
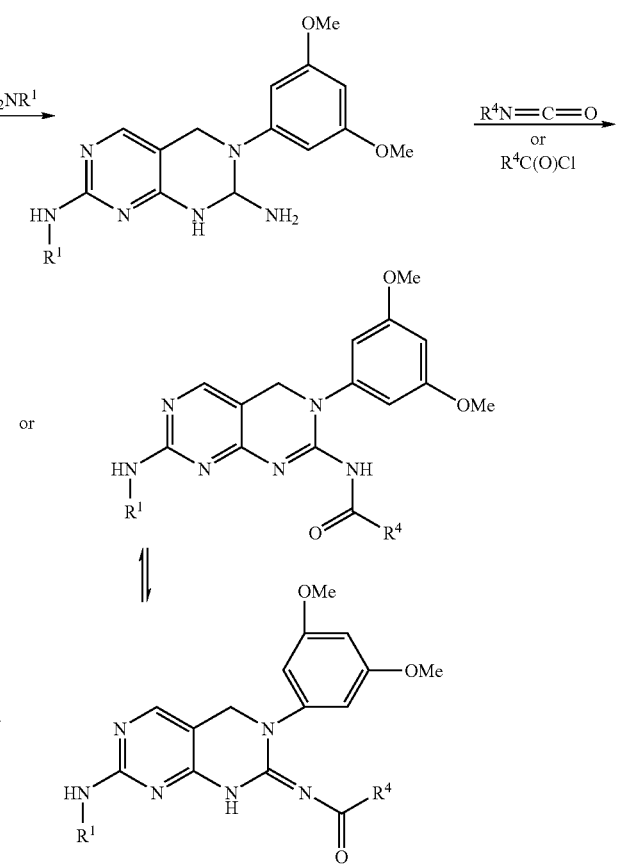

All of the invention compounds are readily purified by standard methods when desired. Typical purification steps employed include chromatography over solid supports such as silica gel or alumina. Elution generally is carried out using common solvents such as acetone, ethyl acetate, tetrahydrofuran, ethanol, triethylamine, and mixtures of such solvents. Other purification processes can similarly be employed, including crystallization from common solvents such as methanol, ethanol, diethyl ether, ethyl acetate, and the like. Sometimes such crystallizations can afford solvates such as an ethanol solvate, as well as hydrates, and all such solvates and hydrates are included in the scope of this invention.

The foregoing general reaction schemes are further described by the following detailed examples which are for illustrative purposes only and are not intended, nor should they be construed, as limiting the invention in any manner. Those skilled in the art will appreciate that variations and modifications can be made without violating the spirit or scope of the invention.

Preparations 1-10 and Examples 1-47 are specific embodiments of the general reaction schemes shown in Scheme 1 above.

Preparation 1

4-Hydroxy-2-(methylthio)-5-pyrimidinecarbonitrile

To a 5° C. solution of 119 g (703 mmol) of freshly distilled ethyl (ethoxymethylene)cyanoacetate in 800 mL of methanol is added 108 g (599 mmol) of 2-methyl-2-thiopseudourea. To this mixture is added a solution of sodium methoxide prepared by dissolving 35.6 g (1.55 mol) of sodium metal in 800 mL of methanol. The solution is warmed to room temperature and stirred for 6 hours. After standing overnight, the solvent is removed under reduced pressure, the residue is dissolved in 1.5 L of water at 50° C. with stirring, and the solution is filtered hot. The filtrate is acidified to pH 2 with concentrated HCl and kept at room temperature overnight. The precipitated product is collected and dried to give 48.3 g (48%) of the title compound, which is used directly in the next step.

Preparation 2

4-Chloro-2-(methylthio)-5-pyrimidinecarbonitrile

A mixture of 48.3 g (289 mmol) of 4-hydroxy-2-(methylthio)-5-pyrimidinecarbonitrile and 150 mL of phosphorus oxychloride is heated at reflux for 3 hours. The reaction mixture is cooled to room temperature, filtered, and the filtrate is concentrated to dryness. The residue is partitioned between dichloromethane and ice water. The organic phase is washed with water, dried over magnesium sulfate, and concentrated to a residue that is diluted with 750 mL of hexane. The stirred mixture is heated to reflux and the hot hexane solution is decanted from the insoluble material. Upon cooling to room temperature, crystals form and are collected to afford 32 g (60%) of the title compound.

Preparation 3

4-(Cyclopentylamino)-2-(methylthio)-5-pyrimidinecarbonitrile

To a 0° C. solution of 10.0 g (53.9 mmol) of 4-chloro-2-(methylthio)-5-pyrimidinecarbonitrile in 100 mL of dichloromethane is added 9.0 mL (64.6 mmol) of triethylamine followed by dropwise addition of 6.4 mL (64.6 mmol) of cyclopentylamine. The reaction mixture is stored at 0-10° C. for 16 hours, diluted with 100 mL of hexane, and filtered. The filtrate is chromatographed on silica gel eluting with 1:4:5 ethyl acetate/dichloromethane/hexane to obtain 4.6 g (36%) of product. The filtered solids, containing both product and triethylamine hydrochloride, are resuspended in 50 mL of dichloromethane and chromatographed as above to obtain 7.2 g (57%) of additional product: mp 119-122° C.

Analysis calculated for $C_{11}H_{14}N_4S$: C, 56.38; H, 6.02; N, 23.91.

Found: C, 56.48; H, 5.99; N, 24.12.

Preparation 4

4-(Isopropylamino)-2-(methylthio)-5-pyrimidinecarbonitrile

To a 0° C. solution of 20.0 g (107.7 mmol) of 4-chloro-2-(methylthio)-5-pyrimidinecarbonitrile in 200 mL of dichloromethane is added 18.0 mL (129.3 mmol) of triethylamine followed by dropwise addition of 11.0 mL (129.3 mmol) of isopropylamine. The reaction mixture is stirred at 0° C. for 3 hours, then for 30 minutes at room temperature. The resulting precipitate of triethylamine hydrochloride is filtered. The filtrate is chromatographed on a short column of silica gel eluting with dichloromethane. The pure fractions are pooled, concentrated, suspended in hexane, and filtered to obtain 13.7 g (61%) of product. The impure fractions, containing both product and triethylamine hydrochloride, are diluted with ethyl acetate, washed twice with water, and once with brine. The organic phase is dried over magnesium sulfate and concentrated. The residue is crystallized from 1:9 ethyl acetate/hexane to give 3.6 g (16%) of additional product: mp 121.0-122.5° C.

A Analysis calculated for $C_9H_{12}N_4S$: C, 51.90; H, 5.81; N, 26.90.

Found: C, 51.80; H, 5.82; N, 26.73.

Preparation 5

4-(Bicyclo[2.2.1]hept-2-ylamino)-2-(methylthio)-5-pyrimidinecarbonitrile (exo)

To a 0° C. solution of 10.0 g (53.9 mmol) of 4-chloro-2-(methylthio)-5-pyrimidinecarbonitrile in 100 mL of dichloromethane is added 9.0 mL (64.6 mmol) of triethylamine followed by dropwise addition of 7.0 mL (59.3 mmol) of exo-2-aminonorbornane. The reaction mixture is stirred at 0° C. for 2 hours. The resulting precipitate of triethylamine hydrochloride is filtered. The filtrate is washed three times with saturated aqueous solution of sodium bicarbonate. The aqueous phase is back extracted twice with dichloromethane. The combined organic phase is concentrated, and the residue is purified by filtering through a short column of silica gel eluted with dichloromethane to give 8.9 g (64%) of the title compound.

Analysis calculated for $C_{13}H_{16}N_4S$: C, 59.97; H, 6.19; N, 21.52.

Found: C, 59.70; H, 6.08; N, 21.41.

Preparation 6

4-(Methylamino)-2-(methylthio)-5-pyrimidinecarbonitrile

Through a 5° C. solution of 14.5 g (78.1 mmol) of 4-chloro-2-(methylthio)-5-pyrimidinecarbonitrile in 800 mL of diethyl ether is bubbled methylamine gas for a period of 15 minutes. The reaction mixture is allowed to warm to room temperature, set overnight, and filtered. The solids are washed with diethyl ether, then efficiently with 50 mL of water, and dried to give 12.0 g (81%) of the title compound: mp 189-190° C.

Analysis calculated for $C_7H_8N_4S$: C, 46.65; H, 4.47; N, 31.09.

Found: C, 46.79; H, 4.60; N, 31.26.

Preparation 7

5-(Aminomethyl)-4-(cyclopentylamino)-2-(methylthio)pyrimidine

To a stirred 0° C. suspension of 1.7 g (44.8 mmol) of LAH in 70 mL of tetrahydrofuran is added dropwise a solution of 5.0 g (21.3 mmol) of 4-(cyclopentylamino)-2-(methylthio)-5-pyrimidinecarbonitrile in 250 mL of tetrahydrofuran. The reaction is allowed to warm slowly to room temperature overnight. The mixture is recooled to 0° C., and treated with a saturated solution of ammonium sulfate until there is no more effervescence. After stirring for another 15 minutes, the gray solids are filtered and washed four times with hot ethyl acetate. The combined organic washes are concentrated, and the residue is chromatographed on silica gel eluting with 1:1:8 methanol/hexane/chloroform to obtain 4.0 g (79%) of the title compound: mp 58-60° C.

Analysis calculated for $C_{11}H_{18}N_4S$: C, 55.43; H, 7.61; N, 23.51.

Found: C, 55.45; H, 7.56; N, 23.49.

Preparation 8

5-(Aminomethyl)-4-(isopropylamino)-2-(methylthio)pyrimidine

To a stirred 0° C. suspension of 5.9 g (156.3 mmol) of LAH in 200 mL of tetrahydrofuran is added dropwise a solution of 15.5 g (74.4 mmol) of 4-(isopropylamino)-2-(methylthio)-5-pyrimidinecarbonitrile in 500 mL of tetrahydrofuran. The reaction is allowed to warm slowly to room temperature overnight. The mixture is recooled to 0° C., and treated with a saturated solution of ammonium sulfate until there is no more effervescence. After stirring for another 15 minutes, the gray solids are filtered and washed six times with hot ethyl acetate. The combined organic washes are concentrated, and the residue is purified by chromatography in two portions on a 4×15 cm Biotage silica gel column that is eluted with 60:38:2 acetonitrile/dichloromethane/triethylamine followed by 60:33:5:2 acetonitrile/dichloromethane/methanol/triethylamine to obtain 12.9 g (82%) of the title compound as a yellow oil. Mass Spectrum (CI) (m+1)/z 213.

Preparation 9

5-(Aminomethyl)-4-(bicyclo[2.2.1]hept-2-ylamino)-2-(methylthio)pyrimidine (exo)

To a stirred 0° C. suspension of 2.5 g (65.3 mmol) of LAH in 100 mL of tetrahydrofuran is added dropwise a solution of 8.5 g (32.6 mmol) of 4-(bicyclo[2.2.1]hept-2-yl-amino)-2-(methylthio)-5-pyrimidinecarbonitrile in 375 mL of tetrahydrofuran. The reaction is allowed to warm slowly to room temperature overnight. The mixture is recooled to 0° C. and treated with a saturated solution of ammonium sulfate until there is no more effervescence. After stirring for another 15 minutes, the gray solids are filtered and washed four times with hot ethyl acetate. The combined organic washes are concentrated, and the residue is purified by chromatography on silica gel that is eluted with methanol/dichloromethane 1:9 followed by 2:8 to obtain 5.8 g (68%) of the title compound.

Analysis calculated for $C_{13}H_{20}N_4S$: C, 59.06; H, 7.62; N, 21.19.

Found: C, 58.94; H, 7.86; N, 21.04.

Preparation 10

5-(Aminomethyl)-4-(methylamino)-2-(methylthio)pyrimidine

To a stirred 0° C. suspension of 17.0 g (448 mmol) of lithium aluminum hydride in 500 mL of tetrahydrofuran is added dropwise a solution of 30.0 g (166 mmol) of 4-(methylamino)-2-(methylthio)-5-pyrimidinecarbonitrile in 1.5 L of tetrahydrofuran. The reaction is allowed to warm slowly to room temperature overnight. The mixture is recooled to 0° C., and treated with a saturated solution of ammonium sulfate until there is no more effervescence (80-100 mL). After stirring for another 15 minutes, the gray solids are filtered and washed 3 times with hot tetrahydrofuran and once with hot ethyl acetate. The combined organic washes are concentrated, and the residue is chromatographed on silica gel eluting with 0.5:25:75 triethylamine/methanol/chloroform to obtain 21.6 g (70%) of an oil which solidified on standing of the title compound.

Mass Spectrum (CI) (m+1)/z 185.

EXAMPLE 1

1-Cyclopentyl-7-methanesulfanyl-3,4-dihydro-pyrimido[4,5-d]pyrimidin-2(1H)-one

To a 0° C. solution of 4.2 g (17.6 mmol) of 5-(aminomethyl)-4-(cyclopentylamino)-2-(methylthio)pyrimidine in 100 mL of tetrahydrofuran is added 3.4 g (21.1 mmol) of 1,1'-carbonyldiimidazole. The solution is stirred at 0° C. for 30 minutes, then heated at a gentle reflux overnight. The mixture is concentrated to a solid residue that is stirred as a suspension in chloroform for 4 hours. The powdery solid is collected and dried to give 2.6 g of product contaminated with about 5% imidazole. The filtrate is chromatographed on silica gel eluting with 6:4 ethyl acetate/dichloromethane to give 1.6 g of product contaminated with about 10% imidazole. A small portion is crystallized from chloroform to obtain an analytically pure sample of the title compound:

mp 179-182° C.

Analysis calculated for $C_{12}H_{16}N_4OS$: C, 54.52; H, 6.10; N, 21.19.

Found: C, 54.42; H, 6.11; N, 21.29.

EXAMPLE 2

1-Isopropyl-7-methanesulfanyl-3,4-dihydro-pyrimido[4,5-d]pyrimidin-2(1H)-one

To a 0° C. solution of 12.0 g (56.5 mmol) of 5-(aminomethyl)-4-(isopropylamino)-2-(methylthio)pyrimidine in 300 mL of tetrahydrofuran is added 11.0 g (67.8 mmol) of 1,1'-carbonyldiimidazole. The solution is stirred at 0° C. for 30 minutes, then heated at a gentle reflux overnight. The mixture is concentrated to a solid residue that is dissolved in chloroform, washed twice with 1N HCl, water, a saturated solution of sodium bicarbonate, and brine. The organic phase is dried over magnesium sulfate and concentrated. The crude solid residue is crystallized from chloroform/hexane to obtain 9.7 g (72%) of the title compound:

mp 175.0-176.5° C.

Analysis calculated for $C_{10}H_{14}N_4OS$: C, 50.40; H, 5.92; N, 23.51.

Found: C, 50.35; H, 5.90; N, 23.54.

EXAMPLE 3

1-Bicyclo[2.2.1]hept-2-yl-7-methanesulfanyl-3,4-dihydro-pyrimido[4,5-d]pyrimidin-2(1H)-one (exo)

To a 0° C. solution of 4.6 g (17.6 mmol) of 5-(aminomethyl)-4-(bicyclo[2.2.1]hept-2-yl-amino)-2-(methylthio)pyrimidine in 100 mL of tetrahydrofuran is added 3.7 g (22.7 mmol) of 1,1'-carbonyldiimidazole. The solution is stirred at 0° C. for 30 minutes, room temperature for 2 hours, then heated at a gentle reflux for 48 hours. The mixture is diluted with brine and extracted with diethyl ether. The organic phase is concentrated, and the residue is purified by chromatography on silica gel that is eluted with methanol/dichloromethane 5:95 then 10:90 to obtain 2.2 g (85%) of the title compound: mp 133-134° C.

Analysis calculated for $C_{14}H_{18}N_4OS$: C, 57.91; H, 6.25; N, 19.29.

Found: C, 57.61; H, 6.09; N, 19.12.

EXAMPLE 4

7-Methanesulfanyl-1-methyl-3,4-dihydro-pyrimido[4,5-d]pyrimidin-2(1H)-one

To a 0° C. solution of 21.2 g (152.2 mmol) of 5-(aminomethyl)-4-(methylamino)-2-(methylthio)pyrimidine in 900 mL of tetrahydrofuran and 100 mL of dimethylformamide is added 3.4 g (21.1 mmol) of 1,1'-carbonyldiimidazole. The solution is stirred at 0° C. for 1 hour, then heated at a gentle reflux for 10 hours. The mixture is cooled, and the solid is collected, washed with diethyl ether, and dried to give 18.6 g (78%) of the title compound:

mp 263-265° C.

Analysis calculated for $C_8H_{10}N_4OS$: C, 45.70; H, 4.79; N, 26.65; S, 15.25.

Found: C, 46.15; H, 4.59; N, 26.62; S, 15.51.

EXAMPLE 5

1-Cyclopentyl-7-methanesulfinyl-3,4-dihydro-pyrimido[4,5-d]pyrimidin-2(1H)-one

To a room temperature solution of 3.7 g (14.0 mmol) of 1-cyclopentyl-7-methanesulfanyl-3,4-dihydro-pyrimido[4,5-d]pyrimidin-2(1H)-one in 40 mL of chloroform is added 4.4 g (16.8 mmol) of 3-phenyl-2-(phenylsulfonyl)-oxaziridine. The reaction mixture is stirred for 3 hours, filtered, and washed with 1:1 chloroform/hexane to give 2.85 g (73%) of the title compound: mp 235-236° C. (dec).

Analysis calculated for $C_{12}H_{16}N_4O_2S$: C, 51.41; H, 5.75; N, 19.98.

Found: C, 50.43; H, 5.55; N, 19.52.

EXAMPLE 6

1-Isopropyl-7-methanesulfinyl-3,4-dihydro-pyrimido [4,5-d]pyrimidin-2(1H)-one

To a room temperature solution of 7.0 g (29.4 mmol) of 1-isopropyl-7-methanesulfanyl-3,4-dihydro-pyrimido[4,5-d]pyrimidin-2(1H)-one in 80 mL of chloroform is added 9.2 g (35.2 mmol) of 3-phenyl-2-(phenylsulfonyl)oxaziridine. The reaction mixture is stirred overnight, diluted with 40 mL of hexane, filtered, and washed with 1:1 chloroform/hexane to give 6.4 g (85%) of the title compound: mp 218-219° C. (dec).

Analysis calculated for $C_{10}H_{14}N_4O_2S$: C, 47.23; H, 5.55; N, 22.03.

Found: C, 46.88; H, 5.40; N, 21.56.

EXAMPLE 7

1-Bicyclo[2.2.1]hept-2-yl-7-methanesulfinyl-3,4-dihydro-pyrimido [4,5-d]pyrimidin-2(1H)-one (exo)

To a room temperature solution of 2.0 g (6.9 mmol) of 1-bicyclo[2.2.1]hept-2-yl-7-methanesulfanyl-3,4-dihydro-pyrimido[4,5-d]pyrimidin-2(1H)-one in 20 mL of chloroform is added 2.1 g (8.3 mmol) of 3-phenyl-2-(phenylsulfonyl)oxaziridine. The reaction mixture is stirred overnight, 200 mg (0.76 mmol) more of 3-phenyl-2-(phenylsulfonyl)oxaziridine is added, and stirred overnight. The product is isolated by chromatography on a 4×15 cm Biotage silica gel column by applying the reaction mixture to the column and eluting in a gradient fashion with methanol/chloroform 2:98 then 4:96 then 8:92 to give 1.1 g (51%) of the title compound: mp 220-222° C. (dec).

Mass Spectrum (CI) (m+1)/z 307 and 264.

EXAMPLE 8

7-Methanesulfinyl-1-methyl-3,4-dihydro-pyrimido [4,5-d]pyrimidin-2(1H)-one

To a room temperature solution of 9.0 g (42.8 mmol) of 7-methanesulfanyl-1-methyl-3,4-dihydro-pyrimido[4,5-d]pyrimidin-2(1)-one in 100 mL of chloroform is added 12.5 g (47.8 mmol) of 3-phenyl-2-(phenylsulfonyl)oxaziridine. The reaction mixture is stirred for 6 hours, 3.1 g (11.9 mmol) more of 3-phenyl-2-(phenylsulfonyl)oxaziridine is added, and stirred overnight. The reaction mixture is stored overnight at 0° C., filtered, and dried under vacuum at 75° C. to a constant weight of 9.7 g (100%) of the title compound:

mp 225-228° C. (dec).

Mass Spectrum (CI) (m+1)/z 227.

EXAMPLE 9

1-Cyclopentyl-7-(4-methoxyphenylamino)-3,4-dihydro-pyrimido[4,5-d]pyrimidin-2(1H)-one A solution of 300 mg (1.07 mmol) of 1-cyclopentyl-7-methanesulfinyl-3,4-dihydro-pyrimido[4,5-d]pyrimidin-2 (1H)-one, 527 mg (4.28 mmol) of p-anisidine, and 1.5 mL of dimethyl sulfoxide is heated at 130° C. for 30 hours, then cooled and diluted with ethyl acetate. The mixture is washed three times with aqueous sodium chloride solution, dried over magnesium sulfate, and concentrated. The residual solids are washed with 9:1:0.1:0.1 chloroform/ethyl acetate/ethanol/triethylamine then with chloroform, and suspended in 150 mL of 7:3 chloroform/methanol. The suspension is diluted with 20 mL of hexane, stirred for 3 hours, and filtered to afford 88 mg (24%) of the title compound as an off-white powder: mp 247-249° C. (dec).

Analysis calculated for $C_{18}H_{21}N_5O_2$: C, 63.70; H, 6.24; N, 20.63.

Found: C, 63.45; H, 6.04; N, 20.62.

EXAMPLE 10

1-Cyclopentyl-7-[4-(piperidin-1-yl)phenylamino]-3, 4-dihydro-pyrimido [4,5-d]pyrimidin-2(1H)-one A solution of 377 mg (2.14 mmol) of 1-(4-aminophenyl) piperidine, 300 mg (1.07 mmol) of 1-cyclopentyl-7-methanesulfinyl-3,4-dihydro-pyrimido[4,5-d]pyrimidin-2(1H)-one, 745 mg (3.21 mmol) of camphorsulfonic acid, and 2 mL of p-dioxane is heated at 130° C. for 1 hour in a sealed tube. The mixture is cooled and diluted with chloroform. The solution is washed twice with saturated aqueous sodium bicarbonate and once each with aqueous sodium chloride then brine. The organic phase is dried over magnesium sulfate and concentrated to leave a dark green residue that is dissolved in chloroform and chromatographed on silica gel eluting with 9:1: 0.5 ethyl acetate/ethanol/triethylamine. The product fractions are pooled and concentrated to leave a residue that is dissolved in chloroform. The solution is diluted with ethyl acetate while most of the chloroform is being boiled away. Upon cooling, crystals form and are then collected to leave 101 mg (24%) of the title compound:

mp 254-277° C. (dec).

Analysis calculated for $C_{22}H_{28}N_6O$: C, 67.32; H, 7.19; N, 21.41.

Found: C, 67.10; H, 7.06; N, 21.58.

EXAMPLE 11

1-Cyclopentyl-7-[4-(4-methylpiperazin-1-yl)phenylamino]-3,4-dihydro-pyrimido[4,5-d]pyrimidin-2 (1H)-one To a solution of 2.0 g (7.1 mmol) of 1-cyclopentyl-7-methanesulfinyl-3,4-dihydro-pyrimido[4,5-d]pyrimidin-2 (1H)-one and 2.7 g (14.3 mmol) of 1-(4-aminophenyl)-4-methylpiperazine in 32 mL of acetonitrile is added 2.75 mL (35.7 mmol) of trifluoroacetic acid. The mixture is heated at 85° C. overnight. The cooled reaction mixture is diluted with ethyl acetate and washed two times with saturated aqueous sodium bicarbonate solution and once with brine. The combined aqueous phase is back extracted with dichloromethane. The combined organic phase is dried over magnesium sulfate and concentrated. The dark solid residue is stirred for 2 hours in 30 mL of 1:1 dichloromethane/ethyl acetate, filtered, washed with ethyl acetate, and dried to give 2.3 g (80%) of the title compound: mp 236-239° C. (dec).

Analysis calculated for $C_{22}H_{29}N_7O$: C, 64.84; H, 7.17; N, 24.06.

Found: C, 64.55; H, 7.00; N, 24.00.

General Method for the Preparation of other 1-cyclopentyl-7-(Substituted phenylamino)-3,4-dihydropyrimido[4,5-d]pyrimidin-2(1H)-ones To a solution of 200 mg (0.71 mmol) of 1-cyclopentyl-7-methanesulfinyl-3,4-dihydro-pyrimido[4,5-d]pyrimidin-2(1H)-one and two equivalents of the substituted aniline in 3.2 mL of acetonitrile is added trifluoroacetic acid. The mixture is heated at 85° C. overnight, cooled to room temperature, diluted with ethyl acetate or dichloromethane, and washed two times with saturated aqueous sodium bicarbonate solution and once with brine. The organic phase is dried over magnesium sulfate, and concentrated to leave a residue that is further processed as described above to give a compound of Formula I.

The following specific invention compounds were prepared according to the foregoing general process.

EXAMPLE 12

1-Cyclopentyl-7-[4-(pyrazol-1-yl)phenylamino]-3,4-dihydro-pyrimido[4,5-d]pyrimidin-2(1H)-one Prepared from 222 mg (1.43 mmol) of 1-(4-aminophenyl)-4-(pyrazol-1-yl)piperidine and 165 µL (2.1 mmol) of trifluoroacetic acid. After heating, a heavy precipitate forms. The cooled reaction mixture is diluted with 4 mL of ethyl acetate and filtered. The solids are washed with ethyl acetate and dried to give 275 mg (79%) of the trifluoroacetate salt of the title compound: mp 256-258° C. (dec).

Analysis calculated for $C_{22}H_{28}N_6O_2 \cdot C_2HF_3O_2$: C, 53.99; H, 4.53; N, 20.03.

Found: C, 53.82; H, 4.52; N, 20.05.

EXAMPLE 13

1-Cyclopentyl-7-{3-methyl-4-[2-(diethylamino)ethoxy]phenylamino}-3,4-dihydro-pyrimido[4,5-d]pyrimidin-2(1H)-one Prepared from 317 mg (1.43 mmol) of 3-methyl-4-[2-(diethylamino)-ethoxy]aniline and 165 µL (2.1 mmol) of trifluoroacetic acid. The crude residue is suspended in ethyl acetate/dichloromethane and stirred for several hours. The solids are collected, washed with ethyl acetate, and dried to give 210 mg (67%) of the title compound: mp 175-177° C.

Analysis calculated for $C_{24}H_{34}N_6O_2$: C, 65.73; H, 7.81; N, 19.16.

Found: C, 65.42; H, 7.73; N, 19.17.

EXAMPLE 14

1-Cyclopentyl-7-[4-(pyrrol-1-yl)phenylamino]-3,4-dihydro-pyrimido[4,5-d]pyrimidin-2(1H)-one Prepared from 226 mg (1.43 mmol) of 1-(4-aminophenyl)pyrrole and 165 µL (2.1 mmol) of trifluoroacetic acid. The crude residue is suspended in ethyl acetate/dichloromethane/acetonitrile and stirred for several hours. The solids are collected, washed with ethyl acetate, and dried to give 90 mg (32%) of the title compound: mp>200° C. (dec).

Analysis calculated for $C_{21}H_{22}N_6O \cdot 0.33H_2O$: C. 66.31; H, 6.00; N, 22.09.

Found: C, 66.35; H, 5.92; N, 21.94.

EXAMPLE 15

1-Cyclopentyl-7-[4-(4-hydroxypiperidin-1-yl)phenylamino]-3,4-dihydro-pyrimido[4,5-d]pyrimidin-2(1H)-one Prepared from 274 mg (1.43 mmol) of 1-(4-aminophenyl)-4-hydroxypiperidine and 330 µL (4.3 mmol) of trifluoroacetic acid. The crude residue is suspended in ethyl acetate/dichloromethane/acetonitrile and stirred for several hours. The solids are collected, washed with ethyl acetate, and dried to give 140 mg (47%) of the title compound: mp>200° C. (dec).

Analysis calculated for $C_{22}H_{28}N_6O_2 \cdot 0.5H_2O$: C. 63.29; H, 7.00; N, 20.13.

Found: C, 63.27; H, 6.65; N, 19.99.

EXAMPLE 16

1-Cyclopentyl-7-[4-(3-hydroxypiperidin-1-yl)phenylamino]-3,4-dihydro-pyrimido[4,5-d]pyrimidin-2(1H)-one Prepared from 274 mg (1.43 mmol) of 1-(4-aminophenyl)-3-hydroxypiperidine and 330 µL (4.3 mmol) of trifluoroacetic acid. The crude residue is suspended in ethyl acetate/dichloromethane and stirred for several hours. The solids are collected, washed with ethyl acetate, and dried to give 135 mg (42%) of the title compound: mp>200° C. (dec).

Analysis calculated for $C_{22}H_{28}N_6O_2 \cdot 0.15 \, CH_2Cl_2$: C, 63.16; H, 6.77; N. 19.95.

Found: C, 63.18; H, 6.66; N, 19.97.

EXAMPLE 17

1-Cyclopentyl-7-{4-[4-(dimethylamino)piperidin-1-yl]phenylamino}-3,4-dihydro-pyrimido[4,5-d]pyrimidin-2(1H)-one Prepared from 313 mg (1.43 mmol) of 1-(4-aminophenyl)-4-(dimethylamino)piperidine and 275 µL (3.75 mmol) of trifluoroacetic acid. The crude residue is suspended in ethyl acetate/dichloromethane and stirred for several hours. The solids are collected, washed with ethyl acetate, and dried to give 80 mg (24%) of the title compound: mp>200° C. (dec).

Analysis calculated for $C_{24}H_{33}N_7O_2 \cdot 0.23 \, CH_2Cl_2$: C, 63.95; H, 7.41; N, 21.54.

Found: C, 63.99; H, 7.38; N, 21.28.

EXAMPLE 18

1-Cyclopentyl-7-[4-(3,5-dimethylpiperazin-1-yl)phenylamino]-3,4-dihydro-pyrimido[4,5-d]pyrimidin-2(1H)-one Prepared from 292 mg (1.43 mmol) of 1-(4-aminophenyl)-3,5-dimethylpiperazine and 165 mL (2.1 mmol) of trifluoroacetic acid. The crude residue is purified by chromatography on a 1.2×7 cm Biotage silica gel column that is eluted with 50:40:5:5 acetonitrile/ethyl acetate/methanol/triethylamine. Product fractions are pooled and concentrated to leave a residue that is crystallized from dichloromethane/ethyl acetate to give 16 mg (5%) of the title compound:

mp>200° C. (dec).

Analysis calculated for $C_{23}H_{31}N_7O \cdot 0.15 \, CH_2Cl_2 \cdot 0.01 \, C_4H_8O_2$: C, 64.01; H, 7.27; N, 22.53.

Found: C, 63.98; H, 7.06; N, 22.60.

EXAMPLE 19

1-Cyclopentyl-7-[4-(2-hydroxymethylpiperidin-1-yl) phenylamino]-3,4-dihydro-pyrimido[4,5-d]pyrimidin-2(1H)-one Prepared from 294 mg (1.43 mmol) of 1-(4-aminophenyl)-2-hydroxymethylpiperidine and 330 μL (4.3 mmol) of trifluoroacetic acid. The crude residue is purified by chromatography on a 1.2×7 cm Biotage silica gel column that is eluted with 3:2 ethyl acetate/dichloromethane. Product fractions are pooled and concentrated to give 130 mg (43%) of the title compound:

mp 220-221° C.

Analysis calculated for $C_{23}H_{30}N_6O_2$: C, 65.38; H, 7.16; N, 19.89.

Found: C, 65.13; H, 7.15; N, 19.87.

EXAMPLE 20

1-Cyclopentyl-7-{4-[4-(3-hydroxypropyl)piperidin-1-yl]phenylamino}-3,4-dihydro-pyrimido[4,5-d]pyrimidin-2(1H)-one Prepared from 335 mg (1.43 mmol) of 1-(4-aminophenyl)-4-(3-hydroxypropyl)piperidine and 330 μL (4.3 mmol) of trifluoroacetic acid. The crude residue is suspended in ethyl acetate/dichloromethane and stirred for several hours. The solids are collected and crystallized from ethyl acetate/dichloromethane. The impure product is further purified by dissolution in 9:2:1 ethyl acetate/ethanol/triethylamine then passage through a column of silica gel eluting with the same solvent to give 31 mg (10%) of the title compound:

mp>230° C.

Analysis calculated for $C_{25}H_{34}N_6O_2$: C, 65.67; H, 7.51; N, 18.31.

Found: C, 65.50; H, 7.40; N, 18.30.

EXAMPLE 21

1-Cyclopentyl-7-[4-(2-(morpholin-1-yl)ethyl)piperidin-1-yl)phenylamino]-3,4-dihydro-pyrimido[4,5-d]pyrimidin-2(1H)-one Prepared from 500 mg (1.43 mmol) of 1-(4-aminophenyl)-4-(2-(1-morpholino)ethyl))piperidine and 275 μL (4.3 mmol) of trifluoroacetic acid. The crude residue is dissolved in 15 mL of dichloromethane, and the solution is concentrated to 5 mL, then diluted with 15 mL of ethyl acetate to precipitate solids. The suspension is stirred for 2 hours, filtered, and washed with ethyl acetate. The brown powder is dissolved in dichloromethane and filtered through a short column of silica with 1:9 methanol/chloroform. The filtrate is concentrated to a pink powder that is dissolved in 20 mL of dichloromethane and 3 drops of methanol. The solution is diluted with 30 mL of ethyl acetate, then while stirring slowly, concentrated to 30 mL under a stream of nitrogen. The precipitated pale powder is filtered and dried to give 54 mg (11%) of the title compound: mp 218-220° C.

Analysis calculated for $C_{22}H_{28}N_6O_2.0.1\ CH_2Cl_2.0.1H_2O$: C, 65.41; H, 7.70; N, 19.00.

Found: C, 65.70; H, 7.74; N, 19.37.

General Method for the Preparation of 1-isopropyl-7-(Substituted phenylamino)-3,4-dihydro-pyrimido[4,5-d]pyrimidin-2(1H)-ones To a solution of 1-isopropyl-7-methanesulfinyl-3,4-dihydro-pyrimido[4,5-d]pyrimidin-2(1H)-one and two equivalents of the substituted aniline in acetonitrile is added trifluoroacetic acid. The mixture is heated at 85° C. overnight, cooled to room temperature, diluted with ethyl acetate or dichloromethane, and washed two times with saturated aqueous sodium bicarbonate solution and once with brine. The organic phase is dried over magnesium sulfate, and concentrated to leave a residue that is further processed as described in the following examples to give a compound of Formula I.

The following specific invention compounds were prepared according to the foregoing general process.

EXAMPLE 22

1-Isopropyl-7-[4-(4-methylpiperazin-1-yl)phenylamino]-3,4-dihydro-pyrimido[4,5-d]pyrimidin-2(1H)-one Prepared from 400 mg (1.57 mmol) of 1-isopropyl-7-methanesulfinyl-3,4-dihydro-pyrimido[4,5-d]pyrimidin-2(1H)-one, 600 mg (3.14 mmol) of 1-(4-aminophenyl)-4-methylpiperazine and 605 μL (7.85 mmol) of trifluoroacetic acid in 6.4 mL of acetonitrile. The reaction mixture is heated at 85° C. for 48 hours. After the workup, the crude residue is triturated in ethyl acetate/dichloromethane and filtered. The solids are redissolved in dichloromethane, and the solvent is evaporated under a flow of nitrogen while ethyl acetate is added to maintain a volume of 5 mL. The suspension is filtered, and the solids are washed with ethyl acetate/dichloromethane, and dried to give 470 mg (78%) of the title compound:

mp 234-237° C. (dec).

Analysis calculated for $C_{20}H_{27}N_7O.0.15\ C_4H_8O_2.0.05\ CH_2Cl_2$: C, 62.17; H, 7.15; N, 24.58.

Found: C, 62.01; H, 7.06; N, 24.57.

EXAMPLE 23

7-[4-(4-Hydroxypiperidin-1-yl)phenylamino]-1-isopropyl-3,4-dihydro-pyrimido[4,5-d]pyrimidin-2(1H)-one Prepared from 200 mg (0.79 mmol) of 1-isopropyl-7-methanesulfinyl-3,4-dihydro-pyrimido[4,5-d]pyrimidin-2(1H)-one, 302 mg (1.57 mmol) of 1-(4-aminophenyl)-4-hydroxypiperidine and 182 μL (2.36 mmol) of trifluoroacetic acid in 3.2 mL of acetonitrile. After the workup, the crude residue is triturated in ethyl acetate/dichloromethane and filtered. The filtrate is concentrated further to produce a second crop of crystals. The two are combined and dried to give 45 mg (13%) of the title compound: mp>120° C. (dec).

Analysis calculated for $C_{20}H_{26}N_6O_2.0.3\ C_4H_8O_2 0.5H_2O$: C, 60.93; H, 7.09; N, 20.11.

Found: C, 60.95; H, 6.82; N, 20.35.

EXAMPLE 24

7-{4-[4-(Dimethylamino)piperidin-1-yl]phenylamino}-1-isopropyl-3,4-dihydro-pyrimido[4,5-d]pyrimidin-2(1H)-one; compound with trifluoroacetic acid Prepared from 400 mg (1.57 mmol) of 1-isopropyl-7-methanesulfinyl-3,4-dihydro-pyrimido[4,5-d]pyrimidin-2(1H)-one, 690 mg (3.14 mmol) of 1-(4-aminophenyl)-4-(dimethylamino)piperidine and 605 μL (7.86 mmol) of trifluoroacetic acid in 5 mL of acetonitrile. After heating the reaction mixture overnight, a heavy precipitate forms. The cooled reaction mixture is diluted with 6 mL of ethyl acetate and filtered. The solids are washed twice with ethyl acetate, once with ethyl acetate/dichloromethane and dried to give 389 mg (38%) of the trifluoroacetate salt of the title compound: mp 215-217° C. (dec).

Analysis calculated for $C_{22}H_{31}N_7O.2.0 \ C_2HF_3O_2.0.1 \ C_4H_8O_2.0.25H_2O$: C, 48.72; H, 5.31; N, 15.06.

Found: C, 48.67; H, 5.15; N, 15.05.

EXAMPLE 25

1-Isopropyl-7-[4-(pyrazol-1-yl)phenylamino]-3,4-dihydro-pyrimido[4,5-d]pyrimidin-2(1H)-one; compound with trifluoroacetic acid Prepared from 200 mg (0.79 mmol) of 1-isopropyl-7-methanesulfinyl-3,4-dihydro-pyrimido[4,5-d]pyrimidin-2(1H)-one, 250 mg (1.57 mmol) of 1-(4-aminophenyl)pyrazole and 182 µL (2.36 mmol) of trifluoroacetic acid in 3.2 mL of acetonitrile. After heating the reaction mixture overnight, a heavy precipitate forms. The cooled reaction mixture is diluted with ethyl acetate and filtered. The solids are washed with ethyl acetate and dried to give 315 mg (86%) of the trifluoroacetate salt of the title compound: mp 249-252° C. (dec).

Analysis calculated for $C_{18}H_{19}N_7O.C_2HF_3O_2$: C, 51.84; H, 4.35; N, 21.16.

Found: C, 51.94; H, 4.37; N, 21.02.

EXAMPLE 26

1-Isopropyl-7-{4-[4-(3-(morpholin-1-yl)propyl)piperidin-1-yl]phenylamino}-3,4-dihydro-pyrimido[4,5-d]pyrimidin-2(1H)-one Prepared from 200 mg (0.79 mmol) of 1-isopropyl-7-methanesulfinyl-3,4-dihydro-pyrimido[4,5-d]pyrimidin-2(1H)-one, 477 mg (1.57 mmol) of 1-(4-aminophenyl)-4-(3-(1-morpholino)propyl))piperidine and 303 µL (3.93 mmol) of trifluoroacetic acid in 3.2 mL of acetonitrile. After the workup, the crude residue is triturated in ethyl acetate/dichloromethane and filtered. The solids are washed with ethyl acetate and dried to give 140 mg (33%) of the title compound: mp 203-205° C. (dec).

Analysis calculated for $C_{27}H_{39}N_7O_2.0.1 \ C_4H_8O_2.0.25H_2O$: C, 64.92; H, 8.01; N, 19.34.

Found: C, 65.14; H, 7.96; N, 19.27.

EXAMPLE 27

1-Bicyclo[2.2.1]hept-2-yl-7-[4-(4-methylpiperazin-1-yl)phenylamino]-3,4-dihydro-pyrimido[4,5-d]pyrimidin-2(1H)-one (exo)

To a suspension of 300 mg (0.98 mmol) of 1-bicyclo[2.2.1]hept-2-yl-7-methanesulfinyl-3,4-dihydro-pyrimido[4,5-d]pyrimidin-2(1H)-one and 374 mg (1.96 mmol) of 1-(4-aminophenyl)-4-methylpiperazine in 4.0 mL of acetonitrile is added 377 µL (4.90 mmol) of trifluoroacetic acid. The mixture is heated at 85° C. overnight. The cooled reaction mixture is diluted with ethyl acetate and washed two times with saturated aqueous sodium bicarbonate solution and once with brine. The organic phase is dried over magnesium sulfate and concentrated. The dark solid residue is triturated in 4 mL of 1:1 dichloromethane/ethyl acetate, filtered, washed with ethyl acetate, and dried to give 266 mg (63%) of the title compound: mp 251-254° C. (dec).

Analysis calculated for $C_{24}H_{31}N_7O$: C, 66.49; H, 7.21; N, 22.61.

Found: C, 66.14; H, 7.16; N, 22.22.

EXAMPLE 28

1-Methyl-7-[4-(4-methylpiperazin-1-yl)phenylamino]-3,4-dihydro-pyrimido[4,5-d]pyrimidin-2(1H)-one; compound with trifluoroacetic acid To a solution of 300 mg (1.32 mmol) of 7-methanesulfinyl-1-methyl-3,4-dihydro-pyrimido[4,5-d]pyrimidin-2(1H)-one and 507 mg (2.65 mmol) of 1-(4-aminophenyl)-4-methylpiperazine in 5 mL of acetonitrile is added 510 µL (6.6 mmol) of trifluoroacetic acid. After heating the reaction mixture at 85° C. overnight, a heavy precipitate forms. The cooled reaction mixture is diluted with 2 mL of ethyl acetate and filtered. The solids are washed three times with ethyl acetate/acetonitrile and dried to give 560 mg (84%) of the trifluoroacetate salt of the title compound: mp 234-235° C. (dec).

Analysis calculated for $C_{18}H_{23}N_7O.2.0 \ C_2HF_3O_2$: C, 45.44; H, 4.33; N, 16.77.

Found: C, 45.49; H, 4.35; N, 16.77.

EXAMPLE 29

7-[4-(4-Hydroxypiperidin-1-yl)phenylamino]-1-methyl-3,4-dihydro-pyrimido[4,5-d]pyrimidin-2(1H)-one; Compound with trifluoroacetic acid To a solution of 400 mg (1.77 mmol) of 7-methanesulfinyl-1-methyl-3,4-dihydro-pyrimido[4,5-d]pyrimidin-2(1H)-one and 680 mg (3.53 mmol) of 1-(4-aminophenyl)-4-hydroxypiperidine in 6 mL of acetonitrile is added 408 µL (5.3 mmol) of trifluoroacetic acid. After heating the reaction mixture at 85° C. overnight, a heavy precipitate forms. The cooled reaction mixture is diluted with 2 mL of ethyl acetate and filtered. The solids are washed with ethyl acetate and recrystallized from acetonitrile to give 565 mg (51%) of the trifluoroacetate salt of the title compound: mp 228-229° C. (dec).

Analysis calculated for $C_{18}H_{22}N_6O_2.2.0 \ C_2HF_3O_2.C_2H_3N$: C, 46.23; H, 4.36; N, 15.72.

Found: C, 46.55; H, 4.48; N, 15.52.

EXAMPLE 30

7-{4-[4-(Dimethylamino)piperidin-1-yl]phenylamino}-1-methyl-3,4-dihydro-pyrimido[4,5-d]pyrimidin-2(1H)-one; compound with trifluoroacetic acid To a solution of 400 mg (1.77 mmol) of 7-methanesulfinyl-1-methyl-3,4-dihydro-pyrimido[4,5-d]pyrimidin-2(1H)-one and 775 mg (3.53 mmol) of 1-(4-aminophenyl)-4-(dimethylamino)piperidine in 6 mL of acetonitrile is added 680 µL (8.8 mmol) of trifluoroacetic acid. After heating the reaction mixture at 85° C. overnight, a heavy precipitate forms. The cooled reaction mixture is diluted with 6 mL of ethyl acetate and filtered. The solids are washed with ethyl acetate and recrystallized from acetonitrile then acetonitrile/dichloromethane/trifluoroacetic acid to give 202 mg (17%) of the trifluoroacetate salt of the title compound: mp 190-191° C. (dec).

Analysis calculated for $C_{20}H_{27}N_7O.2.0 \ C_2HF_3O_2.H_2O.0.3 \ C_2H_3N.0.2 \ CH_2Cl_2$: C, 45.39; H, 4.96; N, 15.59.

Found: C, 45.37; H, 5.12; N, 15.42.

EXAMPLE 31

1-Methyl-7-[4-(pyrazol-1-yl)phenylamino]-3,4-dihydro-pyrimido[4,5-d]pyrimidin-2(1H)-one; Compound with trifluoroacetic acid To a solution of 200 mg (0.88 mmol) of 7-methanesulfinyl-1-methyl-3,4-dihydro-pyrimido[4,5-d]pyrimidin-2(1H)-one and 281 mg (1.77 mmol) of 1-(4-aminophenyl)pyrazole in 3.2 mL of acetonitrile is added 204 µL (2.65 mmol) of trifluoroacetic acid. After heating the reaction mixture at 85° C. overnight, a heavy precipitate forms. The cooled reaction mixture is diluted with 2 mL of ethyl acetate and filtered. The solids are washed with ethyl acetate to give 356 mg (93%) of the trifluoroacetate salt of the title compound: mp 250-251° C. (dec).

Analysis calculated for $C_{16}H_{15}N_7O.C_2HF_3O_2$: C. 49.66; H, 3.70; N, 22.52.

Found: C, 49.70; H, 3.60; N, 22.18.

General Procedure for Oxidation of 1-alkyl-7-[(Substituted)phenylamino]-3,4-dihydro-pyrimido[4,5-d]pyrimidin-2(1H)-ones to 1-alkyl-7-[(Substituted)phenylamino]-pyrimido[4,5-d]pyrimidin-2(1H)-ones To a room temperature solution of the 1-alkyl-7-[(substituted) phenylamino]-3,4-dihydro-pyrimido[4,5-d]pyrimidin-2(1H)-one in THF or DMSO is added 4 equivalents of potassium tert-butoxide. An oxygen atmosphere is introduced, and the solution is stirred overnight. The mixture is diluted with ethyl acetate and washed sequentially with saturated aqueous sodium bicarbonate, water, and brine. The organic phase is dried over magnesium sulfate and concentrated to give a residue that is triturated in an appropriate solvent, then the precipitated product is collected. Further purification can be carried out by standard procedures to provide a compound of Formula I.

EXAMPLE 32

1-Cyclopentyl-7-[4-(4-methylpiperazin-1-yl)phenylamino]pyrimido-[4,5-d]pyrimidin-2(1H)-one Prepared from 150 mg (0.37 mmol) of 1-cyclopentyl-7-[4-(4-methylpiperazin-1-yl)phenylamino]-3,4-dihydro-pyrimido[4,5-d]pyrimidin-2(1H)-one and 165 mg (1.47 mmol) of potassium tert-butoxide in 6 mL of THF. The dark orange semi-solid is triturated in diethyl ether, and the yellow powder is collected and dried to give 100 mg (67%) of the title compound: mp 220-225° C. (dec).

Analysis calculated for $C_{22}H_{27}N_7O$: C, 65.16; H, 6.71; N, 24.18.

Found: C, 65.22; H, 6.55; N, 23.78.

EXAMPLE 33

1-Cyclopentyl-7-[4-(4-hydroxypiperidin-1-yl)phenylamino]pyrimido[4,5-d]pyrimidin-2(1H)-one Prepared from 60 mg (0.15 mmol) of 1-cyclopentyl-7-[4-(4-hydroxypiperidin-1-yl)phenylamino]-3,4-dihydro-pyrimido[4,5-d]pyrimidin-2(1H)-one and 66 mg (0.58 mmol) of potassium tert-butoxide in 1.5 mL of DMSO. The crude semi-solid residue is triturated in 15 mL of 2:1 diethyl ether/hexane, and the orange amorphous solid is collected and dried to leave 20 mg (30%) of the title compound: mp>185° C. (dec).

MS (CI) (m+1)/z 407.

EXAMPLE 34

1-Cyclopentyl-7-{3-methyl-4-[2-(diethylamino) ethoxy]-phenylamino}pyrimido[4,5-d]pyrimidin-2 (1H)-one Prepared from 70 mg (0.16 mmol) of 1-cyclopentyl-7-{3-methyl-4-[2-(diethylamino)ethoxy]phenylamino}-3,4-dihydro-pyrimido[4,5-d]pyrimidin-2(1H)-one and 72 mg (0.58 mmol) of potassium tert-butoxide in 3.0 mL of DMSO. The crude semi-solid residue is dissolved in a mixture of tert-butyl methyl ether and hexane. The solution is allowed to evaporate slowly to less than 1 mL, then diluted with 2 mL of 1:3 diethyl ether/hexane. The precipitated solids are collected and dried to give 17 mg (24%) of the title compound: mp>95° C. (dec).

MS (CI) (m+1)/z 437 and 232.

EXAMPLE 35

1-Cyclopentyl-7-[4-(3-hydroxypiperidin-1-yl)phenylamino]pyrimido[4,5-d]-pyrimidin-2(1H)-one Prepared from 75 mg (0.18 mmol) of 1-cyclopentyl-7-[4-(3-hydroxypiperidin-1-yl)phenylamino]-3,4-dihydro-pyrimido[4,5-d]pyrimidin-2(1H)-one and 82 mg (0.73 mmol) of potassium tert-butoxide in 4.0 mL of THF. The semi-solid residue is triturated in diethyl ether, and the orange amorphous solid is collected and dried to give 35 mg (45%) of the title compound: mp>135° C. (dec).

Analysis calculated for $C_{22}H_{26}N_6O_2.0.15$ $C_2H_{10}O0.75H_2O$: C, 62.96; H, 6.78; N, 19.49.

Found: C, 62.98; H, 6.54; N, 19.47.

EXAMPLE 36

1-Cyclopentyl-7-[4-(pyrazol-1-yl)phenylamino]pyrimido[4,5-d]pyrimidin-2(1H)-one

Prepared from 100 mg (0.20 mmol) of the trifluoroacetate salt of 1-cyclopentyl-7-[4-(pyrazol-1-yl)phenylamino]-3,4-dihydro-pyrimido[4,5-d]pyrimidin-2(1H)-one and 115 mg (1.02 mmol) of potassium tert-butoxide in 5.0 mL of THF. The semi-solid residue is triturated in diethyl ether, and the orange amorphous solid is collected and dried to give 31 mg (40%) of the title compound: mp>135° C. (dec).

Analysis calculated for $C_{20}H_{19}N_7O.0.1$ $C_2H_{10}O.0.5H_2O$: C, 62.85; H, 5.43; N, 25.15.

Found: C, 63.09; H, 5.30; N, 25.04.

EXAMPLE 37

1-Cyclopentyl-7-(4-methoxyphenylamino)pyrimido [4,5-d]pyrimidin-2(1H)-one

Reaction of 1-cyclopentyl-7-(4-methoxyphenylamino)-3,4-dihydro-pyrimido[4,5-d]pyrimidin-2(1H)-one by the general procedure described above gives the title compound.

MS (CI) (m+1)/z 338.

EXAMPLE 38

1-Cyclopentyl-7-[4-(piperidin-1-yl)phenylamino] pyrimido [4,5-d]pyrimidin-2(1H)-one Reaction of 1-cyclopentyl-7-[4-(piperidin-1-yl)phenylamino]-3,4-dihydro-pyrimido[4,5-d]pyrimidin-2(1H)-one by the general procedure described above gives the title compound.

MS (CI) (m+1)/z 391.

EXAMPLE 39

1-Cyclopentyl-7-[4-(2-(morpholin-1-yl)ethyl)piperidin-1-yl)phenylamino]-pyrimido[4,5-d]pyrimidin-2(1H)-one Prepared from 37 mg (0.07 mmol) of 1-cyclopentyl-7-[4-(2-(morpholin-1-yl)ethyl)piperidin-1-yl)phenylamino]-3,4-dihydro-pyrimido[4,5-d]pyrimidin-2(1H)-one and 33 mg (0.29 mmol) of potassium tert-butoxide in 2.0 mL of THF. The semi-solid residue is triturated in diethyl ether, and the orange amorphous solid is collected and dried to give 11.8 mg (32%) of the title compound: mp>140° C. (dec).
MS (CI) (m+1)/z 504.

EXAMPLE 40

1-Isopropyl-7-[4-(4-methylpiperazin-1-yl)phenylamino]pyrimido[4,5-d]pyrimidin-2(1H)-one Prepared from 200 mg (0.52 mmol) of 1-isopropyl-7-[4-(4-methylpiperazin-1-yl)phenylamino]-3,4-dihydro-pyrimido[4,5-d]pyrimidin-2(1H)-one and 235 mg (2.10 mmol) of potassium tert-butoxide in 10 mL of tetrahydrofuran. The semi-solid is triturated in 14 mL of 1:1 diethyl ether/hexane, and the powder is collected and dried to give 135 mg (68%) of the title compound:
mp 228-229° C. (dec).
Analysis calculated for $C_{20}H_{25}N_7O.0.03\ C_6H_{14}.0.5H_2O$: C, 61.98; H, 6.81; N, 25.07.
Found: C, 61.95; H, 6.73; N, 25.04.

EXAMPLE 41

7-{4-[4-(Dimethylamino)piperidin-1-yl]phenylamino}-1-isopropyl-pyrimido[4,5-d]pyrimidin-2(1H)-one Prepared from 200 mg (0.31 mmol) of 7-{4-[4-(dimethylamino)piperidin-1-yl]phenylamino}-1-isopropyl-3,4-dihydro-pyrimido[4,5-d]pyrimidin-2(1H)-one, trifluoroacetic acid and 211 mg (1.88 mmol) of potassium tert-butoxide in 7 mL of tetrahydrofuran. The reaction mixture is stirred for 48 hours, and the workup is done as described in the general procedure, then the reaction is repeated for 72 hours. After the workup, the semi-solid is triturated in diethyl ether, and the powder is collected and dried to give 24 mg (18%) of the title compound:
mp>100° C. (dec).
Analysis calculated for $C_{22}H_{29}N_7O.H_2O.0.1\ CH_2Cl_2$: C, 61.16; H, 7.25; N, 22.59.
Found: C, 61.11; H, 6.98; N, 22.49.

EXAMPLE 42

1-Isopropyl-7-[4-(pyrazol-1-yl)phenylamino]pyrimido[4,5-d]pyrimidin-2(1H)-one

Prepared from 150 mg (0.32 mmol) of 1-isopropyl-7-[4-(pyrazol-1-yl)phenylamino]-3,4-dihydro-pyrimido[4,5-d]pyrimidin-2(1H)-one, trifluoroacetic acid and 218 mg (1.94 mmol) of potassium tert-butoxide in 10 mL of tetrahydrofuran. The reaction mixture is stirred for 48 hours, 50 mg (0.44 mmol) of potassium tert-butoxide is added, and the reaction is continued for 72 hours. After the workup, the semi-solid is triturated in diethyl ether, and the powder is collected and dried to give 86 mg (73%) of the title compound: mp 243-247° C. (dec).
Analysis calculated for $C_{18}H_7N_7O.0.75H_2O.0.5\ C_4H_{10}O$: C, 60.05; H, 5.42; N, 26.36.
Found: C, 60.19; H, 5.36; N, 26.09.

EXAMPLE 43

1-Isopropyl-7-{4-[4-(3-(morpholin-4-yl)propyl)piperidin-1-yl]phenylamino}-pyrimido[4,5-d]pyrimidin-2(1H)-one Prepared from 100 mg (0.20 mmol) of 1-isopropyl-7-{4-[4-(3-(morpholin-4-yl)propyl)piperidin-1-yl]phenylamino}-3,4-dihydro-pyrimido[4,5-d]pyrimidin-2(1H)-one and 88.5 mg (0.79 mmol) of potassium tert-butoxide in 10 mL of tetrahydrofuran. The reaction mixture is stirred overnight, 88.5 mg (0.79 mmol) of potassium tert-butoxide is added, and the reaction is continued for 48 hours. After the workup, the semi-solid is five times suspended in diethyl ether and rotovapped to dryness to give 87 mg (85%) of the title compound: mp>95° C. (dec).
Analysis calculated for $C_{18}H_{17}N_7O.0.8H_2O_{.0.1}\ C_4H_{10}O$: C, 64.09; H, 7.77; N, 19.10.
Found: C, 64.02; H, 7.50; N, 19.08.

EXAMPLE 44

1-Bicyclo [2.2.1]hept-2-yl-7-[4-(4-methylpiperazin-1-yl)phenylamino]-pyrimido[4,5-d]pyrimidin-2(1H)-one, exo Prepared from 200 mg (0.46 mmol) of 1-bicyclo[2.2.1]hept-2-yl-7-[4-(4-methylpiperazin-1-yl)phenylamino]-3,4-dihydro-pyrimido[4,5-d]pyrimidin-2(1H)-one, exo and 207 mg (1.84 mmol) of potassium tert-butoxide in 10 mL of tetrahydrofuran. The reaction mixture is stirred for 48 hours. After the workup, the semi-solid is triturated in diethyl ether/hexane, and the powder is collected and dried to give 140 mg (70%) of the title compound: mp>210° C. (dec).
Analysis calculated for $C_{24}H_{29}N_7O.0.5H_2O$: C, 65.43; H, 6.86; N, 22.26.
Found: C, 65.29; H, 6.74; N, 21.90.

EXAMPLE 45

1-Methyl-7-[4-(4-methylpiperazin-1-yl)phenylamino]pyrimido[4,5-d]pyrimidin-2(1H)-one Prepared from 250 mg (0.50 mmol) of 1-methyl-7-[4-(4-methylpiperazin-1-yl)phenylamino]-3,4-dihydro-pyrimido[4,5-d]pyrimidin-2(1H)-one, trifluoroacetic acid and 336 mg (2.99 mmol) of potassium tert-butoxide in 12 mL of tetrahydrofuran. The reaction mixture is stirred for 48 hours. After the workup, the semi-solid is triturated in diethyl ether, and the powder is collected and dried to give 110 mg (61%) of the title compound: mp 259-260° C. (dec).
Analysis calculated for $C_{18}H_{21}N_7O.0.4H_2O$: C, 60.29; H, 6.13; N, 27.34.
Found: C, 60.54; H, 5.99; N, 27.05.

EXAMPLE 46

7-{4-[4-(Dimethylamino)piperidin-1-yl]phenylamino}-1-methyl-pyrimido[4,5-d]pyrimidin-2(1H)-one Prepared from 170 mg (0.26 mmol) of 7-{4-[4-(dimethylamino)piperidin-1-yl]phenylamino}-1-methyl-3,4-dihydro-pyrimido[4,5-d]pyrimidin-2(1H)-one, trifluoroacetic acid and 233 mg (2.07 mmol) of potassium tert-butoxide in 20 mL of tetrahydrofuran. The reaction mixture is stirred for 6 days, and the workup is done as described in the general procedure, including a back-extraction of the combined aqueous phase with chloroform. The combined organic phase was dried over magnesium sulfate, filtered, and concentrated. The semi-solid is triturated in diethyl ether/hexane, and the powder is collected and dried to give 64 mg (60%) of the title compound: mp 198-202° C. (dec).

Analysis calculated for $C_{20}H_{25}N_7O.1.7H_2O$: C, 58.58; H, 6.98; N, 23.91.

Found: C, 58.73; H, 6.71; N, 23.92.

EXAMPLE 47

1-Methyl-7-[4-(pyrazol-1-yl)phenylamino]pyrimido[4,5-d]pyrimidin-2(1H)-one

Prepared from 200 mg (0.46 mmol) of 1-methyl-7-[4-(pyrazol-1-yl)phenylamino]-3,4-dihydro-pyrimido[4,5-d]pyrimidin-2(1H)-one, trifluoroacetic acid and 309 mg (2.76 mmol) of potassium tert-butoxide in 15 mL of tetrahydrofuran. The reaction mixture is stirred overnight. After the workup, the semi-solid is triturated in diethyl ether, and the powder is collected and dried to give 102 mg (65%) of the title compound: mp>290° C. (dec).

Analysis calculated for $C_{16}H_{13}N_7O.0.4H_2O.0.2\ C_4H_{10}O$: C, 59.11; H, 4.67; N, 28.72.

Found: C, 59.42; H, 4.39; N, 28.46.

Examples 48-65 are specific embodiments of the general reaction schemes shown in Scheme 2.

EXAMPLE 48

5-[(3,5-Dimethoxy-phenylimino)-methyl]-2-methylsulfanyl-pyrimidin-4-ylamine

To a suspension of 4.36 g (23.7 mmol) of 4-amino-2-methylsulfanyl-pyrimidine-5-carbaldehyde (made as described in WO 98/33798) and 3.65 g (23.7 mmol) of 3,5-dimethoxyaniline in 165 mL of water was added 4.5 mL of glacial acetic acid. The reaction was stirred at 25° C. overnight and filtered. The filter pad was washed with water, and the filtrate was dried in vacuo to give 7.02 g (96%) of the title compound, which was used as is in the next step.

MS (APCI) (m+1)/z 305.1.

EXAMPLE 48a

{5-[(3,5-Dimethoxy-phenylimino)-methyl]-2-methylsulfanyl-pyrimidin-4-yl}-ethyl-amine To a stirred suspension of 4-ethylamino-2-methylsulfanyl-pyrimidine-5-carbaldehyde (5.0 g, 25.09 mmol, made by the method described in J. Med. Chem., 1998; 41(17):3276-3292) and 3,5-dimethoxyaniline (3.84 g, 25.09 mmol) water (190 mL) was added glacial acetic acid (5 mL). The reaction mixture was stirred at ambient temperature for 24 hours and the suspension filtered. The insoluble product was dried on the filter to afford 7.79 g (92%) of the titled compound: mp 100-105° C.

Mass Spectrum (APCI, 80/20 $CH_3CN/H_2O$, Probe=450° C.) (m+1)/z 333.1

Analysis calculated for $C_{16}H_{20}N_4O_2S_1$: C, 57.81; H, 6.06; N, 16.85.

Found: C, 57.63; H, 6.06; N, 16.86.

EXAMPLE 49

5-[(3,5-Dimethoxy-phenylamino)-methyl]-2-methylsulfanyl-pyrimidin-4-ylamine

Into 18.2 mL (18.2 mmol) of a 1 M solution of lithium aluminum hydride (LAH) in tetrahydrofuran (THF) cooled to 5° C. was added a solution of 5.55 g (18.3 mmol) of 5-[(3,5-dimethoxy-phenylimino)-methyl]-2-methylsulfanyl-pyrimidin-4-ylamine in 94 mL of dry THF over 20 minutes. The reaction was stirred for 1.5 hours at 5° C., then quenched by slow sequential addition of 0.72 mL of water, 3.0 mL of 25% NaOH, and an additional 1.66 mL of water. The reaction mixture was filtered through Celite, and the filter pad was washed well with THF. The filtrate was concentrated to dryness in vacuo. The residue was dissolved in ethyl acetate. The ethyl acetate solution was washed three times with a solution of saturated sodium chloride, dried over magnesium sulfate, and concentrated in vacuo to give 5.10 g (91%) of the title compound.

Analysis calculated for $C_{14}H_{18}N_4O_2S$: C, 54.88; H, 5.92; N, 18.29; S, 10.47.

Found: C, 54.92; H, 5.93; N, 18.32; S, 10.68.

EXAMPLE 49a

{5-[4-(3,5-Dimethoxy-phenylamino)-methyl]-2-methylsulfanyl-pyrimidin-4-yl}-ethyl-amine To a solution of {5-[(3,5-dimethoxy-phenylimino)-methyl]-2-methylsulfanyl-pyrimidin-4-yl}-ethyl-amine (5.91 g, 17.78 mmol) in dry THF (100 mL) at 5° C. was added dropwise 17.78 mL of a 1 M solution of LAH in THF over a period of 20 minutes. The reaction mixture was stirred at 5° C. for 1 hour and then quenched in the following order with the dropwise addition of 0.8 mL of water, 3.2 mL of 25% NaOH, and 1.8 mL of water. The reaction mixture was partitioned between one-half saturated brine and EtOAc. The organic layer was separated, washed with water, dried over magnesium sulfate, filtered, and evaporated. The residue was purified by column chromatography eluting with a solvent gradient of 1% to 3% methanol in dichloromethane to give 5.4 g (91%) of the titled compound: Mass Spectrum (APCI, 80/20 $CH_3CN/H_2O$, Probe=450° C.) (m+1)/z 335.2

Analysis calculated for $C_{16}H_{22}N_4O_2S_1$: C, 57.46; H, 6.63; N, 16.75.

Found: C, 57.75; H, 6.62; N, 16.52.

EXAMPLE 50

3-(3,5-Dimethoxy-phenyl)-7-methylsulfanyl-3,4-dihydro-pyrimido[4,5-d]pyrimidin-2(1H)-one Into a solution of 5.0 g (16.3 mmol) of 5-[(3,5-dimethoxy-phenylamino)-methyl]-2-methylsulfanyl-pyrimidin-4-ylamine in 55 mL of dimethylformamide cooled to 5° C., was added 1.63 g (40.8 mmol) of sodium hydride as a 60% mineral oil suspension. The ice bath was removed, and the reaction was stirred for 1 hour. To the reaction was then added 7.94 g (48.9 mmol) of 1,1'-carbonyldiimidazole. After stirring the mixture a further 2.5 hours, the mixture was concentrated in vacuo. The residue was partitioned between dichloromethane and a saturated solution of ammonium chloride. The dichloromethane layer was washed twice with each of saturated ammonium chloride, water, and a saturated solution of sodium chloride. The dichloromethane solution was dried over magnesium sulfate and concentrated in vacuo. The residue was chromatographed on silica gel, eluting with chloroform/methanol (10:0.25 v/v), to give 3.24 g (60%) of the title compound.

MS (APCI) (m+1)/z 333.2

EXAMPLE 50a 3-(3,5-Dimethoxy-phenyl)-1-ethyl-7-methylsulfanyl-3,4-dihydro-pyrimido[4,5-d]pyrimidin-2(1H)-one To a solution of {5-[4-(3,5-dimethoxy-phenylamino)-methyl]-2-methylsulfanyl-pyrimidin-4-yl}-ethyl-amine (6.42 g, 19.2 mmol) and diisopropyl ethylamine (4.96 g, 38.39 mmol) in dichloromethane (120 mL) at 5° C. was added dropwise 10 mL of a 20% solution of phosgene in toluene over a period of 20 minutes. The reaction mixture was allowed to warm to ambient temperature and stirred for 4 hours. The mixture was washed with one-half saturated $NaHCO_3$ and water, then dried over magnesium sulfate and filtered. The filtrate was evaporated under reduced pressure and the residue purified by column chromatography, eluting with a solvent gradient of 1% to 3% methanol in dichloromethane to afford 5.96 g (86%) of the titled compound: mp 134-136° C. Mass Spectrum (APCI, 80/20 $CH_3CN/H_2O$, Probe=450° C.) (m+1)/z 361.2

Analysis calculated for $C_{17}H_{20}N_4O_3S$: C, 56.65; H, 5.59; N, 15.54.

Found: C, 56.49; H, 5.54; N, 15.33.

EXAMPLE 51

3-(3,5-Dimethoxy-phenyl)-7-methanesulfinyl-3,4-dihydro-pyrimido [4,5-d]pyrimidin-2(1H)-one Into a solution of 2.0 g (6.02 mmol) of 3-(3,5-dimethoxy-phenyl)-7-methylsulfanyl-3,4-dihydro-pyrimido[4,5-d]pyrimidin-2(1H)-one in 450 mL chloroform was added 1.73 g (6.62 mmol) of trans-2-(phenylsulfonyl)-3-phenyloxaziridine. The reaction was stirred at room temperature overnight, then concentrated in vacuo. The residue was chromatographed down silica gel, eluting first with chloroform, then with a solution of chloroform/methanol (10/0.25 v/v), and finally chloroform/methanol (9:1 v/v), giving 1.87 g (85%) of the title compound: mp 220-222° C.

Analysis calculated for $C_{15}H_{16}N_4O_4S \cdot 0.30 H_2O \cdot 0.10 CHCl_3$: C, 49.59; H, 4.60; N, 15.32; S, 8.77; $H_2O$, 1.48.

Found: C, 49.62; H, 4.34; N, 15.20; S, 8.87; $H_2O$, 1.42.

EXAMPLE 51a 3-(3,5-Dimethoxy-phenyl)-1-ethyl-7-methanesulfinyl-3,4-dihydro-pyrimido[4,5-d]pyrimidin-2(1H)-one To a solution of 3-(3,5-dimethoxy-phenyl)-1-ethyl-7-methylsulfanyl-3,4-dihydro-pyrimido[4,5-d]pyrimidin-2(1H)-one (5.61 g, 15.57 mmol) in dichloromethane (100 mL) at ambient temperature was added 3-phenyl-2-(phenylsulfonyl)oxaziridine (4.88 g, 18.69 mmol, PD 0191006, Org. Synth., 1987; 66:203-210) in portions. The reaction mixture was stirred overnight, then washed with brine and water. The organic layer was dried over magnesium sulfate, filtered, and evaporated under reduced pressure. The residue was purified by column chromatography eluting with a solvent mixture of 3% methanol in dichloromethane to yield 4.6 g (78%) of the titled compound: mp 167-169° C. Mass Spectrum (APCI, 80/20 $CH_3CN/H_2O$, Probe=450° C.) (m+1)/z 377.1

Analysis calculated for $C_{17}H_{20}N_4O_3S$: C, 54.24; H, 5.36; N, 14.88.

Found: C, 53.95; H, 5.27; N, 14.51.

EXAMPLE 52

7-(4-Diethylamino-butylamino)-3-(3,5-dimethoxy-phenyl)-3,4-dihydro-pyrimido[4,5-d]pyrimidin-2(1H)-one A suspension of 0.2261 g (0.65 mmol) of 3-(3,5-dimethoxy-phenyl)-7-methanesulfinyl-3,4-dihydro-pyrimido[4,5-d]pyrimidin-2(1H)-one and 0.103 g (0.71 mmol) of diethylaminobutylamine in 10 mL of dry dioxane was warmed to 60° C. and stirred overnight. To the reaction mixture was added 0.306 g (2.13 mmol) of diethylaminobutylamine and 0.1658 g (0.71 mmol) of camphorsulfonic acid. The reaction mixture was stirred for another 18 hours at 60° C. The reaction solution was concentrated in vacuo, and the residue was partitioned between ethyl acetate and a saturated solution of sodium bicarbonate. The ethyl acetate layer was washed with a saturated solution of sodium bicarbonate, then with water, dried over magnesium sulfate, and concentrated in vacuo. The residue was chromatographed down silica gel, eluting with ethyl acetate/ethanol/triethylamine (9:2:1 v/v/v) to give 0.173 g (62%) of the title compound: mp 203-207° C.

Analysis calculated for $C_{22}H_{32}N_6O_3$: C. 61.66; H, 7.53; N, 19.61.

Found: C, 61.31; H, 7.32; N, 19.23.

EXAMPLE 53

7-(4-Diethylamino-butylamino)-3-(3,5-dimethoxy-phenyl)-1-ethyl-3,4-dihydro-pyrimido[4,5-d]pyrimidin-2(1H)-one A mixture of 3-(3,5-dimethoxy-phenyl)-1-ethyl-7-methanesulfinyl-3,4-dihydro-pyrimido[4,5-d]pyrimidin-2(1H)-one (0.5 g, 1.33 mmol), 4-diethylaminobutylamine (0.38 g, 2.66 mmol,) and trifluoroacetic acid (0.31 g, 2.66 mmol) in acetonitrile (6 mL) was heated in a sealed tube at 90° C. for 18 hours. The solvent was removed under reduced pressure and the residue taken up in 1N HCl. The solution was made basic with 50% NaOH and extracted twice with dichloromethane. The combined organic layers were dried over magnesium sulfate, filtered, and evaporated. The residue was purified by radial chromatography eluting with a solvent mixture of ethyl acetate/methanol/ethyl (89:10:1 v/v/v) to give 0.34 g (56%) of the titled compound: mp 83-85° C. Mass Spectrum (APCI, 80/20 $CH_3CN/H_2O$, Probe=450° C.) (m+1)/z 458.2

Analysis calculated for $C_{24}H_{36}N_6O_3$: C, 63.13; H, 7.95; N, 8.41.

Found: C, 62.85; H, 7.84; N, 18.06.

EXAMPLE 53a

7-[4-(2-Diethylamino-ethoxy)-phenylamino]-3-(3,5-dimethoxy-phenyl)-1-ethyl-3,4-dihydro-pyrimido[4,5-d]pyrimidin-2(1H)-one A mixture of 3-(3,5-dimethoxy-phenyl)-1-ethyl-7-methanesulfinyl-3,4-dihydro-pyrimido[4,5-d]pyrimidin-2(1H)-one (0.5 g, 1.33 mmol), 4-(2-diethylaminoethoxy)aniline (0.55 g, 2.66 mmol, Helv. Chim. Acta, 1960; 43:1971-1979) and trifluoroacetic acid (0.46 g, 3.98 mmol) in acetonitrile (6 mL) was heated in a sealed tube at 100° C. for 18 hours. The solvent was removed under reduced pressure and the residue dissolved in water. The solution was made basic with 1N NaOH and extracted twice with EtOAc. The combined organic layers were dried over magnesium sulfate, filtered, and evaporated. The residue was suspended in ether (20 mL), triethylamine (0.27 g, 2.66 mmol), and $BOC_2O$ (0.32 g, 1.46 mmol) added, and the mixture stirred at ambient temperature for 4 hours. The reaction mixture was diluted with hexane and cooled to 0° C. The insoluble product was collected by filtration and washed with hexane to afford 0.56 g (81%) of the titled compound: mp 139-141° C. Mass Spectrum (APCI, 80/20 $CH_3CN/H_2O$, Probe=450° C.) (m+1)/z 521.3

Analysis calculated for $C_{28}H_{36}N_6O_4 \cdot 0.19\ CF_3CO_2H$: C, 62.86; H, 6.73; N, 15.50.

Found: C, 62.85; H, 6.65; N, 15.56.

General Experimental for the Parallel Synthesis of 3-Aryl-7-(Substituted alkylamino)-3,4-dihydro-pyrimido[4,5-d]pyrimidin-2(1H)-ones and 3-Aryl-1-alkyl-7-(Substituted alkylamino)-3,4-dihydro-pyrimido[4,5-d]pyrimidin-2(1H)-ones Into an Argonaut Technologies' Quest 210 10 mL reactor was added 0.100 g (0.287 mmol) of 3-(3,5-dimethoxy-phenyl)-7-methanesulfinyl-3,4-dihydro-pyrimido[4,5-d]pyrimidin-2(1H)-one in 5 mL of dry dioxane or 0.100 g (0.266 mmol) or 3-(3,5-dimethoxy-phenyl)-1-ethyl-7-methanesulfinyl-3,4-dihydro-pyrimido[4,5-d]pyrimidin-2(1H)-one in 4 mL of dry dioxane and 0.0753 g (0.3157 mmol) of camphorsulfonic acid in 2 mL of dry dioxane. To the reaction mixture was added a solution of from 2.7 to 3.3 equivalents of amine ($R^1NH_2$) in 1 mL dioxane. The reaction mixture was agitated at 65° C. for 18 hours, then cooled to room temperature. The dioxane was evaporated under a stream of nitrogen, and the residue was partitioned between ethyl acetate and a solution of saturated sodium bicarbonate. The ethyl acetate layer was washed twice with a dilute solution of sodium bicarbonate, then once with water. The ethyl acetate layer was dried with magnesium sulfate and concentrated to dryness using a stream of nitrogen. The residue was chromatographed down silica gel giving the title compound.

EXAMPLE 54

3-(3,5-Dimethoxy-phenyl)-7-{2-[(pyridin-4-ylmethyl)-amino]-ethylamino}-3,4-dihydro-pyrimido[4,5-d]pyrimidin-2(1H)-one Using the general procedure above, 3-(3,5-dimethoxy-phenyl)-7-methanesulfinyl-3,4-dihydro-pyrimido[4,5-d]pyrimidin-2(1H)-one and 0.1423 g (0.941 mmol) of N-(4-picoly)ethylenediamine were reacted. The residue was chromatographed eluting with ethyl acetate/ethanol/triethylamine (9:2:1 v/v/v) then ethyl acetate/ethanol/triethylamine (9:3:2 v/v/v) to give 0.0162 g (13%) of the title compound: HPLC=92% pure.

MS (APCI) (m+1)/z 436.2

EXAMPLE 54a 3-(3,5-Dimethoxy-phenyl)-7-[3-(4-methyl-piperazin-1-yl)-propylamino]-3,4-dihydro-1H-pyrimido[4,5-d]pyrimidin-2(1H)-one Using the general procedure above, 3-(3,5-dimethoxy-phenyl)-7-methanesulfinyl-3,4-dihydro-pyrimido[4,5-d]pyrimidin-2(1H)-one and 0.1234 g (0.785 mmol) of 3-(4-methyl-piperazin-1-yl)-propylamine were reacted. The residue was chromatographed over silica gel, eluting with ethyl acetate/ethanol/triethylamine (9:2:1 v/v/v), then ethyl acetate/ethanol/triethylamine (9:3:2 v/v/v) to give 0.0443 g (35%) of the title compound: HPLC=92% pure.

MS (APCI) (m+1)/z 442.2

EXAMPLE 54b 3-(3,5-Dimethoxy-phenyl)-7-[4-(4-methyl-piperazin-1-yl)-butylamino]-3,4-dihydro-pyrimido[4,5-d]pyrimidin-2(1H)-one Using the general procedure above, 3-(3,5-dimethoxy-phenyl)-7-methanesulfinyl-3,4-dihydro-pyrimido[4,5-d]pyrimidin-2(1H)-one and 0.1354 g (0.791 mmol) of 4-(4-methyl-piperazin-1-yl)-butylamine were reacted. The residue was chromatographed over silica gel, eluting with ethyl acetate/ethanol/triethylamine (9:2:1 v/v/v) then ethyl acetate/ethanol/triethylamine (9:3:2 v/v/v) to give 0.0401 g (31%) of the title compound: HPLC=99% pure.

MS (APCI) (m+1)/z 456.2

EXAMPLE 54c 3-(3,5-Dimethoxy-phenyl)-7-[5-(4-methyl-piperazin-1-yl)-pentylamino]-3,4-dihydro-pyrimido[4,5-d]pyrimidin-2(1H)-one Using the general procedure above, 3-(3,5-dimethoxy-phenyl)-7-methanesulfinyl-3,4-dihydro-pyrimido[4,5-d]pyrimidin-2(1H)-one and 0.1475 g (0.805 mmol) of 5-(4-methyl-piperazin-1-yl)-pentylamine were reacted. The residue was chromatographed over silica gel, eluting with ethyl acetate/ethanol/triethylamine (9:2:1 v/v/v) then ethyl acetate/ethanol/triethylamine (9:3:2 v/v/v) to give 0.0322 g (24%) of the title compound: HPLC=97% pure.

MS (APCI) (m+1)/z 470.2

EXAMPLE 55

7-(3-Diethylamino-propylamino)-3-(3,5-dimethoxy-phenyl)-3,4-dihydro-pyrimido[4,5-d]pyrimidin-2(1H)-one Using the general procedure above, 3-(3,5-dimethoxy-phenyl)-7-methanesulfinyl-3,4-dihydro-pyrimido[4,5-d]pyrimidin-2(1H)-one and 0.1121 g (0.861 mmol) of diethylaminopropylamine were reacted. The residue was chromatographed eluting with acetonitrile/ethanol/triethylamine (8:1:0.5 v/v/v) to give 0.0476 g (40%) of the title compound: HPLC=89% pure.

MS (APCI) (m+1)/z 415.2

EXAMPLE 56

3-(3,5-Dimethoxy-phenyl)-1-ethyl-7-{2-[(pyridin-4-ylmethyl)-amino]-ethylamino}-3,4-dihydro-pyrimido[4,5-d]pyrimidin-2(1H)-one Using the general procedure above, 3-(3,5-dimethoxyphenyl)-1-ethyl-7-methanesulfinyl-3,4-dihydro-pyrimido[4,5-d]pyrimidin-2(1H)-one and 0.1317 g (0.871 mmol) of N-(4-picolyl)ethylenediamine were reacted. The residue was chromatographed over silica gel, eluting with ethyl acetate/ethanol/triethylamine (9:2:1 v/v/v), to give 0.0307 g (25%) of the title compound: HPLC=87% pure.
MS (APCI) (m+1)/z 464.2

EXAMPLE 57

3-(3,5-Dimethoxy-phenyl)-1-ethyl-7-[3-(4-methyl-piperazin-1-yl)-propylamino]-3,4-dihydro-pyrimido[4,5-d]pyrimidin-2(1H)-one Using the general procedure above, 3-(3,5-dimethoxyphenyl)-1-ethyl-7-methanesulfinyl-3,4-dihydro-pyrimido[4,5-d]pyrimidin-2(1H)-one and 0.1142 g (0.726 mmol) of 3-(4-methyl-piperazin-1-yl)-propylamine were reacted. The residue was chromatographed over silica gel, eluting with ethyl acetate/ethanol/triethylamine (9:2:1 v/v/v), to give 0.0712 g (57%) of the title compound: HPLC=96% pure.
MS (APCI) (m+1)/z 470.2

EXAMPLE 58

3-(3,5-Dimethoxy-phenyl)-1-ethyl-7-[4-(4-methyl-piperazin-1-yl)-butylamino]-3,4-dihydro-pyrimido[4,5-d]pyrimidin-2(1H)-one Using the general procedure above, 3-(3,5-dimethoxyphenyl)-1-ethyl-7-methanesulfinyl-3,4-dihydro-pyrimido[4,5-d]pyrimidin-2(1H)-one and 0.1253 g (0.732 mmol) of 4-(4-methyl-piperazin-1-yl)-butylamine were reacted. The residue was chromatographed over silica gel, eluting with ethyl acetate/ethanol/triethylamine (9:2:1 v/v/v), to give 0.0527 g (41%) of the title compound: HPLC=94% pure.
MS (APCI) (m+1)/z 484.3

EXAMPLE 59

3-(3,5-Dimethoxy-phenyl)-1-ethyl-7-[5-(4-methyl-piperazin-1-yl)-pentylamino]-3,4-dihydro-pyrimido[4,5-d]pyrimidin-2(1H)-one Using the general procedure above, 3-(3,5-dimethoxyphenyl)-1-ethyl-7-methanesulfinyl-3,4-dihydro-pyrimido[4,5-d]pyrimidin-2(1H)-one and 0.1365 g (0.745 mmol) of 5-(4-methyl-piperazin-1-yl)-pentylamine were reacted. The residue was chromatographed over silica gel, eluting with ethyl acetate/ethanol/triethylamine (9:2:1 v/v/v), to give 0.041 g (31%) of the title compound:
HPLC=98% pure.
MS (APCI) (m+1)/z 498.3

EXAMPLE 60

7-(3-Diethylamino-propylamino)-3-(3,5-dimethoxy-phenyl)-1-ethyl-3,4-dihydro-pyrimido[4,5-d]pyrimidin-2(1H)-one Using the general procedure above, 3-(3,5-dimethoxyphenyl)-1-ethyl-7-methanesulfinyl-3,4-dihydro-pyrimido[4,5-d]pyrimidin-2(1)-one and 0.1038 g (0.797 mmol) of diethylaminopropylamine were reacted. The residue was chromatographed over silica gel, eluting with acetonitrile/ethanol/triethylamine (8:1:0.5 v/v/v), to give 0.0719 g (61%) of the title compound: HPLC=81% pure.
MS (APCI) (m+1)/z 443.2

Preparation 11

2-Chloro-3,5-dimethoxy-benzoic acid

Into a solution of 12 g (52.0 mmol) of 2-chloro-3,5-dimethoxy-benzoic acid methyl ester (prepared according to the method of T. R. Kasturi and E. M. Abraham, *Indian Journal of Chemistry*, 1973; 11:1099-1104) in 40 mL of methanol was added 60 mL (60 mmol) of 1N potassium hydroxide solution. After stirring overnight at room temperature, the methanol was removed in vacuo, and the residue was suspended in 800 mL of water. The aqueous layer was extracted three times with diethyl ether and the acidified with concentrated hydrochloric acid to a pH of 3. The resulting white solid was filtered, washed well with water, and air-dried to give 9.82 g (87%) of the title compound.
MS (APCI) (m+1)/z 217

Preparation 12

(2-Chloro-3,5-dimethoxy-phenyl)-carbamic acid, tert-butyl ester

Into a solution of 9.57 g (44.18 mmol) of 2-chloro-3,5-dimethoxy-benzoic acid and 4.78 g (47.3 mmol) of triethylamine in 250 mL of toluene was added 13.57 g (49.3 mmol) diphenylphosphoryl azide. The reaction was refluxed for 4 hours. To the reaction was added 3.63 g (49.0 mmol) of tert-butanol. The reaction was refluxed overnight then concentrated in vacuo. The residue was partitioned between a cold 1N solution of citric acid and ethyl acetate. The ethyl acetate layer was washed twice with each of the following: cold IN citric acid solution, water, and then saturated sodium bicarbonate solution. The ethyl acetate layer was dried with magnesium sulfate and concentrated in vacuo. The residue was dissolved in tetrahydrofuran, added silica gel and concentrated to dryness. The residue was chromatographed on silica gel, eluting with hexane/diethyl ether (9:1 v/v), to give 8.14 g (64%) of the title compound: mp 94.5-95.5° C.

Analysis calculated for $C_{13}H_{18}NO_4Cl$: C, 54.26; H, 6.31; N, 4.87; Cl, 12.32.

Found: C, 54.20; H, 6.17; N, 4.90; Cl, 12.08.

Preparation 13

2-Chloro-3,5-dimethoxy-phenylamine

To 6.01 g (0.021 mmol) of (2-chloro-3,5-dimethoxy-phenyl)-carbamic acid tert-butyl ester was added 15 mL of trifluoroacetic acid. The reaction was stirred for 3 hours at room temperature, then concentrated in vacuo. The residue was made basic with a saturated solution of sodium bicarbonate, then extracted three times with dichloromethane. The combined dichloromethane layers were dried with magnesium sulfate and concentrated in vacuo to give 3.98 g of the title compound, which was used as is in the following example.
MS (APCI) (m+1)/z 188

EXAMPLE 61

{5-[(2-Chloro-3,5-dimethoxy-phenylimino)-methyl]-2-methylsulfanyl-pyrimidin-4-yl}-ethyl-amine Into a solution of 3.78 g (20.2 mmol) of 2-chloro-3,5-dimethoxy-phenylamine in 110 mL of toluene was added 3.97 g (20.15 mmol) of 4-ethylamino-2-methylsulfanyl-pyrimidine-5-carbaldehyde. The reaction vessel was equipped with a Dean-Stark trap, and the reaction was warmed to reflux. After 3 hours, two drops of concentrated sulfuric acid were added to the reaction. The reaction was refluxed overnight then concentrated in vacuo to give 7.36 g (93%) of the title compound, which was used as is in the following example:

mp 196.5-198.5° C.

MS (APCI) (m+1)/z 367.0

EXAMPLE 62

{5-[(2-Chloro-3,5-dimethoxy-phenylamino)-methyl]-2-methylsulfanyl-pyrimidin-4-yl}-ethyl-amine Into a suspension of 6.96 g (18.97 mmol) of {5-[(2-chloro-3,5-dimethoxy-phenylimino)-methyl]-2-methylsulfanyl-pyrimidin-4-yl}-ethyl-amine in 200 mL of dry THF cooled to 5° C. was added 18.97 mL (18.97 mmol) of a 1 M solution of LAH in THF. After stirring for 1 hour, the cold reaction was quenched by sequential addition of 0.8 mL of water, 3.0 mL of 25 NaOH, and 1.7 mL of water. The reaction was filtered through Celite, the filter pad washed well with THF, and the filtrate concentrated in vacuo. The residue was dissolved in dichloromethane, added silica gel, and concentrated in vacuo. This residue was chromatographed on silica gel, eluting with hexane/ethyl acetate (2:1 v/v), giving 5.15 g (74%) of the title compound: mp 116.5-118.5° C.

Analysis calculated for $C_{16}H_{21}N_4O_2ClS$: C, 52.10; H, 5.74; N, 15.19; Cl, 9.61; S, 8.69.

Found: C, 52.45; H, 5.67; N, 14.99; Cl, 9.38; S, 8.66.

EXAMPLE 63

3-(2-Chloro-3,5-dimethoxy-phenyl)-1-ethyl-7-methylsulfanyl-3,4-dihydro-pyrimido[4,5-d]pyrimidin-2(1H)-one Into a solution of 1.00 g (2.71 mmol) of {5-[(2-chloro-3,5-dimethoxy-phenylamino)-methyl]-2-methylsulfanyl-pyrimidin-4-yl}-ethyl-amine in 7 mL of dry DMF cooled to 5° C. was added 0.271 g (6.78 mmol) of sodium hydride as a 60% mineral oil suspension. The ice bath was removed, and the reaction was stirred for 1 hour. To the reaction was then added 1.32 g (8.13 mmol) of 1,1'-carbonyldiimidazole. After stirring a further 2 hours, the reaction was concentrated in vacuo. The residue was partitioned between dichloromethane and a saturated solution of ammonium chloride. The aqueous layer was washed twice with dichloromethane. The dichloromethane layers were combined, dried over magnesium sulfate, and concentrated in vacuo. The residue was dissolved in dichloromethane, added silica gel, and concentrated in vacuo. The residue was chromatographed on silica gel, eluting with dichloromethane/ethyl acetate (9:0.5 v/v), to give 0.7507 g (70%) of the title compound: mp 189-191° C.

Analysis calculated for $C_{17}H_{19}N_4O_3ClS$: C. 51.71; H, 4.85; N, 14.19.

Found: C, 51.95; H, 4.81; N, 13.88.

EXAMPLE 64

3-(2-Chloro-3,5-dimethoxy-phenyl)-1-ethyl-7-methanesulfinyl-3,4-dihydro-pyrimido [4,5-d]pyrimidin-2(1H)-one Into a solution of 0.7457 g (1.89 mmol) of 3-(2-chloro-3,5-dimethoxy-phenyl)-1-ethyl-7-methylsulfanyl-3,4-dihydro-pyrimido[4,5-d]pyrimidin-2(1H)-one in 7 mL chloroform was added 0.5428 g (2.08 mmol) of trans-2-(phenylsulfonyl)-3-phenyloxaziridine. The reaction was stirred at room temperature overnight, then concentrated in vacuo. The residue was chromatographed down silica gel, eluting with ethyl acetate/ethanol (9:1 v/v), to give 0.697 g (90%) of the title compound.

Analysis calculated for $C_{17}H_{19}N_4O_4ClS.0.06\ CH_2Cl_2$: C, 49.26; H, 4.63; N, 13.47.

Found: C, 49.58; H, 4.69; N, 13.08.

EXAMPLE 65

3-(2-Chloro-3,5-dimethoxy-phenyl)-7-(4-diethylamino-butylamino)-1-ethyl-3,4-dihydro-pyrimido[4,5-d]pyrimidin-2(1H)-one A solution of 0.1074 g (0.2614 mmol) of 3-(2-chloro-3,5-dimethoxy-phenyl)-7-(4-diethylamino-butylamino)-1-ethyl-3,4-dihydro-pyrimido[4,5-d]pyrimidin-2(1H)-one, 0.113 g (0.784 mmol) of diethylaminobutylamine, and 0.067 g (0.287 mmol) of camphorsulfonic acid in 4 mL of dry dioxane was warmed at 60° C. After stirring overnight the reaction was concentrated in vacuo, and the residue was dissolved in dichloromethane. The dichloromethane solution was extracted three times with a saturated solution of sodium bicarbonate, dried over magnesium sulfate, and concentrated in vacuo. The residue was chromatographed down silica gel, eluting with ethyl acetate/ethanol/triethylamine (9:1:0.5 v/v/v), to give 0.106 g (82%) of the title compound.

MS (APCI) (m+1)/z 491.1

Examples 66-67 are depicted in Scheme 3.

EXAMPLE 66

3-(3,5-Dimethoxy-phenyl)-7-methylsulfanyl-3,4-dihydro-pyrimido [4,5-d]pyrimidin-2-ylamine Into a solution of 25.0 g (81.6 mmol) of 5-[(3,5-dimethoxy-phenylamino)-methyl]-2-methylsulfanyl-pyrimidin-4-ylamine in 125 mL of dry dimethylformamide cooled to 5° C., was added a solution of 10.1 g (95.5 mmol) of cyanogen bromide in 25 mL of dry dimethylformamide portionwise. After the addition of the cyanogen bromide solution the ice bath was removed, and the reaction was allowed to warm to room temperature over 30 minutes. The reaction was warmed to 80° C. for 4 hours, then added to 500 mL of 1N NaOH. The aqueous suspension was extracted with dichloromethane (7×150 mL). The dichloromethane layers were combined and concentrated in vacuo. The residue was dissolved in dichloromethane, extracted three times with a saturated solution of sodium chloride, dried over magnesium sulfate, and concentrated in vacuo. The residue was dissolved in tetrahydrofuran, added silica gel, and concentrated in vacuo. The residue was chromatographed down silica gel, eluting first with ethyl acetate, then switching to ethyl acetate/ethanol (9:1 v/v), giving product which was slightly impure. This product was rechromatographed down silica gel, eluting with first chloroform, then switching to chloroform/methanol (9:0.5 v/v), to give 7.34 g (24%) of the title compound: mp 198-204° C.

Analysis calculated for $C_{15}H_{17}N_5O_2S \cdot 0.30$ CHCl$_3$: C, 50.04; H, 4.75; N, 19.07; S, 8.73.
Found: C, 50.11; H, 4.59; N, 19.18; S, 8.91.

EXAMPLE 67

3-(3,5-Dimethoxy-phenyl)-7-methanesulfinyl-3,4-dihydro-pyrimido[4,5-d]pyrimidin-2-ylamine Into a solution of 2.00 g (6.04 mmol) of 3-(3,5-dimethoxy-phenyl)-7-methylsulfanyl-3,4-dihydro-pyrimido[4,5-d]pyrimidin-2-ylamine in 50 mL of chloroform was added a solution of 1.73 g (6.64 mmol) of trans-2-(phenylsulfonyl)-3-phenyloxaziridine in 20 mL of chloroform. The reaction was stirred overnight at room temperature, then concentrated in vacuo. The residue was dissolved in dichloromethane, added silica gel, and concentrated in vacuo. The residue was chromatographed down silica gel, eluting first with ethyl acetate then ethyl acetate/ethanol/triethylamine (9:2:1 v/v/v), to give 1.4306 g (68%) of the title product.
Analysis calculated for $C_{15}H_{17}N_5O_3S \cdot 0.25$ EtOAc·0.25H$_2$O: C, 51.37; H, 5.26; N, 18.73.
Found: C, 51.15; H, 5.23; N, 18.44.

Preparation 14

Ethyl 4-(isopropylamino)-2-(methylthio)pyrimidine-5-carboxylate

To a 0° C. solution of 10.0 g (43.0 mmol) of ethyl 4-chloro-2-(methylthio)pyrimidine-5-carboxylate and 7.2 mL (51.6 mmol) of triethylamine in 100 mL of dichloromethane is added 4.4 mL (51.6 mmol) of isopropylamine. The reaction solution is stirred at 0° C. for 2 hours then allowed to warm to room temperature. The reaction mixture is diluted with ethyl acetate, washed twice with aqueous HCl, twice with water, once with a saturated solution of sodium bicarbonate, and brine. The organic phase is dried over magnesium sulfate, filtered, and concentrated to give 11.1 g (quant.) of the title compound as an oil which solidified on standing: mp 159-160° C.
Mass Spectrum (CI) (m+1)/z 256.

Preparation 15

4-(Isopropylamino)-2-(methylthio)pyrimidine-5-carboxylic acid

To a solution of 5.0 g (19.6 mmol) of ethyl 4-(isopropylamino)-2-(methylthio)pyrimidine-5-carboxylate in 20 mL of ethanol is added a solution of 0.8 g (20.6 mmol) of sodium hydroxide in 30 mL of water. The reaction suspension is stirred at room temperature overnight. The reaction solution is diluted with 100 mL of water and washed twice with diethyl ether. The aqueous phase is neutralized with 20.6 mL of 1N HCl. The precipitate is filtered and washed twice with water, dried under vacuum at 70° C. to give 4.0 g (90%) of the title compound: mp 202-203° C. (dec).
Analysis calculated for $C_9H_{13}N_3SO_2$: C, 47.56; H, 5.77; N, 18.49.
Found: C, 47.38; H, 5.70; N, 18.29.

Preparation 16

N-Allyl-4-(isopropylamino)-2-(methylthio)pyrimidine-5-carboxamide

To 3.5 (15.4 mmol) of 4-(isopropylamino)-2-(methylthio) pyrimidine-5-carboxylic acid is added 9.0 mL (123.2 mmol) of thionyl chloride, and the reaction mixture is heated at 50° C. for 1 hour, cooled to room temperature, and concentrated. The residue is twice suspended in anhydrous toluene and concentrated to give a colorless solid, 4-(isopropylamino)-2-(methylthio) pyrimidine-5-carboxylic acid chloride.
To a 0° C. suspension of 4-(isopropylamino)-2-(methylthio)pyrimidine-5-carboxylic acid chloride in 10 mL of tetrahydrofuran is added 3.5 mL (46.2 mmol) of allylamine and 20 mL of tetrahydrofuran. The reaction suspension is allowed to warm briefly to room temperature, then stored at 0° C. overnight. The reaction mixture is diluted with ethyl acetate, washed with 1N HCl, a saturated solution of sodium bicarbonate, and brine. The organic phase is dried over magnesium sulfate, filtered, and concentrated to give 2.1 g (51%) of the title compound:
mp 159-161° C.
Analysis calculated for $C_{12}H_{18}N_4SO$: C, 54.11; H, 6.81; N, 21.03.
Found: C, 54.42; H, 6.69; N, 21.13.

Preparation 17

N-(4-Methoxybenzyl)-4-(isopropylamino)-2-(methylthio)pyrimidine-5-carboxamide

To a 0° C. suspension of 4-(isopropylamino)-2-(methylthio)pyrimidine-5-carboxylic acid chloride (as prepared in the above example, Preparation 16) in 30 mL of tetrahydrofuran is added 6.0 mL (46.3 mmol) of 4-methoxybenzylamine and 30 mL of tetrahydrofuran. The reaction suspension is allowed to warm briefly to room temperature, then stored at 0° C. overnight. The reaction mixture is diluted with dichloromethane, washed with 1N HCl and water. The combined aqueous phase is washed with dichloromethane. The combined organic phase is washed with a saturated solution of sodium bicarbonate and brine, dried over magnesium sulfate, filtered, and concentrated. The residue is crystallized from ethyl acetate/hexane to give 3.27 g (61%) of the title compound: mp 176-177° C.
Analysis calculated for $C_{17}H_{22}N_4SO_2$: C, 58.94; H, 6.40; N, 16.17.
Found: C, 58.87; H, 6.34; N, 16.26.

EXAMPLE 68

3-Allyl-7-(imidazol-1-yl)-1-isopropyl-1H-pyrimido[4,5-d]pyrimidine-2,4-dione

To a 0° C. suspension of 563 mg (14.1 mmol) of sodium hydride (60% disp.) is added 1.5 g (5.63 mmol) of N-allyl-4-(isopropylamino)-2-(methylthio)pyrimidine-5-carboxamide, and the reaction mixture is stirred for 15 minutes. To the reaction mixture is added in small portions 2.7 g (16.9 mmol) of 1,1'-carbonyldiimidazole. The reaction mixture is stirred overnight at room temperature, diluted with ethyl acetate, and washed with a saturated solution of sodium bicarbonate, water, and brine. The combined aqueous phase is washed with ethyl acetate. The combined organic phase is dried over magnesium sulfate, filtered, and concentrated. The residue is chromatographed on silica eluting with 4:6 ethyl acetate/hexane. The single component fractions are collected and crystallized from dichloromethane/hexane to give 457 mg (26%) of the title compound: mp 158-160° C.
Analysis calculated for $C_{15}H_{16}N_6O_2$: C, 57.68; H, 5.16; N, 26.91.
Found: C, 57.57; H, 4.90; N, 26.98.
The mixed component fractions are also collected and crystallized as above to give 782 mg (44%) of analytically pure title compound.

EXAMPLE 69

7-(Imidazol-1-yl)-1-isopropyl-3-(4-methoxybenzyl)-1H-pyrimido[4,5-d]pyrimidine-2,4-dione To a 0° C. suspension of 865 mg (21.6 mmol) of sodium hydride (60% disp.) is added 3.0 g (8.66 mmol) of N-(4-methoxybenzyl)-4-(isopropylamino)-2-(methylthio)pyrimidine-5-carboxamide, and the reaction mixture is stirred for 1 hour. To the reaction mixture is added in small portions 4.2 g (26.0 mmol) of 1,1'-carbonyldiimidazole. The reaction mixture is warmed at 50° C. for 5 hours, concentrated to dryness, and dissolved in 300 mL of 6N HCl. The solution is washed with diethyl ether, made basic with 50% aqueous solution of sodium hydroxide while maintaining the solution temperature below 40° C. The suspension is cooled to 15° C., and the precipitate is filtered, washed with water, and dried under vacuum at 65° C. to give 3.1 g (91%) of the title compound: mp 148-150° C. (dec).

Analysis calculated for $C_{20}H_{20}N_6O_3$: C, 61.22; H, 5.14; N, 21.42.

Found: C, 60.92; H, 5.25; N, 21.17.

EXAMPLE 70

3-Allyl-1-isopropyl-7-[4-(4-methylpiperazin-1-yl)phenylamino]-1H-pyrimido[4,5-d]pyrimidine-2,4-dione A mixture of 300 mg (0.96 mmol) of 3-allyl-7-(imidazol-1-yl)-1-isopropyl-1H-pyrimido[4,5-d]pyrimidine-2,4-dione and 551 mg (2.88 mmol) of 1-(4-aminophenyl)-4-methylpiperazine is heated at 180° C. for 2 hours. The reaction mixture is cooled, dissolved into chloroform, and chromatographed on silica eluting with 4:96 methanol/chloroform. The resulting material is crystallized from methanol/water to give 251 mg (60%) of the title compound: mp 176-177° C.

Analysis calculated for $C_{23}H_{29}N_7O_2 \cdot H_2O$: C, 60.91; H, 6.89; N, 21.62.

Found: C, 60.79; H, 6.80; N, 21.54.

EXAMPLE 71

1-Isopropyl-3-(4-methoxybenzyl)-7-[4-(4-methylpiperazin-1-yl)phenylamino]-1H-pyrimido[4,5-d]pyrimidine-2,4-dione A mixture of 700 mg (1.78 mmol) of 7-(imidazol-1-yl)-1-isopropyl-3-(4-methoxybenzyl)-1H-pyrimido[4,5-d]pyrimidine-2,4-dione and 1.02 g (5.35 mmol) of 1-(4-aminophenyl)-4-methylpiperazine is heated at 180° C. for 2 hours. The reaction mixture is cooled, dissolved into chloroform, and chromatographed on silica eluting with 5:95 methanol/chloroform. The resulting material is crystallized from methanol/water to give 530 mg (58%) of the title compound: mp 215-216° C.

Analysis calculated for $C_{28}H_{33}N_7O_3$: C, 65.22; H, 6.45; N, 19.02.

Found: C, 65.28; H, 6.41; N, 19.00.

EXAMPLE 72

3-Allyl-7-[4-(2-Diethylaminoethoxy)phenylamino]-1-isopropyl-1H-pyrimido[4,5-d]pyrimidine-2,4-dione A mixture of 200 mg (0.64 mmol) of 3-allyl-7-(imidazol-1-yl)-1-isopropyl-1H-pyrimido[4,5-d]pyrimidine-2,4-dione and 400 mg (1.92 mmol) of 4-(2-diethylaminoethoxy)aniline is heated at 180° C. for 3 hours. The reaction mixture is cooled, dissolved into chloroform, and chromatographed on silica eluting with 4:96 methanol/chloroform. The resulting oily material partially crystallizes on standing, and the mixture is triturated with diethyl ether/hexane and filtered to give 106 mg (36%) of the title compound: mp 90-96° C.

Analysis calculated for $C_{24}H_{32}N_6O_3$: C, 63.70; H, 7.13; N, 18.57.

Found: C, 63.39; H, 7.15; N, 18.36.

EXAMPLE 73

7-[4-(2-Diethylaminoethoxy)phenylamino]-1-isopropyl-3-(4-methoxybenzyl)-1H-pyrimido[4,5-d]pyrimidine-2,4-dione A mixture of 700 mg (1.78 mmol) of 7-(imidazol-1-yl)-1-isopropyl-3-(4-methoxybenzyl)-1H-pyrimido[4,5-d]pyrimidine-2,4-dione and 1.1 g (5.35 mmol) of 4-(2-diethylaminoethoxy)aniline is heated at 180° C. for 4 hours, then cooled. To the reaction mixture is added 357 mg (3.6 mmol) of succinic anhydride, 1 mL of chloroform, and 3 mL of dimethylformamide. The reaction mixture is heated at 50° C. for 2 hours, cooled, and diluted with chloroform. The mixture is washed with a saturated solution of sodium bicarbonate and brine. The organic phase is dried over magnesium sulfate, filtered, and concentrated. The residue is chromatographed on silica eluting with 5:95 methanol/chloroform to give a yellow solid which is crystallized from methanol/water to give 590 mg (61%) of the title compound: mp 139-141° C.

Analysis calculated for $C_{29}H_{36}N_6O_4$: C, 65.39; H, 6.81; N, 15.78.

Found: C, 65.35; H, 6.83; N, 15.70.

As noted above, the compounds of this invention are potent inhibitors of cyclin-dependent kinases and tyrosine kinases, and accordingly, are useful in treating and preventing atherosclerosis, and other cell proliferative disorders like cancer. The compounds have low toxicity. The compounds have exhibited excellent inhibitory activity against a wide variety of cyclin-dependent kinases, all in assay systems routinely utilized to measure such activity. A typical assay, for instance, measures inhibitory activity against the cyclin D dependent kinase 4 enzyme (cdk4/D). The invention compounds of Formula I exhibited $IC_{50}$ values ranging generally from about 0.04 μM to >40 μM. The cdk4 assay was carried out as follows.

Cyclin-Dependent Kinase 4 (cdk4) Assay

Enzyme assays for $IC_{50}$ determinations (Tables 1 and 2) and kinetic evaluation were performed in 96 well filter plates (Millipore MADVN6550). The total volume was 0.1 mL containing a final concentration of 20 mM TRIS (tris[hydroxymethyl]aminomethane), at pH 7.4, 50 mM NaCl, 1 mM dithiothreitol, 10 mM MgCl$_2$, 25 μM ATP containing 0.25 μCi of [$^{32}$P]ATP, 20 ng of cdk4, 1 μg of retinoblastoma, and appropriate dilutions of a compound of the present invention. All components except the ATP were added to the wells, and the plate was placed on a plate mixer for 2 minutes. The reaction was started by adding [$^{32}$P]ATP and the plate was incubated at 25° C. for 15 minutes. The reaction was terminated by addition of 0.1 mL of 20% trichloroacetic acid (TCA). The plate was kept at 4° C. for at least 1 hour to allow the substrate to precipitate. The wells were then washed five times with 0.2 mL of 10% TCA and $^{32}$p incorporation was determined with a beta plate counter (Wallac Inc., Gaithersburg. MD).

Cyclin-Dependent Kinase Assays (cdk2/cyclinE, cdk2/cyclinA, cdc2/cyclinB)

Enzyme assays for $IC_{50}$ determinations and kinetic evaluation were performed in a 96-well filter plate (Millipore MADVN6550) in a total volume of 0.1 mL of 20 mM TRIS (tris[hydroxymethyl]aminomethane), at pH 7.4, 50 mM NaCl, 1 mM dithiothreitol, 10 mM $MgCl_2$, 12 mM ATP containing 0.25 µCi of [$^{32}$P]ATP, 20 ng of enzyme (either cdk2/cyclinE, cdk2/A, or cdc2/cyclinB), 1 µg retinoblastoma, and appropriate dilutions of the particular invention compound. All components except the ATP were added to the wells, and the plate was placed on a plate mixer for 2 minutes. The reaction was begun by addition of [$^{32}$P]ATP, and the plate was incubated at 25° C. for 15 minutes. The reaction was terminated by addition of 0.1 mL of 20% TCA. The plate was kept at 4° C. for at least 1 hour to allow the substrate to precipitate. The wells were then washed five times with 0.2 mL of 10% TCA and $^{32}$P incorporation determined with a beta plate counter (Wallac Inc., Gaithersburg, Md.).

When measured against cdk2/E, the invention compounds exhibited $IC_{50}$ values ranging generally from about 0.9 µM to >40 µM. Against cdk2/A, the compounds exhibited $IC_{50}$ values ranging from about 0.5 µM to >40 µM, and against cdc2/B, generally from about 5 µM to >40 µM. The assays were carried out as described above, and specific data for the invention compounds is given in the following tables.

TABLE 1

| | | | $IC_{50}$ (µM) or % Inhibition at 40 µM | | | |
|---|---|---|---|---|---|---|
| Example | $R^1$ | $R^2$ | cdk4/D | cdk2/E | cdk2/A | cdk1/B |
| 9 | Ph-4-OMe | cyclopentyl | 5.75 | | | |
| 10 | Ph-4-piperidine | cyclopentyl | 1.55 | | | |
| 11 | Ph-4-(4-Me)piperazine | cyclopentyl | 0.039 | 2.12 | 0.76 | 11.6 |
| 12 | Ph-4-pyrazole | cyclopentyl | 1.80 | 4.60 | 1.33 | 12.20 |
| 13 | Ph-3-Me-4-OCH$_2$CH$_2$NEt$_2$ | cyclopentyl | 0.3 | | | |
| 14 | Ph-4-pyrrole | cyclopentyl | 17.8 | 38% | 5.1 | >20 |
| 15 | Ph-4-(4-OH)-piperidine | cyclopentyl | 0.70 | 2.2 | 0.6 | 16.76 |
| 16 | Ph-4-(3-OH)-piperidine | cyclopentyl | 0.63 | 1.5 | 0.64 | 14.93 |
| 17 | Ph-4-(4-NMe$_2$)-piperidine | cyclopentyl | 0.31 | 3.55 | 1.31 | 20.20 |
| 18 | Ph-4-(3,5-Me$_2$)-piperazine | cyclopentyl | 0.35 | 2.0 | | |
| 19 | Ph-4-(2-CH$_2$OH)-piperidine | cyclopentyl | 0.5 | | | |
| 20 | Ph-4-[4-(CH$_2$)$_3$OH]-piperidine | cyclopentyl | 0.42 | 5.35 | 2.72 | >40 |
| 21 | Ph-4-[4-(CH$_2$)$_2$morpholine]-piperidine | cyclopentyl | 0.165 | 3.00 | 1.37 | 36.14 |
| 22 | Ph-4-(4-Me)piperazine | isopropyl | 0.34 | 68% | 9.31 | 25% |
| 23 | Ph-4-(4-OH)-piperidine | isopropyl | | 16.85 | 4.39 | >40 |
| 24 | Ph-4-(4-NMe$_2$)-piperidine | isopropyl | | 34.00 | 12.35 | >40 |
| 25 | Ph-4-pyrazole | isopropyl | | 10.00 | 2.31 | 36.50 |
| 26 | Ph-4-[4-(CH$_2$)$_3$morpholine]-piperidine | isopropyl | 47% | 27.00 | 6.46 | >40 |
| 27 | Ph-4-(4-Me)piperazine | norbornyl | 0.77 | 1.10 | 0.53 | 9.77 |
| 28 | Ph-4-(4-Me)piperazine | methyl | 15% | 22% | >40 | >40 |
| 29 | Ph-4-(4-OH)-piperidine | methyl | >40 | 28% | >40 | >40 |
| 30 | Ph-4-(4-NMe$_2$)-piperidine | methyl | 18.25 | | >40 | >40 |
| 31 | Ph-4-pyrazole | methyl | 18% | 21% | >40 | >40 |

TABLE 1a

| | | | $IC_{50}$ (µM) or % Inhibition at 40 µM | | | |
|---|---|---|---|---|---|---|
| Example | $R^1$ | $R^2$ | cdk4/D | cdk2/E | cdk2/A | cdk1/B |
| 70 | Ph-4-(4-Me)piperazine | allyl | 3.45 | 0% | >40 | >40 |
| 72 | Ph-4-O(CH$_2$)$_2$NEt$_2$ | allyl | 7.35 | 0% | >40 | >40 |
| 71 | Ph-4-(4-Me)piperazine | 4-OMe-benzyl | 2.1 | | >40 | >40 |
| 73 | Ph-4-O(CH$_2$)$_2$NEt$_2$ | 4-OMe-benzyl | 4.5 | | >40 | >40 |

Table 2 presents data for specific pyrimido[4,5-d]pyrimidines (double bond at the 3,4-position).

TABLE 2

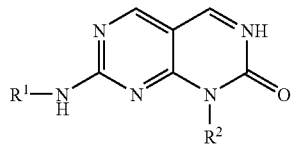

| | | | IC$_{50}$ (μM) or % Inhibition at 40 μM | | | |
|---|---|---|---|---|---|---|
| Example | R$^1$ | R$^2$ | cdk4/D | cdk2/E | cdk2/A | cdk1/B |
| 32 | Ph-4-(4-Me)piperazine | cyclopentyl | 0.05 | 1.38 | 0.83 | 7.51 |
| 33 | Ph-4-(4-OH)-piperidine | cyclopentyl | 0.038 | 4.2 | 0.98 | 9.76 |
| 34 | Ph-3-Me-4-OCH$_2$CH$_2$NEt$_2$ | cyclopentyl | 0.079 | 3.15 | 3.22 | 7.51 |
| 35 | Ph-4-(3-OH)piperidine | cyclopentyl | 0.082 | 1.05 | 0.99 | 8.54 |
| 36 | Ph-4-pyrazole | cyclopentyl | 0.435 | 2.44 | 1.33 | 16.13 |
| 37 | Ph-4-OMe | cyclopentyl | 0.22 | 0.9 | 0.40 | 4.76 |
| 38 | Ph-4-piperidine | cyclopentyl | 0.15 | 2.78 | 0.77 | 35.25 |
| 39 | Ph-4-[4-(CH$_2$)$_2$morpholine]-piperidine | cyclopentyl | 0.3 | 1.85 | 1.44 | 24.61 |
| 40 | Ph-4-(4-Me)-piperazine | isopropyl | | 16.50 | 4.51 | 42% |
| 41 | Ph-4-(4-NMe$_2$)-piperidine | isopropyl | | >40 | 14.76 | >40 |
| 42 | Ph-4-pyrrazole | isopropyl | 3.9 | >40 | 5.81 | >40 |
| 43 | Ph-4-[4-(CH$_2$)$_3$morpholine]-piperidine | isopropyl | 0.54 | 38.0 | 7.49 | >40 |
| 44 | Ph-4-(4-Me)-piperazine | norbornyl | 0.018 | 1.2 | 1.03 | 7.36 |
| 45 | Ph-4-(4-Me)-piperazine | methyl | 16.2 | 16% | >40 | >40 |
| 46 | Ph-4-(4-NMe$_2$)-piperidine | methyl | >40 | | >40 | >40 |
| 47 | Ph-4-pyrazole | methyl | >40 | 41% | >40 | >40 |

Several of the invention compounds have also shown good inhibitory activity against cdk6/D$_2$ and cdk6/D$_3$ enzymes. These assays are carried out in a manner similar to that described above for cdk4, by simply employing the appropriate cdk6 kinase enzyme.

The compounds of Formula I also have shown good inhibitory activity against certain growth factor receptor tyrosine kinase enzymes, including those of fibroblast growth factor (FGF) and platelet derived growth factor (PDGF). The invention compounds range in IC$_{50}$ inhibition against FGF tyrosine kinase generally from about 0.3 μM to >50 μM. Against PDGF tyrosine kinase, the invention compounds exhibit IC$_{50}$ from about 0.02 μM to >50 μM. The assays used to determine these activities were carried out as follows:

PDGF and FGF Receptor Tyrosine Kinase Assays

Full-length cDNAs for the mouse PDGF-β and human FGF-1 (flg) receptor tyrosine kinases were obtained from J. Escobedo and prepared as described in *J. Biol. Chem.*, 1991; 262:1482-1487. PCR primers were designed to amplify a fragment of DNA that codes for the intracellular tyrosine kinase domain. The fragment was inserted into a baculovirus vector, cotransfected with AcMNPV DNA, and the recombinant virus isolated. SF9 insect cells were infected with the virus to overexpress the protein, and the cell lysate was used for the assay. Assays were performed in 96-well plates (100 μL/incubation/well), and conditions were optimized to measure the incorporation of $^{32}$P from γ$^{32}$P-ATP into a glutamate-tyrosine co-polymer substrate. Briefly, to each well was added 82.5 μL of incubation buffer containing 25 mM Hepes (pH 7.0), 150 mM NaCl, 0.1% Triton X-100, 0.2 mM PMSF, 0.2 mM Na$_3$VO$_4$, 10 mM MnCl$_2$, and 750 μg/mL of Poly (4:1) glutamate-tyrosine followed by 2.5 μL of inhibitor and 5 μL of enzyme lysate (7.5 μg/μL FGF-TK or 6.0 μg/μL PDGF-TK) to initiate the reaction. Following a 10 minute incubation at 25° C., 10 mL of γ$^{32}$P-ATP (0.4 μCi plus 50 μM ATP) was added to each well, and samples were incubated for an additional 10 minutes at 25° C. The reaction was terminated by the addition of 100 μL of 30% trichloroacetic acid (TCA) containing 20 mM sodium pyrophosphate and precipitation of material onto glass fiber mats (Wallac). Filters were washed three times with 15% TCA containing 100 mM sodium pyrophosphate, and the radioactivity retained on the filters counted in a Wallac 1250 Betaplate reader. Nonspecific activity was defined as radioactivity retained on the filters following incubation of samples with buffer alone (no enzyme). Specific enzymatic activity (enzyme plus buffer) was defined as total activity minus nonspecific activity. The concentration of a compound that inhibited specific activity by 50% (IC$_{50}$) was determined based on the inhibition curve, and typical results are reported in the following tables.

TABLE 3

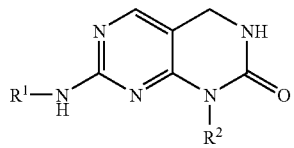

| | | | IC$_{50}$ (μM) or % Inhibition at 40 μM | |
|---|---|---|---|---|
| Example | R$^1$ | R$^2$ | PDGF | FGF |
| 9 | Ph-4-OMe | cyclopentyl | | 0.36 |
| 10 | Ph-4-piperidine | cyclopentyl | | 0.64 |
| 11 | Ph-4-(4-Me)piperazine | cyclopentyl | 0.175 | 0.023 |
| 13 | Ph-3-Me-4-OCH$_2$CH$_2$NEt$_2$ | cyclopentyl | | 0.5-0.05 |
| 15 | Ph-4-(4-OH)-piperidine | cyclopentyl | | 0.5-0.05 |
| 16 | Ph-4-(3-OH)-piperidine | cyclopentyl | 0.83 | |
| 17 | Ph-4-(4-NMe$_2$)-piperidine | cyclopentyl | 0.32 | |

TABLE 3-continued

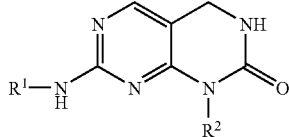

| | | | IC$_{50}$ (µM) or % Inhibition at 40 µM | |
|---|---|---|---|---|
| Example | R$^1$ | R$^2$ | PDGF | FGF |
| 18 | Ph-4-(3,5-diMe)-piperazine | cyclopentyl | 0.21 | |
| 19 | Ph-4-(2-CH$_2$OH)-piperidine | cyclopentyl | | 0.5-0.05 |
| 21 | Ph-4-[4-(CH$_2$)$_2$-morpholine]-piperidine | cyclopentyl | 1.1 | |
| 22 | Ph-4-(4-Me)-piperazine | isopropyl | | |
| 25 | Ph-4-pyrazole | isopropyl | | |
| 27 | Ph-4-(4-Me)-piperazine | norbornyl | | |
| 30 | Ph-4-(4-Me)-piperazine | methyl | | |

TABLE 3a

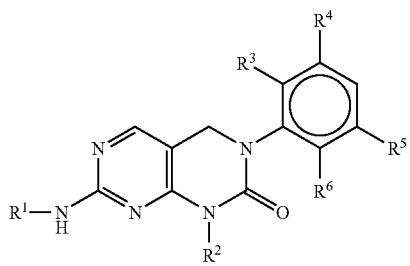

| | | | | | | | IC$_{50}$ (µM) | |
|---|---|---|---|---|---|---|---|---|
| Example | R$^1$ | R$^2$ | R$^3$ | R$^4$ | R$^5$ | R$^6$ | PDGF | FGF |
| 53 | (CH$_2$)$_4$NEt$_2$ | Et | H | OMe | OMe | H | 5 | 0.06 |
| 53a | Ph-4-O(CH$_2$)$_2$-NEt$_2$ | Et | H | OMe | OMe | H | <0.5 | 0.02 |

TABLE 3b

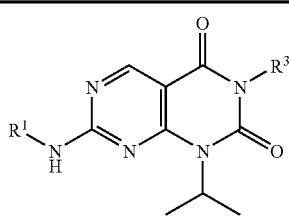

| | | | IC$_{50}$ (µM) or % Inhibition at 40 µM | |
|---|---|---|---|---|
| Example | R$^1$ | R$^3$ | PDGF | FGF |
| 71 | Ph-4-(4-Me)-piperazine | allyl | >50 | >50 |
| 73 | Ph-4-O(CH$_2$)$_2$NEt$_2$ | allyl | >50 | >50 |
| 72 | Ph-4-(4-Me)-piperazine | 4-OMe-benzyl | >50 | >50 |
| 74 | Ph-4-O(CH$_2$)$_2$NEt$_2$ | 4-OMe-benzyl | >50 | >50 |

TABLE 4

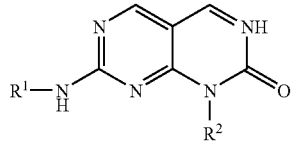

| | | | IC$_{50}$ (µM) or % Inhibition at 40 µM | |
|---|---|---|---|---|
| Example | R$^1$ | R$^2$ | PDGF | FGF |
| 32 | Ph-4-(4-Me)piperazine | cyclopentyl | 1.63 | 0.37 |
| 35 | Ph-4-(3-OH)-piperidine | cyclopentyl | 2.8 | 3.49 |
| 36 | Ph-4-pyrazole | cyclopentyl | >50 | >50 |
| 39 | Ph-4-[4-(CH$_2$)$_2$morpholine]piperidine | cyclopentyl | | 3.76 |
| 40 | Ph-4-(4-Me)piperazine | isopropyl | | 1.13 |
| 41 | Ph-4-(4-NMe$_2$)-piperidine | isopropyl | >50 | 11.73 |
| 43 | Ph-4-[4-(CH$_2$)$_2$morpholine]piperidine | isopropyl | | 4.93 |
| 44 | Ph-4-(4-Me)piperazine | norbornyl | | 0.47 |
| 46 | Ph-4-(4-NMe$_2$)-piperidine | methyl | | 22.6 |

The Src (the transforming gene of the Rous sarcoma retrovirus) family of non-receptor protein kinases, which all contain a SH2 domain, are involved in a number of cellular signaling pathways. For example, Src is involved in growth factor receptor signaling; integrin-mediated signaling; T- and B-cell activation and osteoclast activation. It is known that the Src SH2 domain binds to several key receptor and non-receptor tyrosine kinases such as tyrosine kinases containing receptors for PDGF, EGF, HER2/Neu (an oncogene form of EGF), FGF, focal adhesion kinase, p130 protein, and p68 protein. In addition, pp60c-Src has been shown to be involved in the regulation of DNA synthesis, mitosis, and other cellular activities.

Thus, it would be useful to have compounds that inhibit the binding of proteins containing an SH2 domain to cognate phosphorylated proteins, as the inhibition of binding of proteins containing an SH2 domain to cognate phosphorylated proteins can be used to treat proliferative diseases such as cancer, osteoporosis, inflammation, allergy, restenosis, and cardiovascular disease, which all rely on signal transduction involving proteins that contain an SH2 domain that binds to phosphorylated proteins during the cellular signaling process.

Several of the invention compounds have been evaluated in a standard assay to measure their ability to inhibit cellular Src protein kinase (c-Src). The invention compounds exhibited IC$_{50}$ values ranging generally from about 0.4 to about 50 µM. The assay was carried out as follows:

c-Src kinase was purified from baculovirus infected insect cell lysates using an antipeptide monoclonal antibody directed against the N-terminal amino acids (amino acids 2-17) of c-Src. The antibody, covalently linked to 0.65 µm latex beads, was added to a suspension of insect cell lysis buffer comprised of 150 mM NaCl, 50 mM Tris pH 7.5, 1 mM DTT, 1% NP-40, 2 mM EGTA, 1 mM sodium vanadate, 1 mM PMSF, 1 µg/mL each of leupeptin, pepstatin, and aprotinin. Insect cell lysate containing c-Src protein was incubated with these beads for 3 to 4 hours at 4° C. with rotation. At the end of the lysate incubation, the beads were rinsed three times in lysis buffer, resuspended in lysis buffer containing 10% glycerol, and frozen. These latex beads were thawed, rinsed three times in assay buffer (40 mM Tris, pH 7.5, 5 mM µgCl$_2$) and suspended in the same buffer. In a Millipore 96-well plate with a 0.65 µm polyvinylidine membrane bottom were added the reaction components: 10 µL c-Src beads, 10 µL of 2.5 mg/mL poly GluTyr substrate, 5 µM ATP containing 0.2 µCi labeled $^{32}$P-ATP, 5 µL DMSO containing inhibitors or as a solvent control, and buffer to make the final volume 125 µL. The reaction was started at room temperature by addition of the ATP and quenched 10 minutes later by the addition of 125 µL of 30% TCA, 0.1 M sodium pyrophosphate for 5 minutes on ice. The plate was then filtered and the wells washed with two 250 mL aliquots of 15% TCA, 0.1 M pyrophosphate. The filters were then punched, counted in a liquid scintillation counter, and the data examined for inhibitory activity in comparison to a known inhibitor such as erbstatin. The method is also described in *J. Med. Chem.*, 1994; 37:598-609. Tables 5 and 6 list c-Src inhibitory concentrations ($IC_{50}$) for representative invention compounds.

TABLE 5

| Example | $R^1$ | $R^2$ | c-Src $IC_{50}$ (µM) |
|---|---|---|---|
| 10 | Ph-4-piperidine | cyclopentyl | >50 |
| 11 | Ph-4-4-(Me)-piperazine | cyclopentyl | 0.71 |
| 14 | Ph-4-pyrrole | cyclopentyl | >50 |
| 15 | Ph-4-(4-OH)-piperidine | cyclopentyl | 2.4 |
| 16 | Ph-4-(3-OH)-piperidine | cyclopentyl | 4.12 |
| 17 | Ph-4-(4-NMe$_2$)-piperidine | cyclopentyl | 0.37 |
| 18 | Ph-4-(3,5-diMe)-piperazine | cyclopentyl | 0.40 |
| 19 | Ph-4-(2-CH$_2$OH)-piperidine | cyclopentyl | 4.42 |
| 21 | Ph-4[4-(CH$_2$)$_2$morpholine]-piperidine | cyclopentyl | 1.60 |
| 22 | Ph-4-(4-Me)-piperazine | isopropyl | 1.51 |

TABLE 6

| Example | $R^1$ | $R^2$ | c-Src $IC_{50}$ (µM) |
|---|---|---|---|
| 32 | Ph-4-(4-Me)piperazine | cyclopentyl | 3.95 |
| 35 | Ph-4-(3-OH)piperidine | cyclopentyl | 4.65 |
| 39 | Ph-4-[4-(CH$_2$)$_2$morpholine]-piperidine | cyclopentyl | 3.23 |
| 40 | Ph-4-(4-Me)piperazine | isopropyl | 4.30 |
| 41 | Ph-4-(4-NMe$_2$)piperidine | isopropyl | 3.06 |
| 44 | Ph-4-(4-Me)piperazine | norbornyl | 2.30 |

The compounds of Formula I are useful for treating cell proliferative disorders concerning angiogenesis and have been evaluated in a human umbilical vein endothelial cell in vitro assay. The assay described below is used to determine the anti-proliferative effects of the invention compounds on human umbilical vein endothelial cells, and the results are shown in Table 7.

Human Umbilical Vein Endothelial Cell (HUVEC) Proliferation Assay

Ninety-six well tissue culture plates are seeded with 100 µL of cells in all wells of rows A→G with row H remaining empty as a blank. HUVEC (Clonetics, San Diego, Calif.) are grown in endothelial growth medium (EGM media, Clonetics), containing 2% fetal bovine serum. The cell seed density for HUVEC cells is 20,000 per mL. C6 cells (ATCC Cat. No. CCL-107) are seeded at 6000 per mL in F10 medium (nutrient mixture Hemes) supplemented with 15% horse serum, 2.5% fetal bovine serum, and 6.0 mL 200 mM Glutamine per 600 mL medium. A90 cells (Suny, Buffalo, N.Y.) are also seeded at 6000 per mL, but they are grown in RPMI 1640 (Roswell Park Memorial Institute) plus 10% fetal bovine serum. Unless noted otherwise, tissue culture media and components are from GIBCO. The cells are allowed to incubate at 37° C., 5% $CO_2$, and 100% relative humidity for 16-24 hours.

Invention compounds are prepared by dissolving them in DMSO at a concentration of 5 mM, followed by dilution to 50 µM in EGM media. One hundred microliters of the compounds are applied to duplicate wells in column 1 of the previously prepared cell plates. Column 1 row H receives 100 µL of EGM media. The compounds in column 1 are diluted across the plates using serial two-fold dilutions.

The plates are incubated as above for an additional four days before being stained with Sulphorhodamine B. Staining is performed as follows: The media is removed from the plates, and the cells are fixed using 10% trichloroacetic acid for 30 minutes at 4° C. Following fixation, the plates are washed five times with distilled water after which 100 µL of Sulphorhodamine B is added to each well. Sulphorhodamine B is dissolved in 1% acetic acid to a concentration of 0.075%. Following staining, excess stain is removed from the wells, and the plates are washed four times with 1% acetic acid. The plates are allowed to air dry before the bound dye is solubilized in 100 µL of 10 mM unbuffered TRIS base. Absorbance is measured on a 96 well plate reader at 540 nM using a reference filter wavelength of 630 nM. The concentration of compound needed to suppress 50% of cell proliferation ($IC_{50}$) is determined from the absorbance measurements. Sulphorhodamine B and TRIS are from Sigma Chemical Company. Acetic acid and trichloroacetic acid are from Mallinckrodt AR.

TABLE 7

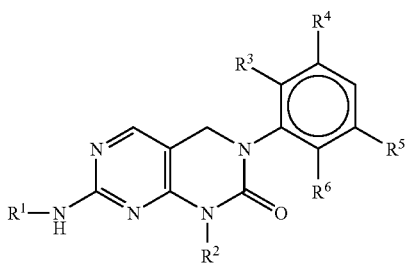

| Example | $R^1$ | $R^2$ | $R^3$ | $R^4$ | $R^5$ | $R^6$ | HUVEC $IC_{50}$ (µM) |
|---|---|---|---|---|---|---|---|
| 52 | (CH$_2$)$_4$NEt$_2$ | H | H | OMe | OMe | H | 6.65 |
| 53 | (CH$_2$)$_4$NEt$_2$ | Et | H | OMe | OMe | H | 0.192 |
| 53a | Ph-4-O(CH$_2$)$_2$NEt$_2$ | Et | H | OMe | OMe | H | |
| 54 | (CH$_2$)$_2$NHCH$_2$-(4-pyridyl) | H | H | OMe | OMe | H | >25 |
| 54a | (CH$_2$)$_3$-4-Me-piperazine | H | H | OMe | OMe | H | 5.99 |
| 54b | (CH$_2$)$_4$-4-Me-piperazine | H | H | OMe | OMe | H | 4.96 |
| 54c | (CH$_2$)$_5$-4-Me-piperazine | H | H | OMe | OMe | H | 5.78 |
| 55 | (CH$_2$)$_3$NEt$_2$ | H | H | OMe | OMe | H | >25 |
| 56 | (CH$_2$)$_2$-NHCH$_2$-(4-pyridyl) | Et | H | OMe | OMe | H | 1.93 |

TABLE 7-continued

[Structure: pyrimido[4,5-d]pyrimidin-2-one core with R$^1$—NH at 2-position, R$^2$ on N, and phenyl group bearing R$^3$, R$^4$, R$^5$, R$^6$ substituents]

| Example | R$^1$ | R$^2$ | R$^3$ | R$^4$ | R$^5$ | R$^6$ | HUVEC IC$_{50}$ (μM) |
|---|---|---|---|---|---|---|---|
| 57 | (CH$_2$)$_3$-4-Me-piperazine | Et | H | OMe | OMe | H | 0.152 |
| 58 | (CH$_2$)$_4$-4-Me-piperazine | Et | H | OMe | OMe | H | 0.134 |
| 59 | (CH$_2$)$_5$-4-Me-piperazine | Et | H | OMe | OMe | H | 0.112 |
| 60 | (CH$_2$)$_3$NEt$_2$ | Et | H | OMe | OMe | H | 0.943 |
| 65 | (CH$_2$)$_4$NEt$_2$ | Et | Cl | OMe | OMe | H | 0.036 |

The compounds of Formula I have also been evaluated in several standard in vivo cell culture assays and shown to have good inhibitory activity against tyrosine kinase enzymes.

The invention compounds can be formulated in conventional manners to provide convenient dosage forms for delivery to mammals by various routes, including oral, parenteral (i.e., subcutaneous, intravenous, and intramuscular), transdermal, e.g., slow release skin patch or cream, as well as by slow release delivery devices such as osmotic pumps, suppositories, and buccal seals. The following examples further illustrate how the compounds are readily formulated.

EXAMPLE 75

| | 50 mg Tablet Formulation | |
|---|---|---|
| Per Tablet | | Per 10,000 Tablets |
| 0.050 g | 1-Cyclopentyl-7-{3-methyl-4-[2-(diethylamino)-ethoxy]phenylamino}-3,4-dihydro-1H-pyrimido-[4,5-d]pyrimidin-2-one | 500 g |
| 0.080 g | lactose | 800 g |
| 0.010 g | corn starch (for mix) | 100 g |
| 0.008 g | corn starch (for paste) | 80 g |
| 0.148 g | | 1480 g |
| 0.002 g | magnesium stearate (1%) | 20 g |
| 0.150 g | | 1500 g |

The pyrimidopyrimidine, lactose, and corn starch (for mix) are blended to uniformity. The corn starch (for paste) is suspended in 600 mL of water and heated with stirring to form a paste. This paste is used to granulate the mixed powders. The wet granules are passed through a No. 8 hand screen and dried at 80° C. The dry granules are then passed through a No. 16 screen. The mixture is lubricated with 1% magnesium stearate and compressed into tablets in a conventional tableting machine. The tablets, as well as all invention compounds, are useful for treating cancers such as breast, prostate, lung, ovarian, colon, pancreatic, melanoma, esophageal, brain, Kaposi's sarcoma, and lymphomas. Particular concerns to be treated include small-cell lung carcinoma, low grade human bladder carcinoma, and human colorectal cancer.

EXAMPLE 76

| Preparation of Oral Suspension | |
|---|---|
| Ingredient | Amount |
| 1-Cyclopentyl-7-{4-[4-(dimethylamino)piperidin-1-yl]phenylamino}-3,4-dihydro-1H-pyrimido[4,5-d]pyrimidin-2-one | 500 mg |
| Sorbitol solution (70% N.F.) | 40 mL |
| Sodium benzoate | 150 mg |
| Saccharin | 10 mg |
| Cherry flavor | 50 mg |
| Distilled water qs | 100 mL |

The sorbitol solution is added to 40 mL of distilled water, and the pyrido pyrimidine is suspended therein. The saccharin, sodium benzoate, and flavoring are added and dissolved. The volume is adjusted to 100 mL with distilled water. Each milliliter of syrup contains 5 mg of invention compound.

EXAMPLE 77

Preparation of Parenteral Solution

In a solution of 700 mL of propylene glycol and 200 mL of water for injection is suspended 20.0 g of 1-cyclopentyl-7-[4-(4-methylpiperazin-1-yl)phenylamino]pyrimido[4,5-d]pyrimidin-2(1H)-one with stirring. After suspension is complete, the pH is adjusted to 5.5 with hydrochloric acid, and the volume is made up to 1000 mL with water for injection. The formulation is sterilized, filled into 5.0 mL ampoules, each containing 2.0 mL (representing 40 mg of invention compound) and sealed under nitrogen.

EXAMPLE 78

Suppositories

A mixture of 400 mg of 1-cyclopentyl-7-[4-(piperidin-1-yl)phenylamino]pyrimido[4,5-d]pyrimidin-2(1H)-one, and 600 mg of theobroma oil is stirred at 60° C. to uniformity. The mixture is cooled and allowed to harden in a tapered mold to provide a 1 g suppository.

EXAMPLE 79

Slow Release Formulation

Five hundred milligrams of 1-cyclopentyl-7-[4-(3-hydroxypiperidin-1-yl)phenylamino]-3,4-dihydro-1H-pyrimido[4,5-d]pyrimidin-2-one is converted to a hydrochloride salt and placed into an Oros osmotic pump for controlled release for treatment of atherosclerosis.

EXAMPLE 80

Skin Patch Formulation

Fifty milligrams of 1-cyclopentyl-7-{3-methyl-4-[2-(diethylamino)-ethoxy]phenylamino}-pyrimido[4,5-d]pyrimidin-2(1H)-one is admixed with 50 mg of propylene glycol monolaurate in a polydimethylsiloxane adhesive. The mixture is layered onto an elastic film made with an adhesive formulation of polybutene, polyisobutylene, and propylene glycol monolaurate. The layers are placed between 2 layers of polyurethane film. A release liner is attached to the adhesive surface, and is removed prior to application to a skin surface. The propylene glycol monolaurate serves as a permeation-enhancing agent.

What is claimed is:

1. A compound of formula I

I or a pharmaceutically acceptable salt thereof, wherein:

$R^1$ and $R^2$ are independently selected from the group consisting of H, $(CH_2)_n Ar$, $COR^4$, $(CH_2)_n$heteroaryl, $(CH_2)_n$heterocyclyl, $C_1$-$C_{10}$ alkyl, $C_3$-$C_{10}$ cycloalkyl, $C_2$-$C_{10}$ alkenyl, and $C_2$-$C_{10}$ alkynyl, wherein n is 0, 1, 2, or 3, and the $(CH_2)_n Ar$, $(CH_2)_n$heteroaryl, alkyl, cycloalkyl, alkenyl, and alkynyl groups are optionally substituted by up to 5 groups selected from $NR^4R^5$, $N^+(O)R^4R^5$, $N^+R^4R^5R^6Y^-$, alkyl, phenyl, substituted phenyl, $(CH_2)_n$heteroaryl, hydroxy, alkoxy, phenoxy, thiol, thioalkyl, halo, $COR^4CO_2R^4$, $CONR^4R^5$, $SO_2NR^4R^5$, $SO_3R^4$, $PO_3R^4$, aldehyde, nitrile, nitro, heteroaryloxy, $T(CH_2)_m QR^4$,

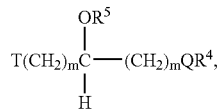

$C(O)T(CH_2)_m QR^4$, $NHC(O)T(CH_2)_m QR^4$, $T(CH_2)_m C(O)NR^4NR^5$, or $T(CH_2)_m CO_2R^4$ wherein each m is independently 1-6, T is O, S, $NR^4$, $N^+(O)R^4$, $N^+R^4R^6Y^-$, or $CR^4R^5$, and Q is O, S, $NR^5$, $N^+(O)R^5$, or $N^+R^5R^6Y^-$;

$R^4$ and $R^5$ are each independently selected from the group consisting of hydrogen, $C_1$-$C_6$ alkyl, substituted alkyl, $C_2$-$C_6$ alkenyl, $C_2$-$C_6$ alkynyl, $N(C_1$-$C_6$alkyl$)_{1\ or\ 2}$, $(CH_2)_n Ar$, $C_3$-$C_{10}$ cycloalkyl, heterocyclyl, and heteroaryl, or $R^4$ and $R^5$ together with the nitrogen to which they are attached optionally form a ring having 3 to 7 carbon atoms and said ring optionally contains 1, 2, or 3 heteroatoms selected from the group consisting of nitrogen, substituted nitrogen, oxygen, and sulfur;

when $R^4$ and $R^5$ together with the nitrogen to which they are attached form a ring, the said ring is optionally substituted by 1 to 3 groups selected from OH, $OR^4$, $NR^4R^5$, $(CH_2)_m OR^4$, $CH_2)_m NR^4R^5$, $T-(CH_2)_m QR^4$, $CO-T-CH_2)_m QR^4$, $NH(CO)T(CH_2)_m QR^4$, $T-(CH_2)_m CO_2R^4$, or $T(CH_2)_m CONR^4R^5$;

$R^6$ is alkyl; and

Y is a halo counter-ion.

2. The compound or pharmaceutically acceptable salt thereof of claim 1 wherein $R^1$ is phenyl or substituted phenyl, pyridyl or substituted pyridyl.

3. The compound or pharmaceutically acceptable salt thereof of claim 2 wherein $R^2$ is an alkyl, substituted alkyl, or cycloalkyl unsubstituted or substituted.

4. A compound selected from:
1-Methyl-7-[4-(pyrazol-1-yl)phenylamino]pyrimido[4,5-d]pyrimidin-2(1H)-one;
1-Methyl-7-[4-(4-methylpiperazin-1-yl)phenylamino]pyrimido[4,5-d]pyrimidin-2(1H)-one;
1-Methyl-7-[4-(4-hydroxypiperidin-1-yl)phenylamino] pyrimido[4,5-d]pyrimidin-2(1H)-one;
1-Methyl-7-{4-[4-(dimethylamino)piperidin-1-yl] phenylamino}pyrimido[4,5-d]pyrimidin-2(1H)-one;
1-Isopropyl-7-[4-(pyrazol-1-yl)phenylamino]pyrimido[4,5-d]pyrimidin-2(1H)-one;
1-Isopropyl-7-[4-(4-methylpiperazin-1-yl)phenylamino] pyrimido[4,5-d]pyrimidin-2(1H)-one;
1-Isopropyl-7-[4-(4-hydroxypiperidin-1-yl)phenylamino] pyrimido[4,5-d]pyrimidin-2(1H)-one;
1-Isopropyl-7-{4-[4-(dimethylamino)piperidin-1-yl] phenylamino}pyrimido[4,5-d]pyrimidin-2(1H)-one;
1-Bicyclo[2.2.1]hept-2-yl-7-[4-(pyrazol-1-yl)phenylamino]pyrimido[4,5-d]pyrimidin-2(1H)-one (exo);
1-Bicyclo[2.2.1]hept-2-yl-7-[4-(4-methylpiperazin-1-yl) phenylamino]pyrimido[4,5-d]pyrimidin-2(1H)-one (exo);
1-Bicyclo[2.2.1]hept-2-yl-7-[4-(4-hydroxypiperidin-1-yl) phenylamino]pyrimido[4,5-d]pyrimidin-2(1H)-one (exo);
1-Bicyclo[2.2.1]hept-2-yl-7-{4-[4-(dimethylamino)piperidin-1-yl]phenylamino}pyrimido[4,5-d]pyrimidin-2(1H)-one (exo);
7-[4-(4-Aminoacetyl-piperazin-1-yl)-phenylamino]-1-cyclopentyl-pyrimido[4,5-d]pyrimidin-2(1H)-one;
7-{4-[4-(2-Amino-4-methyl-pentanoyl)-piperazin-1-yl]-phenylamino}-1-cyclopentyl-pyrimido[4,5-d]pyrimidin-2(1H)-one;
1-Methyl-7-{4-[4-(3-morpholin-4-ylpropyl)piperidin-1-yl]phenylamino}pyrimido[4,5-d]pyrimidin-2(1H)-one;
1-Isopropyl-7-{4-[4-(3-morpholin-4-ylpropyl)piperidin-1-yl]phenylamino}pyrimido[4,5-d]pyrimidin-2(1H)-one;
1-Cyclopentyl-7-{4-[4-(3-morpholin-4-ylpropyl)piperidin-1-yl]phenylamino}pyrimido[4,5-d]pyrimidin-2(1H)-one;
1-Bicyclo[2.2.1]hept-2-yl-7-{4-[4-(3-morpholin-4-ylpropyl)piperidin-1-yl]phenylamino}pyrimido[4,5-d]pyrimidin-2(1H)-one (exo);
1-Cyclopentyl-7-(4-methanesulfonyl-phenylamino)-pyrimido[4,5-]pyrimidin-2(H)-one;
1-Cyclopentyl-7-(4-fluoro-3-methyl-phenylamino)-pyrimido[4,5-d]pyrimidin-2(1H)-one;
7-[4-(3-Amino-pyrrolidin-1-yl)-phenylamino]-1-cyclopentyl-pyrimido[4,5-d]pyrimidin-2(1H)-one;
1-Cyclopentyl-7-(4-piperazin-1-yl-phenylamino)-pyrimido[4,5-d]pyrimidin-2(1H)-one;
1-Cyclopentyl-7-[4-(5-methyl-hexahydro-pyrrolo[3,4-c]pyrrol-2-yl)-phenylamino]-pyrimido[4,5-d]pyrimidin-2(1H)-one;
7-[4-(4-Acetyl-piperazin-1-yl)-phenylamino]-1-cycloheptyl-pyrimido[4,5-d]pyrimidin-2(1H)-one; and
1-Cyclopentyl-7-(pyridin-4-ylamino)pyrimido[4,5-d]pyrimidin-2(1H)-one.

5. A compound selected from:
1-Methyl-7-[4-(pyrazol-1-yl)phenylamino]-3,4-dihydro-pyrimido[4,5-d]pyrimidin-2(1H)-one;
1-Methyl-7-[4-(4-methylpiperazin-1-yl)phenylamino]-3,4-dihydro-pyrimido[4,5-d]pyrimidin-2(1H)-one;

1-Methyl-7-[4-(4-hydroxypiperidin-1-yl)phenylamino]-3,4-dihydro-pyrimido[4,5-d]pyrimidin-2(1H)-one;

1-Methyl-7-{4-[4-(dimethylamino)piperidin-1-yl]phenylamino}-3,4-dihydro-pyrimido[4,5-d]pyrimidin-2(1H)-one;

1-Isopropyl-7-[4-(pyrazol-1-yl)phenylamino]-3,4-dihydro-pyrimido[4,5-d]pyrimidin-2(1H)-one;

1-Isopropyl-7-[4-(4-methylpiperazin-1-yl)phenylamino]-3,4-dihydro-pyrimido[4,5-d]pyrimidin-2(1H)-one;

1-Isopropyl-7-[4-(4-hydroxypiperidin-1-yl)phenylamino]-3,4-dihydro-pyrimido[4,5-d]pyrimidin-2(1H)-one;

1-Isopropyl-7-{4-[4-(dimethylamino)piperidin-1-yl]phenylamino}-3,4-dihydro-pyrimido[4,5-d]pyrimidin-2(1H)-one;

1-Bicyclo[2.2.1]hept-2-yl-7-[4-(pyrazol-1-yl)phenylamino]-3,4-dihydro-pyrimido[4,5-d]pyrimidin-2(1H)-one (exo);

1-Bicyclo[2.2.1]hept-2-yl-7-[4-(4-methylpiperazin-1-yl)phenylamino]-3,4-dihydro-pyrimido[4,5-d]pyrimidin-2(1H)-one (exo);

1-Bicyclo[2.2.1]hept-2-yl-7-[4-(4-hydroxypiperidin-1-yl)phenylamino]-3,4-dihydro-pyrimido[4,5-d]pyrimidin-2(1H)-one (exo);

1-Bicyclo[2.2.1]hept-2-yl-7-{4-[4-(dimethylamino)piperidin-1-yl]phenylamino}-3,4-dihydro-pyrimido[4,5-d]pyrimidin-2(1H)-one (exo);

7-[4-(4-Aminoacetyl-piperazin-1-yl)-phenylamino]-1-cyclopentyl-3,4-dihydro-pyrimido[4,5-d]pyrimidin-2(1H)-one;

7-{4-[4-(2-Amino-4-methyl-pentanoyl)-piperazin-1-yl]-phenylamino}-1-cyclopentyl-3,4-dihydro-pyrimido[4,5-d]pyrimidin-2(1H)-one;

1-Methyl-7-{4-[4-(3-morpholin-4-ylpropyl)piperidin-1-yl]phenylamino}-3,4-dihydro-pyrimido[4,5-d]pyrimidin-2(1H)-one;

1-Isopropyl-7-{4-[4-(3-morpholin-4-ylpropyl)piperidin-1-yl]phenylamino}-3,4-dihydro-pyrimido[4,5-d]pyrimidin-2(1H)-one;

1-Cyclopentyl-7-{4-[4-(3-morpholin-4-ylpropyl)piperidin-1-yl]phenylamino}-3,4-dihydro-pyrimido[4,5-d]pyrimidin-2(1H)-one;

1-Bicyclo[2.2.1]hept-2-yl-7-{4-[4-(3-morpholin-4-ylpropyl)piperidin-1-yl]phenylamino}-3,4-dihydro-pyrimido[4,5-d]pyrimidin-2(1H)-one (exo);

1-Cyclopentyl-7-(pyridin-4-ylamino)-3,4-dihydro-pyrimido[4,5-d]pyrimidin-2(1H)-one;

1-Cyclopentyl-7-(4-methanesulfonyl-phenylamino)-3,4-dihydro-pyrimido[4,5-d]pyrimidin-2(1H)-one;

1-Cyclopentyl-7-(4-fluoro-3-methyl-phenylamino)-3,4-dihydro-pyrimido[4,5-d]pyrimidin-2(1H)-one;

7-[4-(3-Amino-pyrrolidin-1-yl)-phenylamino]-1-cyclopentyl-3,4-dihydro-pyrimido[4,5-d]pyrimidin-2(1H)-one;

7-[4-(4-Acetyl-piperazin-1-yl)-phenylamino]-1-cyclopentyl-3,4-dihydro-pyrimido[4,5-d]pyrimidin-2(1H)-one;

1-Cyclopentyl-7-(4-piperazin-1-yl-phenylamino)-3,4-dihydro-pyrimido[4,5-d]pyrimidin-2(1H)-one;

1-Cyclopentyl-7-[4-(5-methyl-hexahydro-pyrrolo[3,4-c]pyrrol-2-yl)-phenylamino]-3,4-dihydro-pyrimido[4,5-d]pyrimidin-2(1H)-one;

7-[4-(4-Aminoacetyl-piperazin-1-yl)-phenylamino]-3-(3,5-dimethoxy-phenyl)-1-ethyl-3,4-dihydro-pyrimido[4,5-d]pyrimidin-2(1H)-one;

7-[4-(4-Aminoacetyl-piperazin-1-yl)-phenylamino]-3-(2-chloro-3,5-dimethoxy-phenyl)-1-ethyl-3,4-dihydro-pyrimido[4,5-d]pyrimidin-2(1H)-one;

7-[4-(4-Aminoacetyl-piperazin-1-yl)-phenylamino]-3-(2,6-dichloro-3,5-dimethoxy-phenyl)-1-ethyl-3,4-dihydro-pyrimido[4,5-d]pyrimidin-2(1H)-one;

7-[4-(4-Aminoacetyl-piperazin-1-yl)-phenylamino]-3-(2-methyl-3,5-dimethoxy-phenyl)-1-ethyl-3,4-dihydro-pyrimido[4,5-d]pyrimidin-2(1H)-one;

7-[4-(4-Aminoacetyl-piperazin-1-yl)-phenylamino]-3-(2,6-dimethyl-3,5-dimethoxy-phenyl)-1-ethyl-3,4-dihydro-pyrimido[4,5-d]pyrimidin-2(1H)-one;

7-[4-(2-Diethylamino-ethoxy)-phenylamino]-3-(3,5-dimethoxy-phenyl)-1-ethyl-3,4-dihydro-pyrimido[4,5-d]pyrimidin-2(1H)-one;

7-[4-(2-Diethylamino-ethoxy)-phenylamino]-3-(2-chloro-3,5-dimethoxy-phenyl)-1-ethyl-3,4-dihydro-pyrimido[4,5-d]pyrimidin-2(1H)-one;

7-[4-(2-Diethylamino-ethoxy)-phenylamino]-3-(2,6-dichloro-3,5-dimethoxy-phenyl)-1-ethyl-3,4-dihydro-pyrimido[4,5-d]pyrimidin-2(1H)-one;

7-[4-(2-Diethylamino-ethoxy)-phenylamino]-3-(2-methyl-3,5-dimethoxy-phenyl)-1-ethyl-3,4-dihydro-pyrimido[4,5-d]pyrimidin-2(1H)-one;

7-[4-(2-Diethylamino-ethoxy)-phenylamino]-3-(2,6-dimethyl-3,5-dimethoxy-phenyl)-1-ethyl-3,4-dihydro-pyrimido[4,5-d]pyrimidin-2(1H)-one;

7-(4-Diethylamino-butylamino)-3-(3,5-dimethoxy-phenyl)-1-ethyl-3,4-dihydro-pyrimido[4,5-d]pyrimidin-2(1H)-one;

7-(4-Diethylamino-butylamino)-3-(2-chloro-3,5-dimethoxy-phenyl)-1-ethyl-3,4-dihydro-pyrimido[4,5-d]pyrimidin-2(1H)-one;

7-(4-Diethylamino-butylamino)-3-(2,6-dichloro-3,5-dimethoxy-phenyl)-1-ethyl-3,4-dihydro-pyrimido[4,5-d]pyrimidin-2(1H)-one;

7-(4-Diethylamino-butylamino)-3-(2-methyl-3,5-dimethoxy-phenyl)-1-ethyl-3,4-dihydro-pyrimido[4,5-d]pyrimidin-2(1H)-one;

7-(4-Diethylamino-butylamino)-3-(2,6-dimethyl-3,5-dimethoxy-phenyl)-1-ethyl-3,4-dihydro-pyrimido[4,5-d]pyrimidin-2(1H)-one;

7-(Pyridin-4-ylamino)-3-(3,5-dimethoxy-phenyl)-1-ethyl-3,4-dihydro-pyrimido[4,5-d]pyrimidin-2(1H)-one;

7-(Pyridin-4-ylamino)-3-(2-chloro-3,5-dimethoxy-phenyl)-1-ethyl-3,4-dihydro-pyrimido[4,5-d]pyrimidin-2(1H)-one;

7-(Pyridin-4-ylamino)-3-(2,6-dichloro-3,5-dimethoxy-phenyl)-1-ethyl-3,4-dihydro-pyrimido[4,5-d]pyrimidin-2(1H)-one;

7-(Pyridin-4-ylamino)-3-(2,6-dimethyl-3,5-dimethoxy-phenyl)-1-ethyl-3,4-dihydro-pyrimido[4,5-d]pyrimidin-2(1H)-one;

7-(Pyridin-4-ylamino)-3-(2-methyl-3,5-dimethoxy-phenyl)-1-ethyl-3,4-dihydro-pyrimido[4,5-d]pyrimidin-2(1H)-one;

7-(Pyridin-4-ylamino)-3-(2,6-dichloro-3,5-dimethoxy-phenyl)-1-cyclopentyl-3,4-dihydro-pyrimido[4,5-d]pyrimidin-2(1H)-one;

3-(2-Chloro-3,5-dimethoxy-phenyl)-7-(4-diethylamino-butylamino)-3,4-dihydro-pyrimido[4,5-d]pyrimidin-2(1H)-one;

3-(2-Chloro-3,5-dimethoxy-phenyl)-7-[4-(2-diethylamino-ethoxy)-phenylamino]-3,4-dihydro-pyrimido[4,5-d]pyrimidin-2(1H)-one;

3-(2-Chloro-3,5-dimethoxy-phenyl)-7-(pyridin-4-ylamino)-3,4-dihydro-pyrimido[4,5-d]pyrimidin-2(1H)-one;

3-(3,5-Dimethoxy-phenyl)-7-(pyridin-4-ylamino)-3,4-dihydro-pyrimido[4,5-d]pyrimidin-2(1H)-one;

7-[4-(2-Diethylamino-ethoxy)-phenylamino]-3-(3,5-dimethoxy-phenyl)-3,4-dihydro-pyrimido[4,5-d]pyrimidin-2(1H)-one;

3-(2,6-Dichloro-3,5-dimethoxy-phenyl)-7-(pyridin-4-ylamino)-3,4-dihydro-pyrimido[4,5-d]pyrimidin-2(1H)-one; and 3-(2,6-Dichloro-3,5-dimethoxy-phenyl)-7-[4-(2-diethylamino-ethoxy)-phenylamino]-3,4-dihydro-pyrimido[4,5-d]pyrimidin-2(1H)-one.

6. A compound of formula II

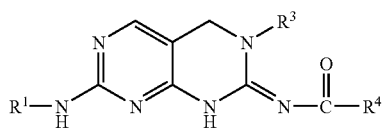

II or a pharmaceutically acceptable salt thereof,
wherein:

$R^1$ is selected from the group consisting of H, $(CH_2)_n Ar$, $COR^4$, $(CH_2)_n$heteroaryl, $(CH_2)_n$heterocyclyl, $C_1$-$C_{10}$ alkyl, $C_3$-$C_{10}$ cycloalkyl, $C_2$-$C_{10}$ alkenyl, and $C_2$-$C_{10}$ alkynyl, wherein n is 0, 1, 2, or 3, and the $(CH_2)_n Ar$, $(CH_2)_n$heteroaryl, alkyl, cycloalkyl, alkenyl, and alkynyl groups are optionally substituted by up to 5 groups selected from $NR^4R^5$, $N^+(O)R^4R^5$, $N^+R^4R^5R^6Y^-$, alkyl, phenyl, substituted phenyl, $(CH_2)_n$heteroaryl, hydroxy, alkoxy, phenoxy, thiol, thioalkyl, halo, $COR^4$, $CO_2R^4$, $CONR^4R^5$, $SO_2NR^4R^5$, $SO_3R^4$, $PO_3R^4$, aldehyde, nitrile, nitro, heteroaryloxy, $T(CH_2)_m QR^4$, $C(O)T(CH_2)_m QR^4$, $NHC(O)T(CH_2)_m QR^4$, $T(CH_2)_m C(O)NR^4NR^5$, or $T(CH_2)_m CO_2R^4$ wherein each m is independently 1-6, T is O, S, $NR^4$, $N^+(O)R^4$, $N^+R^4R^6Y^-$, or $CR^4R^5$, and Q is O, S, $NR^5$, $N^+(O)R^5$, or $N^+R^5R^6Y^-$;

$R^3$ has the meanings of $R^1$, wherein $R^1$ is as defined above, as well as OH, $NR^4R^5$, $COOR^4$, $OR^4$, $CONR^4R^5$, $SO_2NR^4R^5$, $SO_3R^4$, $PO_3R^4$, $T(CH_2)_m QR^4$,

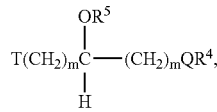

wherein T and Q are as defined above;

$R^4$ and $R^5$ are each independently selected from the group consisting of hydrogen, $C_1$-$C_6$ alkyl, substituted alkyl, $C_2$-$C_6$ alkenyl, $C_2$-$C_6$ alkynyl, $N(C_1$-$C_6alkyl)_1$ or 2 $(CH_2)_n Ar$, $C_3$-$C_{10}$ cycloalkyl, heterocyclyl, and heteroaryl, or $R^4$ and $R^5$ together with the nitrogen to which they are attached optionally form a ring having 3 to 7 carbon atoms and said ring optionally contains 1, 2, or 3 heteroatoms selected from the group consisting of nitrogen, substituted nitrogen, oxygen, and sulfur;

when $R^4$ and $R^5$ together with the nitrogen to which they are attached form a ring, the said ring is optionally substituted by 1 to 3 groups selected from OH, $OR^4$, $NR^4R^5$, $(CH_2)_m OR^4$, $(CH_2)_m NR^4R^5$, $T—(CH_2)_m QR_4$, $CO—T—(CH_2)_m QR^4$, $NH(CO)T(CH_2)_m QR^4$, $T—(CH_2)_m CO_2R^4$, or $T(CH_2)_m CONR^4R^5$;

$R^6$ is alkyl; and

Y is a halo counter-ion.

7. A compound selected from:

1-[7-[4-(2-Diethylamino-ethoxy)-phenylamino]-3-(3,5-dimethoxy-phenyl)-3,4-dihydro-pyrimido[4,5-d]pyrimidin-2-yl]-3-ethyl-urea;

1-{3-(2-Chloro-3,5-dimethoxy-phenyl)-7-[4-(2-dimethylamino-ethoxy)-phenylamino]-3,4-dihydro-pyrimido[4,5-d]pyrimidin-2-yl}-3-ethyl-urea;

1-tert-Butyl-3-[7-[4-(2-diethylamino-ethoxy)-phenylamino]-3-(3,5-dimethoxy-phenyl)-3,4-dihydro-pyrimido[4,5-d]pyrimidin-2-yl]-urea;

1-tert-Butyl-3-{3-(2-chloro-3,5-dimethoxy-phenyl)-7-[4-(2-diethylamino-ethoxy)-phenylamino]-3,4-dihydro-pyrimido[4,5-d]pyrimidin-2-yl}-urea;

1-tert-Butyl-3-[3-(3,5-dimethoxy-phenyl)-7-(pyridin-4-ylamino)-3,4-dihydro-pyrimido[4,5-d]pyrimidin-2-yl]-urea;

1-[3-(3,5-Dimethoxy-phenyl)-7-(pyridin-4-ylamino)-3,4-dihydro-pyrimido[4,5-d]pyrimidin-2-yl]-3-ethyl-urea;

1-tert-Butyl-3-[3-(2-chloro-3,5-dimethoxy-phenyl)-7-(pyridin-4-ylamino)-3,4-dihydro-pyrimido[4,5-d]pyrimidin-2-yl]-urea;

1-[3-(2-Chloro-3,5-dimethoxy-phenyl)-7-(pyridin-4-ylamino)-3,4-dihydro-pyrimido[4,5-d]pyrimidin-2-yl]-3-ethyl-urea;

1-[3-(2-Chloro-3,5-dimethoxy-phenyl)-7-(4-diethylamino-butylamino)-3,4-dihydro-pyrimido[4,5-d]pyrimidin-2-yl]-3-ethyl-urea;

3-Methyl-N-{7-[4-(5-methyl-hexahydro-pyrrolo[3,4-c]pyrrol-2-yl)-phenylamino]-3,4-dihydro-pyrimido[4,5-d]pyrimidin-2-yl}-butyramide;

1-{7-[4-(4-Acetyl-piperazin-1-yl)-phenylamino]-3,4-dihydro-pyrimido[4,5-d]pyrimidin-2-yl}-3-isopropyl-urea; and 1-tert-Butyl-3-[3-(2-chloro-3,5-dimethoxy-phenyl)-7-(4-diethylamino-butylamino)-3,4-dihydro-pyrimido[4,5-d]pyrimidin-2-yl]-urea.

8. A compound of formula III

III or a pharmaceutically acceptable salt thereof,
wherein:

$R^1$ is selected from the group consisting of H, $(CH_2)_n Ar$, $COR^4$, $(CH_2)_n$heteroaryl, $(CH_2)_n$heterocyclyl, $C_1$-$C_{10}$ alkyl, $C_3$-$C_{10}$ cycloalkyl, $C_2$-$C_{10}$ alkenyl, and $C_2$-$C_{10}$ alkynyl, wherein n is 0, 1, 2, or 3, and the $(CH_2)_n Ar$, $(CH_2)_n$heteroaryl, alkyl, cycloalkyl, alkenyl, and alkynyl groups are optionally substituted by up to 5 groups selected from $NR^4R^5$, $N^+(O)R^4R^5$, $N^+R^4R^5R^6Y^-$, alkyl, phenyl, substituted phenyl, $(CH_2)_n$heteroaryl, hydroxy, alkoxy, phenoxy, thiol, thioalkyl, halo, $COR^4CO_2R^4$, $CONR^4R^5$, $SO_2NR^4R^5$, $SO_3R^4$, $PO_3R^4$, aldehyde, nitrile, nitro, heteroaryloxy, $T(CH_2)_m QR^4$,

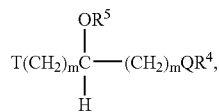

C(O)T(CH$_2$)$_m$QR$^4$NHC(O)T(CH$_2$)$_m$QR$^4$, T(CH$_2$)$_m$C(O)NR$^4$NR$^5$, or T(CH$_2$)$_m$CO$_2$R$^4$ wherein each m is independently 1-6, T is O, S, NR$^4$, N$^+$(O)R$^4$, N$^+$R$^4$R$^6$Y$^-$, or CR$^4$R$^5$, and Q is O, S, NR$^5$, N$^+$(O)R$^5$, or N$^+$R$^5$R$^6$Y$^-$;

R$^4$ and R$^5$ are each independently selected from the group consisting of hydrogen, C$_1$-C$_6$ alkyl substituted alkyl, C$_2$-C$_6$ alkenyl, C$_2$-C$_6$ alkynyl, N(C$_1$-C$_6$alkyl)$_1$ or $_2$ (CH$_2$)$_n$Ar, C$_3$-C$_{10}$ cycloalkyl, heterocyclyl, and heteroaryl, or R$^4$ and R$^5$ together with the nitrogen to which they are attached optionally form a ring having 3 to 7 carbon atoms and said ring optionally contains 1, 2, or 3 heteroatoms selected from the group consisting of nitrogen, substituted nitrogen, oxygen, and sulfur;

when R$^4$ and R$^5$ together with the nitrogen to which they are attached form a ring, the said ring is optionally substituted by 1 to 3 groups selected from OH, OR$^4$, NR$^4$R$^5$, (CH$_2$)$_m$OR$^4$, (CH$_2$)$_m$NR$^4$R$^5$, T—(CH$_2$)$_m$QR$_4$, CO—T—(CH$_2$)$_m$QR$^4$, NH(CO)T(CH$_2$)$_m$QR$^4$, T—(CH$_2$)$_m$CO$_2$R$^4$, or T(CH$_2$)$_m$CONR$^4$R$^5$;

R$^6$ is alkyl; and

Y is a halo counter-ion.

9. A compound selected from:
1-[7-(4-Fluoro-phenylamino)-pyrimido[4,5-d]pyrimidin-2-yl]-3-methyl-urea;
1-Isopropyl-3-(7-phenylamino-pyrimido[4,5-d]pyrimidin-2-yl)-urea;
1-{7-[4-(3-Aminomethyl-pyrrolidin-1-yl)-phenylamino]-pyrimido[4,5-d]pyrimidin-2-yl}-3-isopropyl-urea;
1-Isopropyl-3-[7-(4-piperazin-1-yl-phenylamino)-pyrimido[4,5-d]pyrimidin-2-yl]-urea;
1-{7-[4-(4-Acetyl-piperazin-1-yl)-phenylamino]-pyrimido[4,5-d]pyrimidin-2-yl}-3-isopropyl-urea;
N-{7-[4-(3-Amino-pyrrolidin-1-yl)-phenylamino]-pyrimido[4,5-d]pyrimidin-2-yl}-3-methyl-butyramide;
N-[7-(4-piperazin-1-yl-phenylamino)-pyrimido[4,5-d]pyrimidin-2-yl]-isobutyramide;
N-{7-[4-(4-Acetyl-piperazin-1-yl)-phenylamino]-pyrimido[4,5-d]pyrimidin-2-yl}-3-methyl-butyramide;
3-Methyl-N-[7-(pyridin-4-ylamino)-pyrimido[4,5-d]pyrimidin-2-yl]-butyramide;
1-Isopropyl-3-[7-(pyridin-4-ylamino)-pyrimido[4,5-d]pyrimidin-2-yl]-urea; and
N-{7-[4-(3-Aminomethyl-pyrrolidin-1-yl)-phenylamino]-pyrimido[4,5-d]pyrimidin-2-yl}-3-methyl-butyramide.

10. A compound of Formula IV

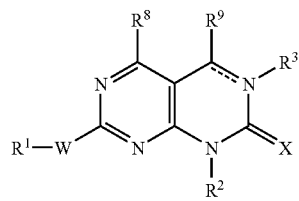

IV or a pharmaceutically acceptable salt thereof,
wherein:
the dotted line represents an optional double bond;
W is S, SO, or SO$_2$;
X is either O, S, or NR$^{10}$;

R$^1$, R$^2$, and R$^{10}$ are independently selected from the group consisting of H, (CH$_2$)$_n$Ar, COR$^4$, (CH$_2$)$_n$heteroaryl, (CH$_2$)$_n$heterocyclyl, C$_1$-C$_{10}$ alkyl, C$_3$-C$_{10}$ cycloalkyl, C$_2$-C$_{10}$ alkenyl, and C$_2$-C$_{10}$ alkynyl, wherein n is 0, 1, 2, or 3, and the (CH$_2$)$_n$Ar, (CH$_2$)$_n$heteroaryl, alkyl, cycloalkyl, alkenyl, and alkynyl groups are optionally substituted by up to 5 groups selected from NR$^4$R$^5$, N$^+$(O)R$^4$R$^5$, N$^+$R$^4$R$^5$R$^6$Y$^-$, alkyl, phenyl, substituted phenyl, (CH$_2$)$_n$heteroaryl, hydroxy, alkoxy, phenoxy, thiol, thioalkyl, halo, COR$^4$CO$_2$R$^4$, CONR$^4$R$^5$, SO$_2$NR$^4$R$^5$, SO$_3$R$^4$, PO$_3$R$^4$, aldehyde, nitrile, nitro, heteroaryloxy,

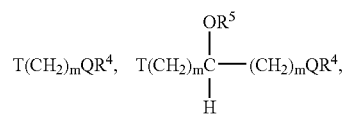

C(O)T(CH$_2$)$_m$QR$^4$, NHC(O)T(CH$_2$)$_m$QR$^4$, T(CH$_2$)$_m$C(O)NR$^4$NR$^5$, or T(CH$_2$)$_m$CO$_2$R$^4$ wherein each m is independently 1-6, T is O, S, NR$^4$, N$^+$(O)R$^4$, N$^+$R$^4$R$^6$Y$^-$, or CR$^4$R$^5$, and Q is O, S, NR$^5$, N$^+$(O)R$^5$, or N$^+$R$^5$R$^6$Y$^-$;

when the dotted line is present, R$^3$ is absent;
otherwise R$^3$ has the meanings of R$^2$, wherein R$^2$ is as defined above, as well as OH, NR$^4$R$^5$, COOR$^4$, OR$^4$, CONR$^4$R$^5$, SO$_2$NR$^4$R$^5$SO$_3$R$^4$, PO$_3$R$^4$,

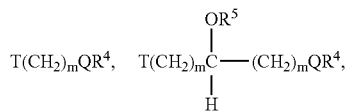

wherein T and Q are as defined above;
R$^4$ and R$^5$ are each independently selected from the group consisting of hydrogen, C$_1$-C$_6$ alkyl substituted alkyl, C$_2$-C$_6$ alkenyl, C$_2$-C$_6$ alkynyl, N(C$_1$-C$_6$alkyl)$_1$ or $_2$, (CH$_2$)$_n$Ar, C$_3$-C$_{10}$ cycloalkyl, heterocyclyl, and heteroaryl, or R$^4$ and R$^5$ together with the nitrogen to which they are attached optionally form a ring having 3 to 7 carbon atoms and said ring optionally contains 1, 2, or 3 heteroatoms selected from the group consisting of nitrogen, substituted nitrogen, oxygen, and sulfur;

when R$^4$ and R$^5$ together with the nitrogen to which they are attached form a ring, the said ring is optionally substituted by 1 to 3 groups selected from OH, OR$^4$NR$^4$R$^5$, (CH$_2$)$_m$OR$^4$, (CH$_2$)$_m$NR$^4$R$^5$, T—(CH$_2$)$_m$QR$^4$T—CH$_2$)$_m$QR$^4$, NH(CO)T(CH$_g$)$_m$QR$^4$, T—(CH$_2$)$_m$CO$_2$R$^4$, or T(CH$_2$)$_m$CONR$^4$R$^5$;

R$^6$ is alkyl;

R$^8$ and R$^9$ independently are H, C$_1$-C$_3$ alkyl, NR$^4$R$^5$, N$^+$(O)R$^4$R$^5$, N$^+$R$^4$R$^5$R$^6$Y$^-$, hydroxy, alkoxy, thiol, thioalkyl, halo, COR$^4$, CO$_2$R$^4$, CONR$^4$R$^5$, SO$_2$NR$^4$R$^5$, SO$_3$R$^4$, PO$_3$R$^4$, CHO, CN or NO$_2$;

when the dotted line is absent, R$^9$ is additionally oxo,

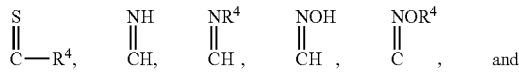

Y is a halo counter-ion.

11. A compound of formula V

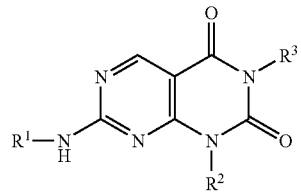

or a pharmaceutically acceptable salt thereof,
wherein:

$R^1$ and $R^2$ are independently selected from the group consisting of $(CH_2)_nAr$, $COR^4$, $(CH_2)_n$heteroaryl, $(CH_2)_n$heterocyclyl, $C_3$-$C_{10}$ cycloalkyl, $C_2$-$C_{10}$ alkenyl, and $C_2$-$C_{10}$ alkynyl, wherein n is 0, 1, 2, or 3, and the $(CH_2)_n$Ar, $(CH_2)_n$heteroaryl, alkyl, cycloalkyl, alkenyl, and alkynyl groups are optionally substituted by up to 5 groups selected from $NR^4R^5$, $N^+(O)R^4R^5$, $N^+R^4R^5R^6Y^-$, alkyl, phenyl, substituted phenyl, $(CH_2)_n$heteroaryl, hydroxy, alkoxy, phenoxy, thiol, thioalkyl, halo, $COR^4$, $CO_2R^4$, $CONR^4R^5$, $SO_2NR^4R^5$, $SO_3R^4$, $PO_3R^4$, aldehyde, nitrile, nitro, heteroaryloxy, $T(CH_2)_mQR^4$,

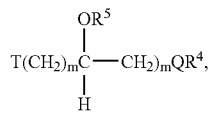

$C(O)T(CH_2)_mQR^4$, $NHC(O)T(CH_2)_mQR^4$, $T(CH_2)_mC(O)NR^4NR^5$, or $T(CH_2)_mCO_2R^4$ wherein each m is independently 1-6, T is O, S, $NR^4$, $N^+(O)R^4$, $N^+R^4R^6Y^-$, or $CR^4R^5$, and Q is O, S, $NR^5$, $N^+(O)R^5$, or $N^+R^5R^6Y^-$;

$R^3$ has the meanings of $R^2$, wherein $R^2$ is as defined above, as well as OH, $NR^4R^5$, $COOR^4$, $OR^4$, $CONR^4R^5$, $SO_2NR^4R^5$, $SO_3R^4$, $PO_3R^4$, $T(CH_2)_mQR^4$,

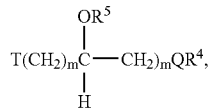

wherein T and Q are as defined above;

$R^4$ and $R^5$ are each independently selected from the group consisting of hydrogen, $C_1$-$C_6$ alkyl substituted alkyl, $C_2$-$C_6$ alkenyl, $C_2$-$C_6$ alkynyl, $N(C_1$-$C_6alkyl)_1$ or $_2$ $(CH_2)_nAr$, $C_3$-$C_{10}$ cycloalkyl, heterocyclyl, and heteroaryl, or $R^4$ and $R^5$ together with the nitrogen to which they are attached optionally form a ring having 3 to 7 carbon atoms and said ring optionally contains 1, 2, or 3 heteroatoms selected from the group consisting of nitrogen, substituted nitrogen, oxygen, and sulfur;

when $R^4$ and $R^5$ together with the nitrogen to which they are attached form a ring, the said ring is optionally substituted by 1 to 3 groups selected from OH, $OR^4$, $NR^4R^5$, $(CH_2)_mOR^4$, $CH_2)_mNR^4R^5$, $T-(CL)_mQR_4$, $CO-T-CH_2)_mQR^4$, $NH(CO)T(CH_2)_mQR^4$, $T-(CH_2)_mCO_2R^4$, or $T(CH_2)_mCONR^4R^5$;

$R^6$ is alkyl; and

Y is a halo counter-ion.

12. A compound selected from:

1-Isopropyl-7-[4-(4-methylpiperazin-1-yl)phenylamino]-1H-pyrimido[4,5-d]pyrimidine-2,4-dione;

7-[4-(2-Diethylaminoethoxy)phenylamino]-1-isopropyl-1H-pyrimido[4,5-d]pyrimidine-2,4-dione;

7-(4-Diethylamino-butylamino)-3-(3,5-dimethoxy-phenyl)-1-ethyl-1H-pyrimido[4,5-d]pyrimidine-2,4-dione;

7-[4-(2-Diethylamino-ethoxy)-phenylamino]-3-(3,5-dimethoxy-phenyl)-1-ethyl-1H-pyrimido[4,5-d]pyrimidine-2,4-dione; and 7-(Pyridin-4-ylamino)-3-(3,5-dimethoxy-phenyl)-1-ethyl-1H-pyrimido[4,5-d]pyrimidine-2,4-dione.

13. A method of inhibiting a cyclin-dependent kinase comprising contacting the cyclin-dependent kinase with a compound of Formula VI

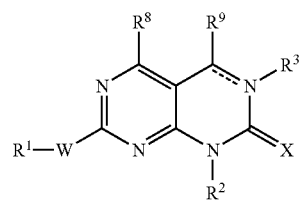

or a pharmaceutically acceptable salt thereof,
wherein:

the dotted line represents an optional double bond;

W is NH, S, SO, or $SO_2$;

X is either O, S, or $NR^{10}$;

$R^1$, $R^2$, and $R^{10}$ are independently selected from the group consisting of H, $(CH_2)_nAr$, $COR^4$, $(CH_2)_n$heteroaryl, $(CH_2)_n$heterocyclyl, $C_1$-$C_{10}$ alkyl, $C_3$-$C_{10}$ cycloalkyl, $C_2$-$C_{10}$ alkenyl, and $C_2$-$C_{10}$ alkynyl, wherein n is 0, 1, 2, or 3, and the $(CH_2)_nAr$, $(CH_2)_n$heteroaryl, alkyl, cycloalkyl, alkenyl, and alkynyl groups are optionally substituted by up to 5 groups selected from $NR^4R^5$, $N^+(O)R^4R^5$, $N^+R^4R^5R^6Y^-$, alkyl, phenyl, substituted phenyl, $(CH_2)_n$heteroaryl, hydroxy, alkoxy, phenoxy, thiol, thioalkyl, halo, $COR^4$, $CO_2R^4$, $CONR^4R^5$, $SO_2NR^4R^5$, $SO_3R^4$, $PO_3R^4$, aldehyde, nitrile, nitro, heteroaryloxy,

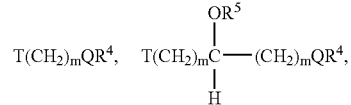

$C(O)T(CH_2)_mQR^4$, $NHC(O)T(CH_2)_mQR^4$, $T(CH_2)_mC(O)NR^4NR^5$, or $T(CH_2)_mCO_2R^4$ wherein each m is independently 1-6, T is O, S, $NR^4$, $N^+(O)R^4$, $N^+R^4R^6Y^-$, or $CR^4R^5$, and Q is O, S, $NR^5$, $N^+(O)R^5$, or $N^+R^5R^6Y^-$;

when the dotted line is present, $R^3$ is absent;

otherwise $R^3$ has the meanings of $R^2$, wherein $R^2$ is as defined above, as well as OH, $NR^4R^5$, $COOR^4$, $OR^4$, $CONR^4R^5$, $SO_2NR^4R^5$, $SO_3R^4$, $PO_3R^4$, $T(CH_2)_mQR^4$,

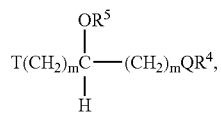

wherein T and Q are as defined above;

$R^4$ and $R^5$ are each independently selected from the group consisting of hydrogen, $C_1$-$C_6$ alkyl, substituted alkyl, $C_2$-$C_6$ alkenyl, $C_2$-$C_6$ alkynyl, $N(C_1$-$C_6alkyl)_1$ or 2, $(CH_2)_nAr$, $C_3$-$C_{10}$ cycloalkyl, heterocyclyl, and heteroaryl, or $R^4$ and $R^5$ together with the nitrogen to which they are attached optionally form a ring having 3 to 7 carbon atoms and said ring optionally contains 1, 2, or 3 heteroatoms selected from the group consisting of nitrogen, substituted nitrogen, oxygen, and sulfur;

when $R^4$ and $R^5$ together with the nitrogen to which they are attached form a ring, the said ring is optionally substituted by 1 to 3 groups selected from OH, $OR^4$, $NR^4R^5$, $(CH_2)_mOR^4$, $(CH_2)_mNR^4R^5$, T—$(CH_2)_mQR_4$, CO—T—$(CH_2)_mQR^4$, NH(CO)T$(CH_2)_mQR^4$, T—$(CH_2)_mCO_2R^4$, or T$(CH_2)_mCONR^4R^5$;

$R^6$ is alkyl;

$R^8$ and $R^9$ independently are H, $C_1$-$C_3$ alkyl, $NR^4R^5$, $N^+(O)R^4R^5$, $N^+R^4R^5R^6Y^-$, hydroxy, alkoxy, thiol, thioalkyl, halo, $COR^4$, $CO_2R^4$, $CONR^4R^5$, $SO_2NR^4R^5$, $SO_3R^4$, $PO_3R^4$, CHO, CN, or $NO_2$;

when the dotted line is absent, $R^9$ is additionally oxo,

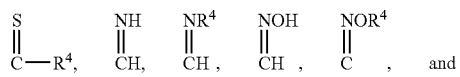

Y is a halo counter-ion.

14. The method of claim 13 wherein said cyclin-dependent kinase is cdc2.
15. The method of claim 13 wherein said cyclin-dependent kinase is cdk2.
16. The method of claim 13 wherein said cyclin-dependent kinase is cdk4 or cdk6.
17. A method of inhibiting a growth factor-mediated tyrosine kinase comprising contacting said growth factor-mediated kinase with a compound of Formula VI

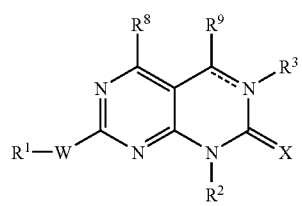

or a pharmaceutically acceptable salt thereof,
wherein:
the dotted line represents an optional double bond;
W is NH, S, SO, or $SO_2$;
X is either O, S, or $NR^{10}$;
$R^1$, $R^2$, and $R^{10}$ are independently selected from the group consisting of H, $(CH_2)_nAr$, $COR^4$, $(CH_2)_n$heteroaryl, $(CH_2)_n$heterocyclyl, $C_1$-$C_{10}$ alkyl, $C_3$-$C_{10}$ cycloalkyl, $C_2$-$C_{10}$ alkenyl, and $C_2$-$C_{10}$ alkynyl, wherein n is 0, 1, 2, or 3, and the $(CH_2)_nAr$, $(CH_2)_n$heteroaryl, alkyl, cycloalkyl, alkenyl, and alkynyl groups are optionally substituted by up to 5 groups selected from $NR^4R^5$, $N^+(O)R^4R^5$, $N^+R^4R^5R^6Y^-$, alkyl, phenyl, substituted phenyl, $(CH_2)_n$heteroaryl, hydroxy, alkoxy, phenoxy, thiol, thioalkyl, halo, $COR^4$, $CO_2R^4$, $CONR^4R^5$, $SO_2NR^4R^5$, $SO_3R^4$, $PO_3R^4$, aldehyde, nitrile, nitro, heteroaryloxy, T$(CH_2)_mQR^4$,

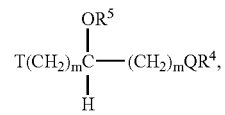

C(O)T$(CH_2)_mQR^4$, NHC(O)T$(CH_2)_mQR^4$, T$(CH_2)_mC(O)NR^4NR^5$, or T$(CH_2)_mCO_2R^4$ wherein each m is independently 1-6, T is O, S, $NR^4$, $N^+(O)R^4$, $N^+R^4R^6Y^-$, or $CR^4R^5$, and Q is O, S, $NR^5$, $N^+(O)R^5$, or $N^+R^5R^6Y^-$;

when the dotted line is present, $R^3$ is absent;

otherwise $R^3$ has the meanings of $R^2$, wherein $R^2$ is as defined above, as well as OH, $NR^4R^5$, $COOR^4$, $OR^4$, $CONR^4R^5$, $SO_2NR^4R^5$, $SO_3R^4$, $PO_3R^4$, T$(CH_2)_mQR^4$,

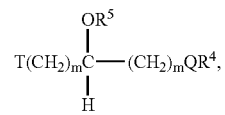

wherein T and Q are as defined above;

$R^4$ and $R^5$ are each independently selected from the group consisting of hydrogen, $C_1$-$C_6$ alkyl, substituted alkyl, $C_2$-$C_6$ alkenyl, $C_2$-$C_6$ alkynyl, $N(C_1$-$C_6alkyl)_1$ or 2, $(CH_2)_nAr$, $C_3$-$C_{10}$ cycloalkyl, heterocyclyl, and heteroaryl, or $R^4$ and $R^5$ together with the nitrogen to which they are attached optionally form a ring having 3 to 7 carbon atoms and said ring optionally contains 1, 2, or 3 heteroatoms selected from the group consisting of nitrogen, substituted nitrogen, oxygen, and sulfur;

when $R^4$ and $R^5$ together with the nitrogen to which they are attached form a ring, the said ring is optionally substituted by 1 to 3 groups selected from OH, $OR^4$, $NR^4R^5$, $(CH_2)_mOR^4$, $(CH_2)_mNR^4R^5$, T—$(CH_2)_mQR_4$, CO—T—$(CH_2)_mQR^4$, NH(CO)T$(CH_2)_mQR^4$, T—$(CH_2)_mCO_2R^4$, or T$(CH_2)_mCONR^4R^5$;

$R^6$ is alkyl;

$R^8$ and $R^9$ independently are H, $C_1$-$C_3$ alkyl, $NR^4R^5$, $N^+(O)R^4R^5$, $N^+R^4R^5R^6Y^-$, hydroxy, alkoxy, thiol, thioalkyl, halo, $COR^4$, $CO_2R^4$, $CONR^4R^5$, $SO_2NR^4R^5$, $SO_3R^4$, $PO_3R^4$, CHO, CN, or $NO_2$;

when the dotted line is absent, $R^9$ is additionally oxo,

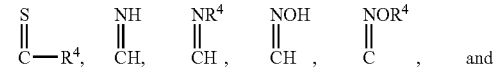

Y is a halo counter-ion.

18. The method of claim 17 wherein said growth factor-mediated tyrosine kinase is platelet derived growth factor (PDGF).

19. The method of claim 17 wherein said growth factor-mediated tyrosine kinase is fibroblast growth factor (FGF).

20. The method of claim 17 wherein said growth factor-mediated tyrosine kinase is vascular endothelial growth factor (VEGF).

21. A method of inhibiting a non-receptor tyrosine kinase comprising contacting said non-receptor tyrosine kinase with a compound of Formula VI

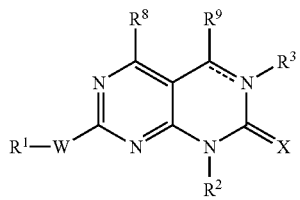

or a pharmaceutically acceptable salt thereof,
wherein:
the dotted line represents an optional double bond;
W is NH, S, SO, or $SO_2$;
X is either O, S, or $NR^{10}$;
$R^1$, $R^2$, and $R^{10}$ are independently selected from the group consisting of H, $(CH_2)_n Ar$, $COR^4$, $(CH_2)_n$heteroaryl, $(CH_2)_n$heterocyclyl, $C_1$-$C_{10}$ alkyl, $C_3$-$C_{10}$ cycloalkyl, $C_2$-$C_{10}$ alkenyl, and $C_2$-$C_{10}$ alkynyl, wherein n is 0, 1, 2, or 3, and the $(CH_2)_n Ar$, $(CH_2)_n$heteroaryl, alkyl, cycloalkyl, alkenyl, and alkynyl groups are optionally substituted by up to 5 groups selected from $NR^4R^5$, $N^+(O)R^4R^5$, $N^+R^4R^5R^6Y^-$, alkyl, phenyl, substituted phenyl, $(CH_2)_n$heteroaryl, hydroxy, alkoxy, phenoxy, thiol, thioalkyl, halo, $COR^4$, $CO_2R^4$, $CONR^4R^5$, $SO_2NR^4R^5$, $SO_3R^4$, $PO_3R^4$, aldehyde, nitrile, nitro, heteroaryloxy, $T(CH_2)_m QR^4$,

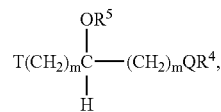

$C(O)T(CH_2)_m QR^4$, $NHC(O)T(CH_2)_m QR^4$, $T(CH_2)_m C(O)NR^4NR^5$, or $T(CH_2)_m CO_2R^4$ wherein each m is independently 1-6, T is O, S, $NR^4$, $N^+(O)R^4$, $N^+R^4R^6Y^-$, or $CR^4R^5$, and Q is O, S, $NR^5$, $N^+(O)R^5$, or $N^+R^5R^6Y^-$;
when the dotted line is present, $R^3$ is absent;
otherwise $R^3$ has the meanings of $R^2$, wherein $R^2$ is as defined above, as well as OH, $NR^4R^5$, $COOR^4$, $OR^4$, $CONR^4R^5$, $SO_2NR^4R^5$, $SO_3R^4$, $PO_3R^4$,
$T(CH_2)_m QR^4$,

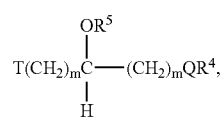

wherein T and Q are as defined above;

$R^4$ and $R^5$ are each independently selected from the group consisting of hydrogen, $C_1$-$C_6$ alkyl, substituted alkyl, $C_2$-$C_6$ alkenyl, $C_2$-$C_6$ alkynyl, $N(C_1$-$C_6 alkyl)_1$ or 2, $(CH_2)_n Ar$,
$C_3$-$C_{10}$ cycloalkyl, heterocyclyl, and heteroaryl, or $R^4$ and $R^5$ together with the nitrogen to which they are attached optionally form a ring having 3 to 7 carbon atoms and said ring optionally contains 1, 2, or 3 heteroatoms selected from the group consisting of nitrogen, substituted nitrogen, oxygen, and sulfur;
when $R^4$ and $R^5$ together with the nitrogen to which they are attached form a ring, the said ring is optionally substituted by 1 to 3 groups selected from OH, $OR^4$, $NR^4R^5$, $(CH_2)_m OR^4$,
$(CH_2)_m NR^4R^5$, $T-(CH_2)_m QR_4$, $CO-T-(CH_2)_m QR^4$, $NH(CO)T(CH_2)_m QR^4$, $T-(CH_2)_m CO_2R^4$, or $T(CH_2)_m CONR^4R^5$;
$R^6$ is alkyl;
$R^8$ and $R^9$ independently are H, $C_1$-$C_3$ alkyl, $NR^4R^5$, $N^+(O)R^4R^5$, $N^+R^4R^5R^6Y^-$, hydroxy, alkoxy, thiol, thioalkyl, halo, $COR^4$, $CO_2R^4$, $CONR^4R^5$, $SO_2NR^4R^5$, $SO_3R^4$, $PO_3R^4$, CHO, CN, or $NO_2$;
when the dotted line is absent, $R^9$ is additionally oxo,

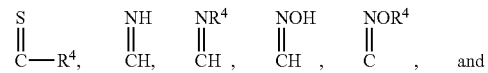

Y is a halo counter-ion.

22. The method of claim 21 wherein said non-receptor tyrosine kinase is selected from a transforming gene of the Rous sarcoma retrovirus (Src) family.

23. A method of inhibiting a serine kinase in a mammal comprising administering a serine kinase inhibiting among of a compound of Formula VI

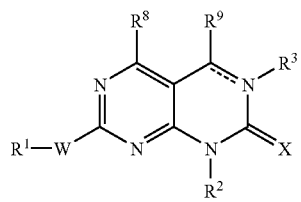

or a pharmaceutically acceptable salt thereof,
wherein:
the dotted line represents an optional double bond;
W is NH, S, SO, or $SO_2$;
X is either O, S, or $NR^{10}$;
$R^1$, $R^2$, and $R^{10}$ are independently selected from the group consisting of H, $(CH_2)_n Ar$, $COR^4$, $(CH_2)_n$heteroaryl, $(CH_2)_n$heterocyclyl, $C_1$-$C_{10}$ alkyl, $C_3$-$C_{10}$ cycloalkyl, $C_2$-$C_{10}$ alkenyl, and $C_2$-$C_{10}$ alkynyl, wherein n is 0, 1, 2, or 3, and the $(CH_2)_n Ar$, $(CH_2)_n$heteroaryl, alkyl, cycloalkyl, alkenyl, and alkynyl groups are optionally substituted by up to 5 groups selected from $NR^4R^5$, $N^+(O)R^4R^5$, $N^+R^4R^5R^6Y^-$, alkyl, phenyl, substituted phenyl, $(CH_2)_n$heteroaryl, hydroxy, alkoxy, phenoxy, thiol, thioalkyl, halo, $COR^4 CO_2R^4$, $CONR^4R^5$, $SO_2NR^4R^5$, $SO_3R^4$, $PO_3R$, aldehyde, nitrile, nitro, heteroaryloxy, $T(CH_2)_m QR^4$,

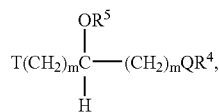

C(O)T(CH$_2$)$_m$QR$^4$, NHC(O)T(CH$_2$)$_m$QR$^4$, T(CH$_2$)$_m$C(O)NR$^4$NR$^5$, or T(CH$_2$)$_m$CO$_2$R$^4$ wherein each m is independently 1-6, T is O, S, NR$^4$, N$^+$(O)R$^4$, N$^+$R$^4$R$^6$Y$^-$, or CR$^4$R$^5$, and Q is O, S, NR$^5$, N$^+$(O)R$^5$, or N$^+$R$^5$R$^6$Y$^-$;

when the dotted line is present, R$^3$ is absent;

otherwise R$^3$ has the meanings of R$^2$, wherein R$^2$ is as defined above, as well as OH, NR$^4$R$^5$, COOR$^4$, OR$^4$, CONR$^4$R$^5$, SO$_2$NR$^4$R$^5$, SO$_3$R$^4$, PO$_3$R$^4$, T(CH$_2$)$_m$QR$^4$,

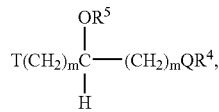

wherein T and Q are as defined above;

R$^4$ and R$^5$ are each independently selected from the group consisting of hydrogen, C$_1$-C$_6$ alkyl substituted alkyl, C$_2$-C$_6$ alkenyl, C$_2$-C$_6$ alkynyl, N(C$_1$-C$_6$alkyl)$_1$ or 2 (CH$_2$)$_n$Ar, C$_3$-C$_{10}$ cycloalkyl, heterocyclyl, and heteroaryl, or R$^4$ and R$^5$ together with the nitrogen to which they are attached optionally form a ring having 3 to 7 carbon atoms and said ring optionally contains 1, 2, or 3 heteroatoms selected from the group consisting of nitrogen, substituted nitrogen, oxygen, and sulfur;

when R$^4$ and R$^5$ together with the nitrogen to which they are attached form a ring, the said ring is optionally substituted by 1 to 3 groups selected from OH, OR$^4$, NR$^4$R$^5$, (CH$_2$)$_m$OR$^4$, (CH$_2$)$_m$NR$^4$R$^5$, T—(CH$_2$)$_m$QR$^4$T—CH$_2$)$_m$QR$^4$, NH(CO)T(CH$_2$)$_m$QR$^4$, T—(CH$_2$)$_m$CO$_2$R$^4$, or T(CH$_2$)$_m$CONR$^4$R$^5$;

R$^6$ is alkyl;

R$^8$ and R$^9$ independently are H, C$_1$-C$_3$ alkyl, NR$^4$R$^5$, N$^+$(O)R$^4$R$^5$, N$^+$R$^4$R$^5$R$^6$Y$^-$, hydroxy, alkoxy, thiol, thioalkyl, halo, COR$^4$CO$_2$R$^4$CONR$^4$R$^5$SO$_2$R$^4$R$^5$ SO$_3$R$^4$PO$_3$R$^4$, CHO, CN or NO$_2$;

when the dotted line is absent, R$^9$ is additionally oxo,

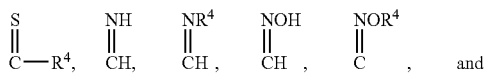

Y is a halo counter-ion.

24. A compound selected from:
7-[3-(Carboxy)-phenylamino]-3-(2,6-dichloro-phenyl)-1-methyl-3,4-dihydro-pyrimido[4,5-d]pyrimidin-2(1H)-one;
7-[3-(N-Dimethylaminopropyl-carboxamide)-phenylamino]-3-(2,6-dichloro-phenyl)-1-methyl-3,4-dihydro-pyrimido[4,5-d]pyrimidin-2(1H)-one;
7-[3-(N-Dimethylaminopropyl-carboxamide)-phenylamino]-3-(2,6-dichloro-3-hydroxy-phenyl)-1-methyl-3,4-dihydro-pyrimido[4,5-d]pyrimidin-2(1H)-one;
7-[3-(Carboxy)-phenylamino]-3-(2,6-dichloro-3-hydroxy-phenyl)-1-methyl-3,4-dihydro-pyrimido[4,5-d]pyrimidin-2(1H)-one;
3-(2,6-Dichloro-phenyl)-7-[4-(2-ethylamino-ethoxy)-phenylamino]-1-methyl-3,4-dihydro-pyrimido[4,5-d]pyrimidin-2(1H)-one;
3-(2,6-Dichloro-3-hydroxy-phenyl)-7-[4-(2-ethylamino-ethoxy)-phenylamino]-1-methyl-3,4-dihydro-pyrimido[4,5-d]pyrimidin-2(1H)-one;
7-[4-(Carboxamide)-phenylamino]-3-(2,6-dichloro-phenyl)-1-methyl-3,4-dihydro-pyrimido[4,5-d]pyrimidin-2(1H)-one;
7-[4-(Carboxamide)-phenylamino]-3-(2,6-dichloro-3-hydroxy-phenyl)-1-methyl-3,4-dihydro-pyrimido[4,5-d]pyrimidin-2(1H)-one;
3-(2,6-Dichloro-phenyl)-7-(3-hydroxymethyl-phenylamino)-1-methyl-3,4-dihydro-pyrimido[4,5-d]pyrimidin-2(1H)-one;
3-(2,6-Dichloro-phenyl)-7-(4-morpholin-4-yl-phenylamino)-3,4-dihydro-pyrimido[4,5-d]pyrimidin-2(1H)-one;
3-(2,6-Dichloro-3-hydroxy-phenyl)-1-methyl-7-(4-morpholin-4-yl-phenylamino)-3,4-dihydro-pyrimido[4,5-d]pyrimidin-2(1H)-one;
3-(2,6-Dichloro-3-hydroxy-phenyl)-7-(3-hydroxymethyl-phenylamino)-1-methyl-3,4-dihydro-pyrimido[4,5-d]pyrimidin-2(1H)-one;
7-[4-(3-Carboxypropyl)-phenylamino]-3-(2,6-dichloro-phenyl)-1-methyl-3,4-dihydro-pyrimido[4,5-d]pyrimidin-2(1H)-one;
7-[4-(3-Carboxypropyl)-phenylamino]-3-(2,6-dichloro-3-hydroxy-phenyl)-1-methyl-3,4-dihydro-pyrimido[4,5-d]pyrimidin-2(1H)-one;
3-(2,6-Dichloro-phenyl)-7-[4-(formyl-phenylamino]-1-methyl-3,4-dihydro-pyrimido[4,5-d]pyrimidin-2(1H)-one; and
3-(2,6-Dichloro-3-hydroxy-phenyl)-7-[4-(formyl-phenylamino]-1-methyl-3,4-dihydro-pyrimido[4,5-d]pyrimidin-2(1H)-one.

25. A compound of the formula

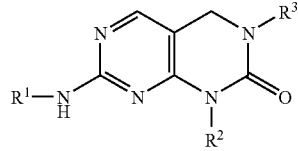

wherein:

R$^1$ is C$_1$-C$_{10}$ alkyl or (CH$_2$)$_n$Ar;

R$^2$ is H, C$_1$-C$_{10}$ alkyl, or (CH$_2$)$_n$Ar; and

R$^3$ is Ar, wherein n is 0, 1, 2 or 3;

Ar is phenyl or phenyl substituted with one or two groups selected from halo, alkyl, or substituted alkyl; or a pharmaceutically acceptable salt thereof.

26. A compound of the formula

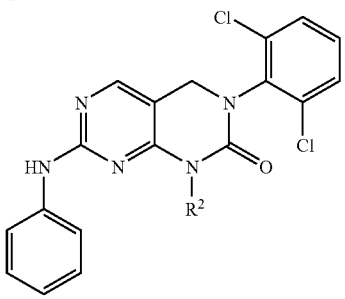

wherein $R^2$ is $(CH_2)_nAr$, n is 0, 1, 2 or 3, and Ar is phenyl or phenyl substituted by a 2-aminoethyl group, or a pharmaceutically acceptable salt thereof.

27. A pharmaceutical formulation comprising the compound or pharmaceutically acceptable salt thereof of claim 1 in combination with a pharmaceutically acceptable carrier, diluent or excipient.

28. A pharmaceutical formulation comprising the compound or pharmaceutically acceptable salt thereof of claim 25 in combination with a pharmaceutically acceptable carrier, diluent or excipient.

29. A pharmaceutical formulation comprising the compound or pharmaceutically acceptable salt thereof of claim 26 in combination with a pharmaceutically acceptable carrier, diluent or excipient.

30. A compound of the formula

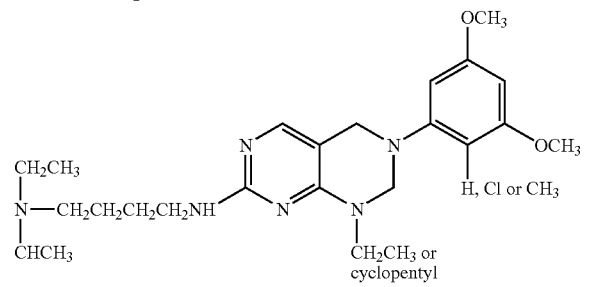

or a pharmaceutically acceptable salt thereof.

31. The compound 7-(4-diethylamino-butylamino)-3-(2-chloro-3,5-dimethoxy-phenyl)-1-ethyl-3,4-dihydro-pyrimido[4,5-d]pyrimidine-2(1H)-one.

32. The compound 7-(4-diethylamino-butylamino)-3-(2-methyl-3,5-dimethoxy-phenyl)-1-ethyl-3,4-dihydro-pyrimido[4,5-d]pyrimidine-2(1H)-one.

33. The compound 7-(4-diethylamino-butylamino)-3-(3,5-dimethoxy-phenyl)-1-cyclopentyl-3,4-dihydro-pyrimido[4,5-d]pyrimidine-2(1H)-one.

34. A compound of VII

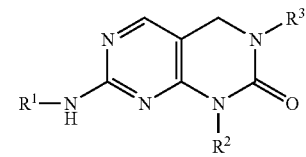

VII or a pharmaceutically acceptable salt thereof,
wherein:
$R^1$ and $R^2$ independently are hydrogen, $C_1$-$C_{10}$ alkyl, $(CH_2)_nAr$, $(CH_2)_n$heteroaryl, $C_3$-$C_{10}$ cycloalkyl, or $(CH_2)_n$ heterocyclyl, wherein n is 0, 1, 2 or 3, and the $(CH_2)_nAr$, $(CH_2)_n$heteroaryl, alkyl, cycloalkyl and $(CH_2)_n$ heterocyclyl groups are optionally substituted by up to 5 groups selected from $NR^4R^5$, $N^+(O)R^4R^5$, $N^+R^4R^5R^6Y^-$, alkyl, phenyl, substituted phenyl, $(CH_2)_n$heteroaryl, hydroxy, alkoxy, phenoxy, thiol, thioalkyl, halo, $COR^4$, $CO_2R^4$, $CONR^4R^5$, $SO_2NR^4R^5$, $SO_3R^4$, $PO_3R^4$, aldehyde, nitrile, nitro, heteroaryloxy, $T(CH_2)_mQR^4$,

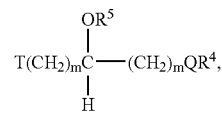

$C(O)T(CH_2)_mQR^4$, $NHC(O)T(CH_2)_mQR^4$, $T(CH_2)_mC(O)NR^4NR^5$, or $T(CH_2)_mCO_2R^4$ wherein each m is independently 1-6, T is O, S, $NR^4$, $N^+(O)R^4$, $N^+R^4R^6Y^-$, or $CR^4R^5$, and Q is O, S, $NR^5$, $N^+(O)R^5$, or $N^+R^5R^6Y^-$;

$R^3$ has the meanings of $R^2$, wherein $R^2$ is as defined above, as well as OH, $NR^4R^5$, $COOR^4$, $OR^4$, $CONR^4R^5$, $SO_2NR^4R^5$, $SO_3R^4$, $PO_3R^4$, $T(CH_2)_mQR^4$,

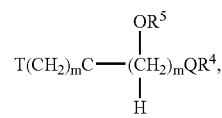

wherein T and Q are as defined above;

$R^4$ and $R^5$ are each independently selected from the group consisting of hydrogen, $C_1$-$C_6$ alkyl, substituted alkyl, $C_2$-$C_6$ alkenyl, $C_2$-$C_6$ alkynyl, $N(C_1$-$C_6alkyl)_1$ or 2 $(CH_2)_nAr$, $C_3$-$C_{10}$ cycloalkyl, heterocyclyl, and heteroaryl, or $R^4$ and $R^5$ together with the nitrogen to which they are attached optionally form a ring having 3 to 7 carbon atoms and said ring optionally contains 1, 2, or 3 heteroatoms selected from the group consisting of nitrogen, substituted nitrogen, oxygen, and sulfur;

when $R^4$ and $R^5$ together with the nitrogen to which they are attached form a ring, the said ring is optionally substituted by 1 to 3 groups selected from OH, $OR^4$, $NR^4R^5$, $(CH_2)_mOR^4$, $(CH_2)_mNR^4R^5$, $T—(CH_2)_mQR_4$, $CO—T—(CH_2)_mQR^4$, $NH(CO)T(CH_2)_mQR^4$, $T—(CH_2)_mCO_2R^4$, or $T(CH_2)_mCONR^4R^5$;

$R^6$ is alkyl; and

Y is a halo counter-ion.

35. A pharmaceutical formulation comprising a compound of claim 34 in combination with a pharmaceutically acceptable carrier, diluent or excipient.

36. A compound of claim 34 wherein $R^1$ is alkyl, pyridyl, or phenyl, each optionally substituted with hydroxy, alkoxy, $NR^4R^5$, or $T(CH_2)_mQR^4$.

* * * * *